(12) United States Patent
Medoff et al.

(10) Patent No.: US 9,206,413 B2
(45) Date of Patent: Dec. 8, 2015

(54) PROCESSING BIOMASS

(71) Applicant: Xyleco, Inc., Woburn, MA (US)

(72) Inventors: Marshall Medoff, Brookline, MA (US); Thomas Craig Masterman, Brookline, MA (US); Harrison Medoff, Brookline, MA (US)

(73) Assignee: Xyleco, Inc., Woburn, MA (US)

( * ) Notice: Subject to any disclaimer, the term of this patent is extended or adjusted under 35 U.S.C. 154(b) by 0 days.

(21) Appl. No.: 13/964,354

(22) Filed: Aug. 12, 2013

(65) Prior Publication Data
US 2013/0344586 A1   Dec. 26, 2013

Related U.S. Application Data

(63) Continuation of application No. 13/662,763, filed on Oct. 29, 2012, now Pat. No. 8,597,917, which is a continuation of application No. 12/782,543, filed on May 18, 2010, now Pat. No. 8,377,668.

(60) Provisional application No. 61/180,032, filed on May 20, 2009, provisional application No. 61/252,293, filed on Oct. 16, 2009.

(51) Int. Cl.
| | |
|---|---|
| *C12M 3/00* | (2006.01) |
| *C12M 1/00* | (2006.01) |
| *C12N 11/02* | (2006.01) |
| *C12N 11/12* | (2006.01) |

(Continued)

(52) U.S. Cl.
CPC ............. *C12N 11/02* (2013.01); *C12N 11/12* (2013.01); *C12P 7/06* (2013.01); *C12P 7/10* (2013.01); *Y02E 50/16* (2013.01); *Y02E 50/17* (2013.01)

(58) Field of Classification Search
CPC ...... C12M 25/00; C12M 47/10; C12M 45/00; C12M 45/06; C12M 45/02; C12M 25/08
See application file for complete search history.

(56) References Cited

U.S. PATENT DOCUMENTS

| | | | | |
|---|---|---|---|---|
| 3,455,853 A | * | 7/1969 | Dekking | ............... C08F 251/00 204/157.63 |
| 3,801,432 A | * | 4/1974 | Free | ........................ D21C 1/00 162/50 |
| 4,405,715 A | * | 9/1983 | Monsan | ........................ 435/105 |

(Continued)

FOREIGN PATENT DOCUMENTS

| | | |
|---|---|---|
| WO | 2008000809 A1 | 1/2008 |
| WO | 2008073186 A2 | 6/2008 |

(Continued)

OTHER PUBLICATIONS

Van Zyl Willem H et al, "Consolidated Bioprocessing for Bioethanol Production using *Saccharomyces cereviside*," Advances in Biochemical Engineering, Biotechnology, Springer, Berlin, DE, (Jan. 1, 2007), pp. 205-235, XP009102631.

(Continued)

*Primary Examiner* — Nathan Bowers
(74) *Attorney, Agent, or Firm* — Leber Patent Law P.C.

(57) ABSTRACT

Biomass (e.g., plant biomass, animal biomass, and municipal waste biomass) is processed for use in the production of useful products, such as fuels. For example, systems can use biomass materials, such as cellulosic and/or lignocellulosic materials, to enhance the production of a product, e.g., the production of ethanol and/or butanol by fermentation.

18 Claims, 22 Drawing Sheets

(51) Int. Cl.
C12P 7/06 (2006.01)
C12P 7/10 (2006.01)

(56) References Cited

U.S. PATENT DOCUMENTS

| | | | |
|---|---|---|---|
| 4,722,898 A * | 2/1988 | Errede et al. | 435/182 |
| 4,769,082 A * | 9/1988 | Kumakura et al. | 127/37 |
| 5,595,893 A | 1/1997 | Pometto, III et al. | |
| 2003/0148401 A1* | 8/2003 | Agrawal | B01J 19/0046 506/9 |
| 2003/0187102 A1 | 10/2003 | Medoff et al. | |
| 2007/0045456 A1* | 3/2007 | Medoff | 241/24.29 |
| 2008/0009063 A1* | 1/2008 | Okano | C12N 5/0068 435/402 |
| 2008/0020437 A1* | 1/2008 | Savarese | 435/165 |
| 2009/0286295 A1 | 11/2009 | Medoff et al. | |
| 2010/0112242 A1 | 5/2010 | Medoff et al. | |

FOREIGN PATENT DOCUMENTS

WO 2006/102543 A2 9/2009
WO 2009/134816 A1 11/2009

OTHER PUBLICATIONS

Mohagheghi A et al, "Cofermentation of Glucose, Xylose, and Arabinose by Genomic DNA-integrated Xylose/arabinose Fermenting Strain of Zymomonas Mobilis AX101," Applied Biochemistry and Biotechnology, Humana Press, Inc., US, vol. 98-100, (Apr. 1, 2002), pp. 885-898, XP002404431.
Fujita Y et al, "Synergistic Saccharification, and Direct Fermentation to Ethanol, of Amorphous Cellulose by Use of an Engineered Yeast Strain Codisplaying Three Types of Cellulolytic Enzyme," Applied and Environmental Microbiology, American Society for Microbiology, US, vol. 70, No. 2, (Feb. 1, 2004), pp. 1207-1212, XP002368082.
PCT ISR and Written Opinion for PCT/US2009/042000, mailed Sep. 30, 2009, 14 pages.
Kato et al., "Surface Oxidation of Cellulose Fibers by Vacuum Ultraviolet Radiation," Journal of Polymer Science: Part A: Polymer Chemistry, vol. 37, 357-361 (1999).
Dziedziela, et al., "Functional Groups in Gamma-Irradiated Cellulose," Radiation Physics and Chemistry, 1984, vol. 23(6), pp. 723-725.
Takacs et al., "Effect of Gamma-Irradiation on Cotton-Cellulose," Radiation Physics and Chemistry, 1999, vol. 55, pp. 663-666.
Gerber et al., "Adsorption of a Trichoderma reesei endoglucanase and cellobiohydrolast onto bleached Kraft fibres," Cellulose, 1997, vol. 4, p. 255-268.
Eklund et al., "Simultaneous saccharification and fermentation of steam-pretreated willow," Enzyme and Microbial Technology, 1995, vol. 17, p. 255-259.
Szengyel et al., "Effect of Acetic Acid and Furfural on Cellulase Production of Trichoderma reesei RUT C30," Applied Biochemistry and Biotechnology, 2002, vol. 89, p. 31-42.
Chunping et al., "Effect and Aftereffect of Gamma Irradiation Pretreatment on Enzymatic Hydrolysis of Wheat Straw," Bioresource Technology, Jan. 2008, vol. 99, p. 6240-6245.
Sun et al., "Hydrolysis of Lignocellulosic Materials for Ethanol Production: A review," Bioresource Technology, 2002, vol. 83, p. 1-11.

Kaetsu et al., "Immobilization of microbial cell and yeast cell and its application to biomass conversion using radiation techniques," Radiation Phys. Chem., vol. 29, No. 3, pp. 191-193 (1987).
Hirosawa et al, "Influence of carboxyl group on the acid hydrolysis of cellulose," J Wood Sci, 2001, vol. 47, p. 141-144.
Palonen et al., "Role of Oxidative Enzymatic Treatments on Enzymatic Hydrolysis of Softwood," 2004, Wiley periodicals, p. 550-557.
Rudolf A. et al., "Simultaneous Saccharification and Fermentation of Steam-Pretreated Bagasse Using *Saccharomyces cerevisiae* TMB3400 and Pichia stipitus CBS6054," Biotechnology and Bioengineering 20080301, vol. 99, No. 4, Mar. 1, 2008, pp. 783-790, XP002605571.
Marques et al., "Conversion of Recycled Paper Sludge to Ethanol by SHF and SSF using Pichia stipitis," Biomass and Bioenergy, Pergamon, Oxford, GB, vol. 32, No. 5, May 1, 2008, pp. 400-406, XP022664168.
Beardmore et al., "Gamma-Ray Irradiation as a Pre-Treatment for the Enzymatic Hydrolysis of Cellulose," Biotechnology Letters, Kew, Surrey, GB, vol. 2, No. 10, Oct. 1, 1980, pp. 435-438, XP002566022.
Lepifre et al., "Lignin Incorporation Combined with Electron-Beam Irradiation Improves the Surface Water Resistance of Starch Films," Biomacromolecules, vol. 5, No. 5, Sep. 2004, pp. 1678-1686, XP002605572.
Borjesson et al., "Effect of Poly(ethylene glycol) on Enzymatic Hydrolysis and Adsorption of Cellulase Enzymes to Pretreated Lignocellulose," Enzyme and Microbial Technology, Stoneham, MA, US, vol. 41, No. 1-2, May 10, 2007, pp. 186-195, XP022069900.
ISR for counterpart application PCT/US2010/035290, European Patent Office as ISA, mailed Oct. 29, 2010, 8 pages.
Written Opinion for counterpart application PCT/US2010/035290, European Patent Office as ISA, mailed Oct. 29, 2010, 10 pages.
E.P. Bardi and Koutina, A.A., "Immobilization of Yeast on Delignified Cellulosic Material for Room Temperature and Low-Temperature Wine Making," J. Agric. Food Chem., vol. 42: 221-228 (1994).
A.W. Khan et al., "Electron Beam Irradiation Pretreatment and Enzymatic Saccharification of Used Newsprint and Paper Mill Wastes," Radiat. Phys. Chem., vol. 29, No. 2: 117-120 (1987).
Fujii, N. et al., "Influence of surface characteristics of cellulose carriers on ethanol production by immobilized yeast cells," Process Biochemistry, 1999, vol. 34: 147-152.
Haapala, R. et al., "Production of extracellular enzymes by immobilized Trichoderma reesei in shake flask cultures," Appl. Microbiol. Biotechnol., vol. 43: 815-821 (1995).
Heyn, A.N.J., "The Microcrystalline Structure of Cellulose in Cell Walls of Cotton Ramie, and Jute Fibers As Revealed by Negative Staining of Sections," J. of Cell Biol., vol. 29: 181-197 (1966).
Huang, Y. and Yang, S-T, "Acetate Production from Whey Lactose Using Co-Immobilized Cells of Homolactic and Homoacetic Bacteria in a Fibrous-Bed Bioreactor," Biotechnol. Bioeng., vol. 60: 498-507 (1998).
Yu, J. et al., "An novel immobilization method of *Saccharomyces cerevisiae* to sorghum bagasse for ethanol production," J. Biotechnol., vol. 129: 415-520 (2007).
Yamada, T. et al., "Performance of Immobilized Zymomonas mobilis 31821 (pZB5) on Actual Hydrolysates Produced by Arkenol Technology," Appl. Biochem. Biotechnol., vol. 98-100: 899-906 (2002).
Mitchell et al., Cellulose, vol. 12: 629-639 (2005).
Huang et al., Appl. Biochem. Biotechnol., vol. 113-116: 887-898 (2004).

* cited by examiner

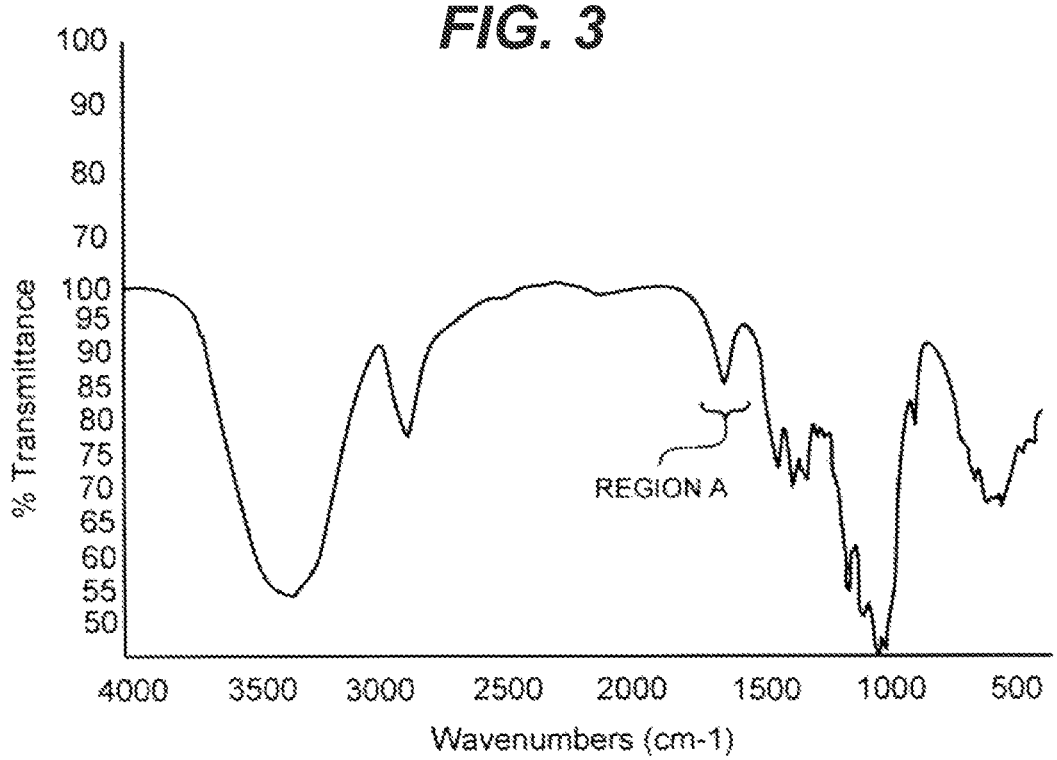
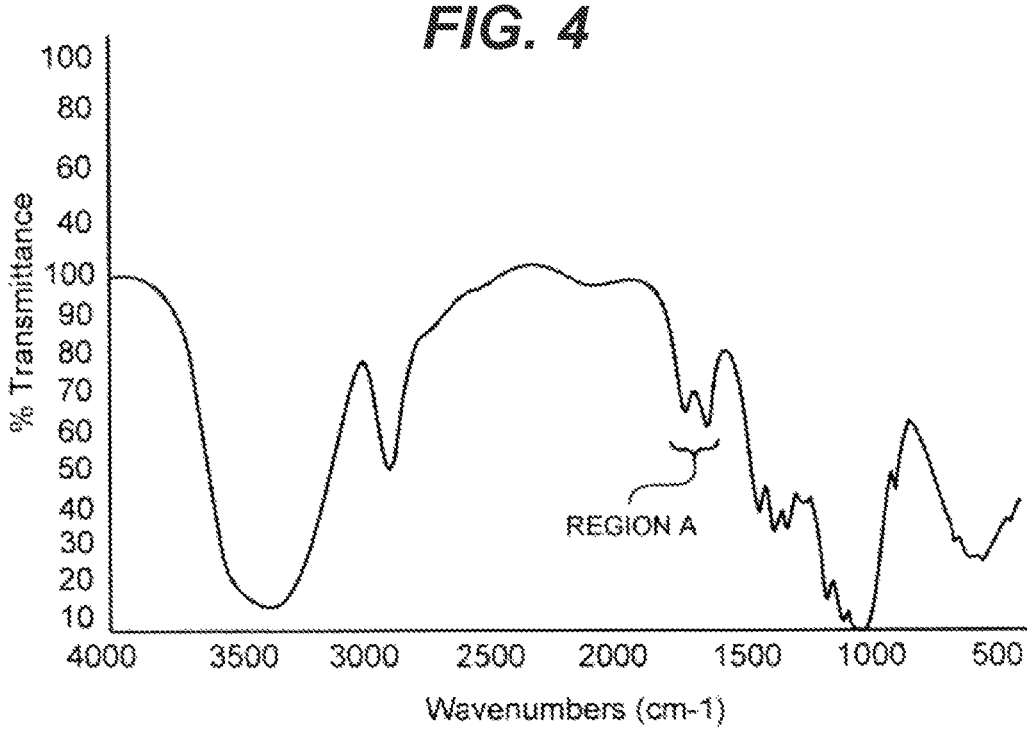

PROCESSING BIOMASS

RELATED APPLICATIONS

This application claims priority to copending U.S. application Ser. No. 13/662,763 filed Oct. 29, 2013; which claims priority to U.S. application Ser. No. 12/782,543 filed May 18, 2010, U.S. Pat. No. 8,377,668 issued Feb. 19, 2013; which claimed priority to U.S. Provisional Application Ser. No. 61/180,032, filed May 20, 2009, and U.S. Provisional Application Ser. No. 61/252,293, filed Oct. 16, 2009. The complete disclosure of each of these is hereby incorporated by reference herein.

BACKGROUND

Cellulosic and lignocellulosic materials are produced, processed, and used in large quantities in a number of applications. Often such materials are used once, and then discarded as waste, or are simply considered to be waste materials, e.g., sewage, bagasse, sawdust, and stover.

Various cellulosic and lignocellulosic materials, their uses, and applications have been described in U.S. Pat. Nos. 7,307,108, 7,074,918, 6,448,307, 6,258,876, 6,207,729, 5,973,035 and 5,952,105; and in various patent applications, including "FIBROUS MATERIALS AND COMPOSITES," PCT/US2006/010648, filed on Mar. 23, 2006, and "FIBROUS MATERIALS AND COMPOSITES," U.S. Patent Application Publication No. 2007/0045456.

SUMMARY

In some instances, the presence of biomass in a process, for example fermentation, facilitates conversion of a low molecular weight sugar to an intermediate or a product. The inventors have found that including biomass in a mixture with a low molecular weight sugar, a medium, e.g., a solvent or solvent system, and a microorganism can improve the yield and production rate of an intermediate or a product obtained by conversion of the sugar, for example an alcohol such as ethanol or butanol. Including the biomass can also prevent incomplete, sluggish, or "stuck" product conversion, e.g., by fermentation.

The biomass may not in itself be converted to the product (such as an alcohol), or may be partially or fully converted to the product along with the low molecular weight sugar.

In instances where the biomass is partially converted, the surface area and porosity of the biomass is increased relative to the surface area and porosity of the starting biomass, which can advantageously increase the conversion rate of the low molecular weight sugar to the product.

In some cases, the biomass may be the remnants of a cellulosic or lignocellulosic material that has been saccharified, e.g., lignin and/or other materials that are left over after cellulose has been converted to sugar.

In one aspect, the invention features a method that includes utilizing a microorganism and/or enzyme that is immobilized on a biomass material, e.g., functionalized biomass fibers, to convert a carbohydrate, e.g., a low molecular weight sugar, to a product. By "immobilized," it is meant that the microorganism and/or enzyme is bonded, directly or indirectly (e.g., through a chemical linker), to the fibers by covalent, hydrogen, ionic, or equivalent bonding, and/or by mechanical interaction, e.g., between the microorganism and pores of the biomass material, e.g., fibers. Bonding may be created, e.g., by electrically polarizing the biomass material. The interaction can be permanent, semi-permanent, or fleeting. Mechanical interaction may include the microorganism or enzyme nesting in or clinging to pores or other sites of the biomass material.

Some implementations include one or more of the following features.

Converting can include allowing the microorganism to convert at least a portion of the low molecular weight sugar to an alcohol, e.g., ethanol or butanol, or to a hydrocarbon or hydrogen. Converting may include fermentation. The microorganism may comprise a yeast, e.g., *S. cerevisiae* and/or *P. stipitis*, or a bacterium, e.g., *Zymomonas mobilis*. The method may further include irradiating the biomass fibers, e.g., with ionizing radiation, for example using a particle beam. The biomass fibers may have a BET surface area of greater than 0.25 $m^2/g$, and/or a porosity of at least 70%. The biomass fibers may be derived from a biomass material that has internal fibers, and that has been sheared to an extent that its internal fibers are substantially exposed.

In another aspect, the invention features a mixture that includes a biomass material having polar functional groups, a microorganism having complementary attractive functional groups, and a liquid medium.

In a further aspect, the invention features a composition comprising biomass fibers having functional groups, and a microorganism having complementary attractive functional groups, the microorganism being immobilized on the biomass fibers.

The invention also features a method that includes converting a low molecular weight sugar, or a material that includes a low molecular weight sugar, in a mixture with a biomass, a microorganism, and a solvent or a solvent system, e.g., water or a mixture of water and an organic solvent, to a product. Examples of solvents or solvent systems include water, hexane, hexadecane, glycerol, chloroform, toluene, ethyl acetate, petroleum ether, liquefied petroleum gas (LPG), ionic liquids and mixtures thereof. The solvent or solvent system can be in the form of a single phase or two or more phases. The biomass can be, e.g., in fibrous form.

In some instances, having a biomass material (e.g., treated by any method described herein or untreated) present during production of a product, can enhance the production rate of the product. Without wishing to be bound by any particular theory, it is believed that having a solid present, such as a high surface area and/or high porosity solid, can increase reaction rates by increasing the effective concentration of solutes and providing a substrate on which reactions can occur.

In some embodiments, a biomass material that has been irradiated, oxidized, chemically treated, mechanically treated, sonicated, steam exploded and/or pyrolyzed, can be added to a low molecular weight sugar fermentation process, e.g., to enhance fermentation rate and output.

For example, an irradiated or an un-irradiated biomass material, e.g., a paper fiber, can be added to a fermentation process, such as during a corn-ethanol fermentation or a sugarcane extract fermentation, to increase the rate of production by at least 10, 15, 20, 30, 40, 50, 75, 100 percent or more, e.g., at least 150 percent, or even up to 1000 percent. Conversion, e.g., fermentation, can exhibit a percent performance, as defined in the Examples herein, of at least 140%, in some cases at least 170%.

The biomass material can have a high surface area, high porosity, and/or low bulk density. In some embodiments, the biomass is present in the mixture from about 0.5 percent to about 50 percent by weight, such as between about 1 percent and about 25 percent by weight, or between about 2 percent and about 12.5 percent by weight. In other embodiments, the biomass is present in amounts greater than about 0.5 percent by weight, such as greater than about 1, 2, 3, 4, 5, 6, 7, 8, 9, or even greater than about 10 percent by weight.

Because the biomass material is not itself consumed during the conversion process, the biomass material can be reused in multiple batch processes, or can be used continuously for the production of a relatively large volume of the product.

Some implementations include one or more of the following features. The method can include irradiating the fibrous biomass prior to mixing, e.g., with ionizing radiation, for example at a total dosage of at least 5 Mrad. Irradiating can be performed using a particle beam. Irradiating can be conducted under conditions selected to reduce the molecular weight of the biomass. Irradiation can be performed using multiple applications of radiation. The ionizing radiation can include electron beam radiation. For example, the radiation can be applied at a total dose of between about 10 Mrad and about 150 Mrad, such as at a dose rate of about 0.5 to about 10 Mrad/day, or 1 Mrad/s to about 10 Mrad/s. In some embodiments, irradiating includes applying two or more radiation sources, such as gamma rays and a beam of electrons.

In some embodiments, irradiating is performed on the biomass feedstock while the biomass feedstock is exposed to air, nitrogen, oxygen, helium, or argon. In some embodiments, pretreatment can include pretreating the biomass feedstock with steam explosion.

In some embodiments, the method includes mechanically treating the biomass, e.g., by reducing one or more dimensions of individual pieces of biomass, for example by shearing, stone grinding, mechanically ripping or tearing, pin grinding, wet or dry grinding, air attrition milling, cutting, squeezing, compressing or combinations of any of these processes. In some cases, after mechanical treatment the biomass includes fibers having an average length-to-diameter ratio of greater than 5/1. In some embodiments, the prepared biomass can have a BET surface area of greater than 0.25 $m^2/g$. The mechanically treated biomass can have a bulk density of less than about 0.5 $g/cm^3$, e.g., less than 0.35 $g/cm^3$.

In any of the methods disclosed herein, radiation may be applied from a device that is in a vault.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 3 is an infrared spectrum of Kraft board paper sheared on a rotary knife cutter.

FIG. 4 is an infrared spectrum of the Kraft paper of FIG. 3 after irradiation with 100 Mrad of gamma radiation.

DETAILED DESCRIPTION

Figure 1:
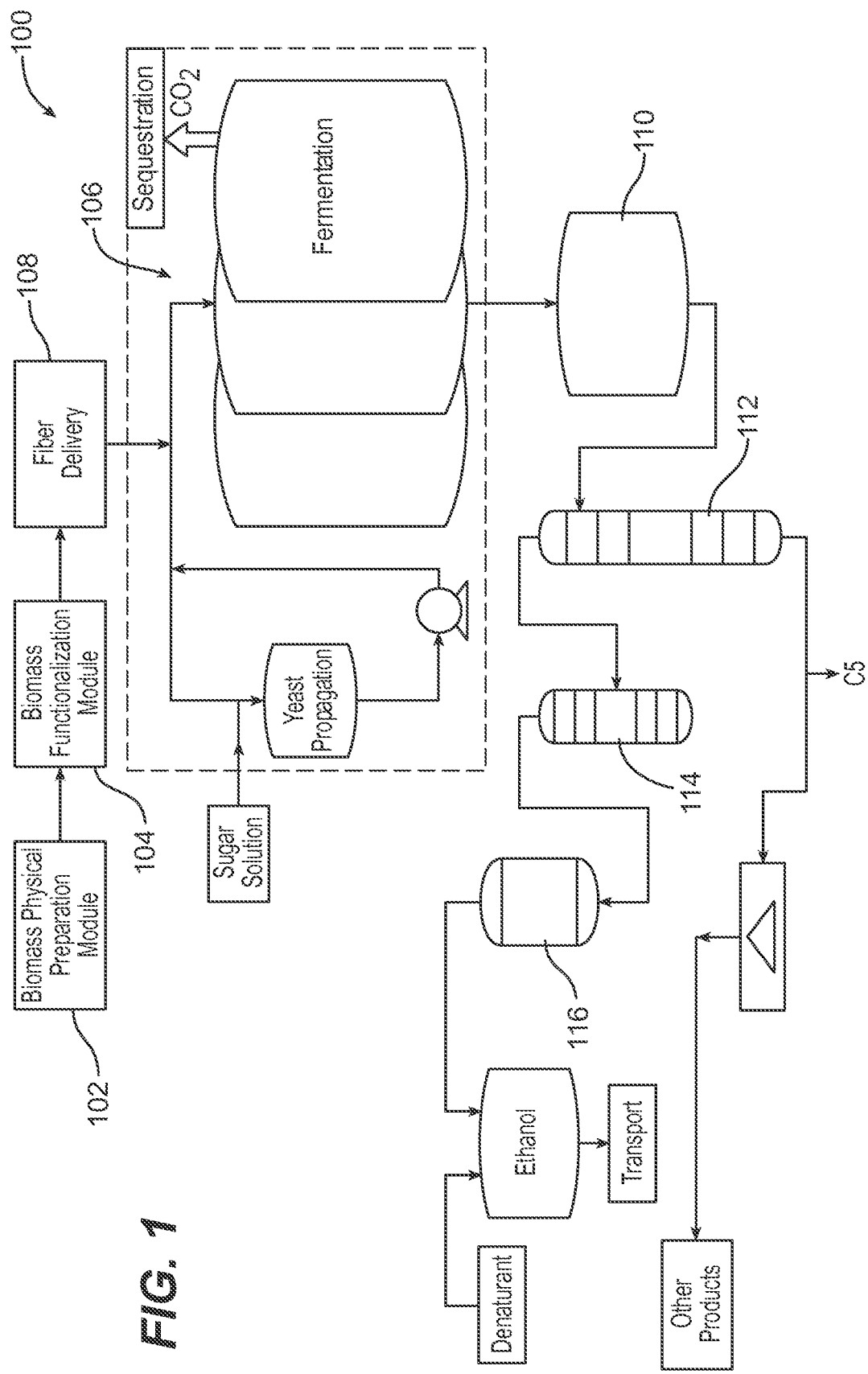
FIG. 1 is a block diagram illustrating treatment of biomass and the use of the treated biomass in a fermentation process.

Functionalized biomass materials having desired types and amounts of functionality, such as carboxylic acid groups, enol groups, aldehyde groups, ketone groups, nitrile groups, nitro groups, or nitroso groups, can be prepared using the methods described herein. Such functionalized materials can facilitate conversion of low molecular weight sugar to a product, e.g., during a fermentation process.

Types of Biomass

Preferred biomass materials for use in the processes described herein contain fibers which can be functionalized with functional groups that are complementary with functional groups on an agent to be used in converting the sugar, e.g., a microorganism such as yeast.

Fiber sources include cellulosic fiber sources, including paper and paper products (e.g., polycoated paper and Kraft paper), and lignocellulosic fiber sources, including wood, and wood-related materials, e.g., particleboard. Other suitable fiber sources include natural fiber sources, e.g., grasses, rice hulls, bagasse, jute, hemp, flax, bamboo, sisal, abaca, straw, switchgrass, alfalfa, hay, corn cobs, corn stover, coconut hair; fiber sources high in α-cellulose content, e.g., cotton; and synthetic fiber sources, e.g., extruded yarn (oriented yarn or un-oriented yarn). Natural or synthetic fiber sources can be obtained from virgin scrap textile materials, e.g., remnants or they can be post consumer waste, e.g., rags. When paper products are used as fiber sources, they can be virgin materials, e.g., scrap virgin materials, or they can be post-consumer waste. Aside from virgin raw materials, post-consumer, industrial (e.g., offal), and processing waste (e.g., effluent from paper processing) can also be used as fiber sources. Also, the fiber source can be obtained or derived from human (e.g., sewage), animal or plant wastes. Additional fiber sources have been described in U.S. Pat. Nos. 6,448,307, 6,258,876, 6,207,729, 5,973,035 and 5,952,105.

In some embodiments, the biomass material includes a carbohydrate that is or includes a material having one or more β-1,4-linkages and having a number average molecular weight between about 3,000 and 50,000. Such a carbohydrate is or includes cellulose (I), which is derived from (β-glucose 1) through condensation of β(1,4)-glycosidic bonds. This linkage contrasts itself with that for α(1,4)-glycosidic bonds present in starch and other carbohydrates.

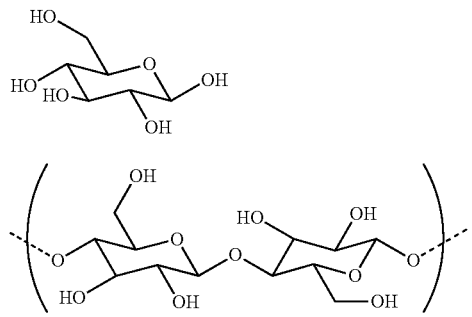

Starchy materials include starch itself, e.g., corn starch, wheat starch, potato starch or rice starch, a derivative of starch, or a material that includes starch, such as an edible food product or a crop. For example, the starchy material can be arracacha, buckwheat, banana, barley, cassava, kudzu, oca, sago, sorghum, regular household potatoes, sweet potato, taro, yams, or one or more beans, such as favas, lentils or peas. Blends of any two or more starchy materials are also starchy materials.

In some cases the biomass is a microbial material. Microbial sources include, but are not limited to, any naturally occurring or genetically modified microorganism or organism that contains or is capable of providing a source of carbohydrates (e.g., cellulose), for example, protists, e.g., animal protists (e.g., protozoa such as flagellates, amoeboids, ciliates, and sporozoa) and plant protists (e.g., algae such alveolates, chlorarachniophytes, cryptomonads, euglenids, glaucophytes, haptophytes, red algae, stramenopiles, and viridaeplantae). Other examples include seaweed, plankton (e.g., macroplankton, mesoplankton, microplankton, nanoplankton, picoplankton, and femptoplankton), phytoplankton, bacteria (e.g., gram positive bacteria, gram negative bacteria, and extremophiles), yeast and/or mixtures of these. In some instances, microbial biomass can be obtained from natural sources, e.g., the ocean, lakes, bodies of water, e.g., salt water or fresh water, or on land. Alternatively or in addition, microbial biomass can be obtained from culture systems, e.g., large scale dry and wet culture systems.

Blends of any biomass materials described herein can be utilized for making any of the intermediates or products described herein. For example, blends of cellulosic materials and starchy materials can be utilized for making any product described herein.

Systems for Treating Biomass and Using Treated Biomass in Fermentation

FIG. 1 shows a system 100 for treating biomass, particularly fibrous biomass, and then using the treated biomass to enhance a fermentation process. System 100 includes a module 102 in which a biomass feedstock is mechanically treated, e.g., exposing internal fibers of the feedstock. Examples of mechanical treatments will be described in detail below. The system 100 also includes a module 104 in which the mechanically treated feedstock is functionalized, e.g., by irradiation. After functionalization, the functionalized fibers are delivered to a fermentation system 106 by a delivery module 108.

Figure 2:
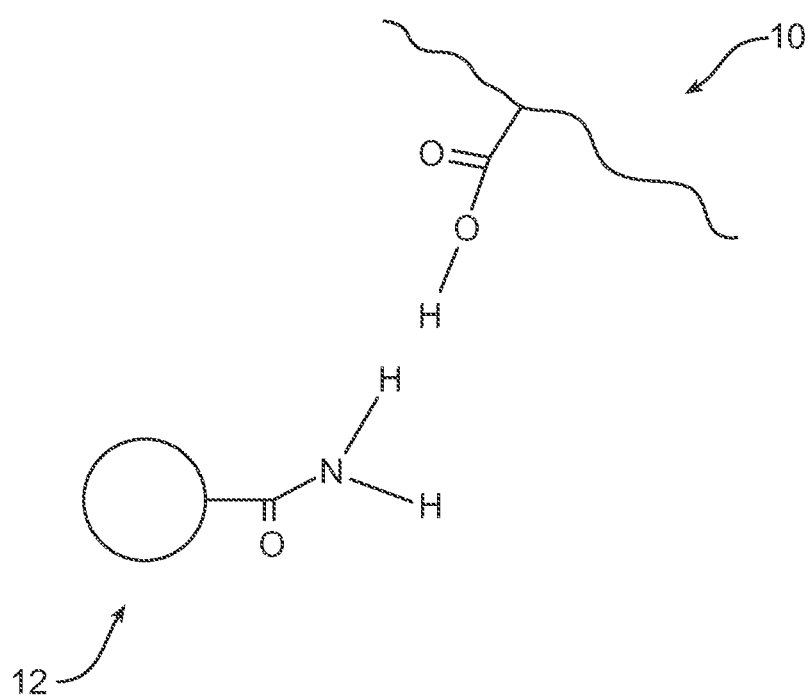
FIG. 2 is a schematic representation of functionalized biomass interacting with a microorganism.

The functionalized fibers are then present during fermentation and enhance the fermentation process by providing a substrate that can interact with the microorganisms used in fermentation, e.g., yeast cells. This interaction is shown schematically in FIG. 2, which depicts a functionalized polar fiber 10 and a yeast cell 12 having a complementary polar functional group. Due to the polarity of the fibers and the yeast cell, the cell can become immobilized on one or more of the fibers. Bonding of the yeast cell (or other microorganism) to the fibers may be by hydrogen bonding, or by covalent or ionic bonding. In some cases, the functional groups on the fibers may react with those on the microorganism, forming a covalent bond. The increased surface area and porosity of the biomass material that results from mechanical treatment (e.g., in module 102) provides a greater surface area for interaction of the fiber and microorganism and thus enhances this interaction. The immobilized cells are more productive, increasing the efficiency and yield of the fermentation process and preventing the process from becoming prematurely "stuck."

It is noted that if mixing is performed during fermentation, the mixing is preferably relatively gentle (low shear) so as to minimize disruption of the interaction between the microorganisms and fibers. In some embodiments, jet mixing is used, as described in U.S. Ser. No. 61/218,832 and U.S. Ser. No. 61/179,995, the complete disclosures of which are incorporated herein by reference.

Referring again to FIG. 1, fermentation produces a crude ethanol mixture, which flows into a holding tank 110. Water or other solvent, and other non-ethanol components, are stripped from the crude ethanol mixture using a stripping column 112, and the ethanol is then distilled using a distillation unit 114, e.g., a rectifier. Finally, the ethanol can be dried using a molecular sieve 116, denatured if necessary, and output to a desired shipping method.

In some cases, the systems described herein, or components thereof, may be portable, so that the system can be transported (e.g., by rail, truck, or marine vessel) from one location to another. The method steps described herein can be performed at one or more locations, and in some cases one or more of the steps can be performed in transit. Such mobile processing is described in U.S. Ser. No. 12/374,549 and International Application No. WO 2008/011598, the full disclosures of which are incorporated herein by reference.

Any or all of the method steps described herein can be performed at ambient temperature. If desired, cooling and/or heating may be employed during certain steps. For example, the feedstock may be cooled during mechanical treatment to increase its brittleness. In some embodiments, cooling is employed before, during or after the initial mechanical treatment and/or the subsequent mechanical treatment. Cooling may be performed as described in Ser. No. 12/502,629, the full disclosure of which is incorporated herein by reference. Moreover, the temperature in the fermentation system 106 may be controlled to enhance fermentation.

Physical Treatment

Physical treatment processes that may be used to change the morphology of the biomass material and/or to functionalize the material can include one or more of any of those described herein, such as mechanical treatment, chemical treatment, irradiation, sonication, oxidation, pyrolysis or steam explosion. Treatment methods can be used in combinations of two, three, four, or even all of these technologies (in any order). When more than one treatment method is used, the methods can be applied at the same time or at different times. Other processes that functionalize a biomass feedstock and/or alter its morphology may also be used, alone or in combination with the processes disclosed herein.

Mechanical Treatments

In some cases, methods can include mechanically treating the biomass feedstock. Mechanical treatments include, for example, cutting, milling, pressing, grinding, shearing and chopping. Milling may include, for example, ball milling, hammer milling, rotor/stator dry or wet milling, or other types of milling. Other mechanical treatments include, e.g., stone grinding, cracking, mechanical ripping or tearing, pin grinding or air attrition milling.

Mechanical treatment can be advantageous for "opening up," "stressing," breaking and shattering the cellulosic or lignocellulosic materials, making the cellulose of the materials more susceptible to chain scission and/or reduction of crystallinity. The open materials can also be more susceptible to oxidation when irradiated.

In some cases, the mechanical treatment may include an initial preparation of the feedstock as received, e.g., size reduction of materials, such as by cutting, grinding, shearing, pulverizing or chopping. For example, in some cases, loose feedstock (e.g., recycled paper, starchy materials, or switchgrass) is prepared by shearing or shredding.

Alternatively, or in addition, the feedstock material can first be physically treated by one or more of the other physical treatment methods, e.g., chemical treatment, radiation, sonication, oxidation, pyrolysis or steam explosion, and then mechanically treated. This sequence can be advantageous since materials treated by one or more of the other treatments, e.g., irradiation or pyrolysis, tend to be more brittle and, therefore, it may be easier to further change the molecular structure of the material by mechanical treatment.

In some embodiments, the biomass material is fibrous, and mechanical treatment includes shearing to expose fibers of the fibrous material. Shearing can be performed, for example, using a rotary knife cutter. Other methods of mechanically treating the biomass include, for example, milling or grinding. Milling may be performed using, for example, a hammer mill, ball mill, colloid mill, conical or cone mill, disk mill, edge mill, Wiley mill or grist mill. Grinding may be performed using, for example, a stone grinder, pin grinder, coffee grinder, or bun grinder. Grinding may be provided, for example, by a reciprocating pin or other element, as is the case in a pin mill. Other mechanical treatment methods include mechanical ripping or tearing, other methods that apply pressure to the material, and air attrition milling. Suitable mechanical treatments further include any other technique that changes the molecular structure or morphology of the biomass material.

If desired, the mechanically treated material can be passed through a screen, e.g., having an average opening size of 1.59 mm or less (1/16 inch, 0.0625 inch). In some embodiments, shearing, or other mechanical treatment, and screening are performed concurrently. For example, a rotary knife cutter can be used to concurrently shear and screen the biomass material. The biomass is sheared between stationary blades and rotating blades to provide a sheared material that passes through a screen, and is captured in a bin.

The biomass material can be mechanically treated in a dry state (e.g., having little or no free water on its surface), a hydrated state (e.g., having up to ten percent by weight absorbed water), or in a wet state, e.g., having between about 10 percent and about 75 percent by weight water. The biomass material can even be mechanically treated while partially or fully submerged under a liquid, such as water, ethanol or isopropanol. The biomass material can also be mechanically treated under a gas (such as a stream or atmosphere of gas other than air), e.g., oxygen or nitrogen, or steam.

Mechanical treatment systems can be configured to produce streams with specific morphology characteristics such as, for example, surface area, porosity, bulk density, and, in the case of fibrous feedstocks, fiber characteristics such as length-to-width ratio.

In some embodiments, a BET surface area of the mechanically treated material is greater than 0.1 $m^2/g$, e.g., greater than 0.25 $m^2/g$, greater than 0.5 $m^2/g$, greater than 1.0 $m^2/g$, greater than 1.5 $m^2/g$, greater than 1.75 $m^2/g$, greater than 5.0 $m^2/g$, greater than 10 $m^2/g$, greater than 25 $m^2/g$, greater than 35 $m^2/g$, greater than 50 $m^2/g$, greater than 60 $m^2/g$, greater than 75 $m^2/g$, greater than 100 $m^2/g$, greater than 150 $m^2/g$, greater than 200 $m^2/g$, or even greater than 250 $m^2/g$.

A porosity of the mechanically treated material can be, e.g., greater than 20 percent, greater than 25 percent, greater than 35 percent, greater than 50 percent, greater than 60 percent, greater than 70 percent, greater than 80 percent, greater than 85 percent, greater than 90 percent, greater than 92 percent, greater than 94 percent, greater than 95 percent, greater than 97.5 percent, greater than 99 percent, or even greater than 99.5 percent.

In some embodiments, after mechanical treatment the material has a bulk density of less than 0.25 $g/cm^3$, e.g., 0.20 $g/cm^3$, 0.15 $g/cm^3$, 0.10 $g/cm^3$, 0.05 $g/cm^3$ or less, e.g., 0.025 $g/cm^3$. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters.

If the biomass is a fibrous material the fibers of the mechanically treated material can have a relatively large average length-to-diameter ratio (e.g., greater than 20-to-1), even if they have been sheared more than once. In addition, the fibers of the fibrous materials described herein may have a relatively narrow length and/or length-to-diameter ratio distribution.

As used herein, average fiber widths (e.g., diameters) are those determined optically by randomly selecting approximately 5,000 fibers. Average fiber lengths are corrected length-weighted lengths. BET (Brunauer, Emmet and Teller) surface areas are multi-point surface areas, and porosities are those determined by mercury porosimetry.

If the biomass is a fibrous material the average length-to-diameter ratio of fibers of the mechanically treated material can be, e.g., greater than 8/1, e.g., greater than 10/1, greater than 15/1, greater than 20/1, greater than 25/1, or greater than 50/1. An average fiber length of the mechanically treated material can be, e.g., between about 0.5 mm and 2.5 mm, e.g., between about 0.75 mm and 1.0 mm, and an average width (e.g., diameter) of the second fibrous material 14 can be, e.g., between about 5 μm and 50 μm, e.g., between about 10 μm and 30 μm.

In some embodiments, if the biomass is a fibrous material the standard deviation of the fiber length of the mechanically treated material can be less than 60 percent of an average fiber length of the mechanically treated material, e.g., less than 50 percent of the average length, less than 40 percent of the average length, less than 25 percent of the average length, less than 10 percent of the average length, less than 5 percent of the average length, or even less than 1 percent of the average length.

In some situations, it can be desirable to prepare a low bulk density material, densify the material (e.g., to make it easier and less costly to transport to another site), and then revert the material to a lower bulk density state. Densified materials can be processed by any of the methods described herein, or any material processed by any of the methods described herein can be subsequently densified, e.g., as disclosed in U.S. Ser.

No. 12/429,045 and WO 2008/073186, the full disclosures of which are incorporated herein by reference.

Radiation Treatment

One or more radiation processing sequences can be used to process the biomass, e.g., to functionalize the material. Radiation can also sterilize the materials, or any media needed to bioprocess the material.

In some embodiments, energy deposited in a material that releases an electron from its atomic orbital is used to irradiate the materials. The radiation may be provided by (1) heavy charged particles, such as alpha particles or protons, (2) electrons, produced, for example, in beta decay or electron beam accelerators, or (3) electromagnetic radiation, for example, gamma rays, x rays, or ultraviolet rays. In one approach, radiation produced by radioactive substances can be used to irradiate the feedstock. In another approach, electromagnetic radiation (e.g., produced using electron beam emitters) can be used to irradiate the feedstock. In some embodiments, any combination in any order or concurrently of (1) through (3) may be utilized. The doses applied depend on the desired effect and the particular feedstock.

In some instances when chain scission is desirable and/or polymer chain functionalization is desirable, particles heavier than electrons, such as protons, helium nuclei, argon ions, silicon ions, neon ions, carbon ions, phoshorus ions, oxygen ions or nitrogen ions can be utilized. When ring-opening chain scission is desired, positively charged particles can be utilized for their Lewis acid properties for enhanced ring-opening chain scission. For example, when maximum oxidation is desired, oxygen ions can be utilized, and when maximum nitration is desired, nitrogen ions can be utilized. The use of heavy particles and positively charged particles is described in U.S. Ser. No. 12/417,699, the full disclosure of which is incorporated herein by reference.

In one method, a first material that is or includes cellulose having a first number average molecular weight ($M_{N1}$) is irradiated, e.g., by treatment with ionizing radiation (e.g., in the form of gamma radiation, X-ray radiation, 100 nm to 280 nm ultraviolet (UV) light, a beam of electrons or other charged particles) to provide a second material that includes cellulose having a second number average molecular weight ($M_{N2}$) lower than the first number average molecular weight. The second material (or the first and second material) can be combined with a microorganism (with or without enzyme treatment) that can utilize the second and/or first material or its constituent sugars or lignin to produce an intermediate or product, such as those described herein.

Since the second material includes cellulose having a reduced molecular weight relative to the first material, and in some instances, a reduced crystallinity as well, the second material is generally more dispersible, swellable and/or soluble, e.g., in a solution containing a microorganism and/or an enzyme. These properties make the second material easier to process and more susceptible to chemical, enzymatic and/or biological attack relative to the first material, which can greatly improve the production rate and/or production level of a desired product, e.g., ethanol.

In some embodiments, the second number average molecular weight ($M_{N2}$) is lower than the first number average molecular weight ($M_{N1}$) by more than about 10 percent, e.g., more than about 15, 20, 25, 30, 35, 40, 50 percent, 60 percent, or even more than about 75 percent.

In some instances, the second material includes cellulose that has a crystallinity ($C_2$) that is lower than the crystallinity ($C_1$) of the cellulose of the first material. For example, ($C_2$) can be lower than ($C_1$) by more than about 10 percent, e.g., more than about 15, 20, 25, 30, 35, 40, or even more than about 50 percent.

In some embodiments, the starting crystallinity index (prior to irradiation) is from about 40 to about 87.5 percent, e.g., from about 50 to about 75 percent or from about 60 to about 70 percent, and the crystallinity index after irradiation is from about 10 to about 50 percent, e.g., from about 15 to about 45 percent or from about 20 to about 40 percent. However, in some embodiments, e.g., after extensive irradiation, it is possible to have a crystallinity index of lower than 5 percent. In some embodiments, the material after irradiation is substantially amorphous.

In some embodiments, the starting number average molecular weight (prior to irradiation) is from about 200,000 to about 3,200,000, e.g., from about 250,000 to about 1,000,000 or from about 250,000 to about 700,000, and the number average molecular weight after irradiation is from about 50,000 to about 200,000, e.g., from about 60,000 to about 150,000 or from about 70,000 to about 125,000. However, in some embodiments, e.g., after extensive irradiation, it is possible to have a number average molecular weight of less than about 10,000 or even less than about 5,000.

In some embodiments, the second material can have a level of oxidation ($O_2$) that is higher than the level of oxidation ($O_1$) of the first material. A higher level of oxidation of the material can aid in its dispersability, swellability and/or solubility, further enhancing the material's susceptibility to chemical, enzymatic or biological attack. In some embodiments, to increase the level of the oxidation of the second material relative to the first material, the irradiation is performed under an oxidizing environment, e.g., under a blanket of air or oxygen, producing a second material that is more oxidized than the first material. For example, the second material can have more hydroxyl groups, aldehyde groups, ketone groups, ester groups or carboxylic acid groups, which can increase its hydrophilicity.

Ionizing Radiation

Each form of radiation ionizes the carbon-containing material via particular interactions, as determined by the energy of the radiation. Heavy charged particles primarily ionize matter via Coulomb scattering; furthermore, these interactions produce energetic electrons that may further ionize matter. Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, neptunium, curium, californium, americium, and plutonium.

When particles are utilized, they can be neutral (uncharged), positively charged or negatively charged. When charged, the charged particles can bear a single positive or negative charge, or multiple charges, e.g., one, two, three or even four or more charges. In instances in which chain scission is desired, positively charged particles may be desirable, in part due to their acidic nature. When particles are utilized, the particles can have the mass of a resting electron, or greater, e.g., 500, 1000, 1500, 2000, 10,000 or even 100,000 times the mass of a resting electron. For example, the particles can have a mass of from about 1 atomic unit to about 150 atomic units, e.g., from about 1 atomic unit to about 50 atomic units, or from about 1 to about 25, e.g., 1, 2, 3, 4, 5, 10, 12 or 15 amu. Accelerators used to accelerate the particles can be electrostatic DC, electrodynamic DC, RF linear, magnetic induction linear or continuous wave. For example, cyclotron type accelerators are available from IBA, Belgium, such as the Rhodotron® system, while DC type accelerators are available from RDI, now IBA Industrial, such as the Dynamitron®. Ions and ion accelerators are discussed in Introductory Nuclear Physics, Kenneth S. Krane, John Wiley & Sons, Inc. (1988), Krsto Prelec, FIZIKA B 6 (1997) 4, 177-206, Chu, William T., "Overview of Light-Ion Beam Therapy" Columbus-Ohio, ICRU-IAEA Meeting, 18-20 Mar. 2006, Iwata, Y. et al., "Alternating-Phase-Focused IH-DTL for Heavy-Ion Medical Accelerators" Proceedings of EPAC 2006, Edinburgh, Scotland and Leaner, C. M. et al., "Status of the Superconducting ECR Ion Source Venus" Proceedings of EPAC 2000, Vienna, Austria.

Gamma radiation has the advantage of a significant penetration depth into a variety of materials. Sources of gamma rays include radioactive nuclei, such as isotopes of cobalt, calcium, technicium, chromium, gallium, indium, iodine, iron, krypton, samarium, selenium, sodium, thalium, and xenon.

Sources of x rays include electron beam collision with metal targets, such as tungsten or molybdenum or alloys, or compact light sources, such as those produced commercially by Lyncean.

Sources for ultraviolet radiation include deuterium or cadmium lamps.

Sources for infrared radiation include sapphire, zinc, or selenide window ceramic lamps.

Sources for microwaves include klystrons, Slevin type RF sources, or atom beam sources that employ hydrogen, oxygen, or nitrogen gases.

In some embodiments, a beam of electrons is used as the radiation source. A beam of electrons has the advantages of high dose rates (e.g., 1, 5, or even 10 Mrad per second), high throughput, less containment, and less confinement equipment. Electrons can also be more efficient at causing chain scission. In addition, electrons having energies of 4-10 MeV can have a penetration depth of 5 to 30 mm or more, such as 40 mm.

Electron beams can be generated, e.g., by electrostatic generators, cascade generators, transformer generators, low energy accelerators with a scanning system, low energy accelerators with a linear cathode, linear accelerators, and pulsed accelerators. Electrons as an ionizing radiation source can be useful, e.g., for relatively thin sections of material, e.g., less than 0.5 inch, e.g., less than 0.4 inch, 0.3 inch, 0.2 inch, or less than 0.1 inch. In some embodiments, the energy of each electron of the electron beam is from about 0.3 MeV to about 2.0 MeV (million electron volts), e.g., from about 0.5 MeV to about 1.5 MeV, or from about 0.7 MeV to about 1.25 MeV.

Electron beam irradiation devices may be procured commercially from Ion Beam Applications, Louvain-la-Neuve, Belgium or the Titan Corporation, San Diego, Calif. Typical electron energies can be 1 MeV, 2 MeV, 4.5 MeV, 7.5 MeV, or 10 MeV. Typical electron beam irradiation device power can be 1 kW, 5 kW, 10 kW, 20 kW, 50 kW, 100 kW, 250 kW, or 500 kW. The level of depolymerization of the feedstock depends on the electron energy used and the dose applied, while exposure time depends on the power and dose. Typical doses may take values of 1 kGy, 5 kGy, 10 kGy, 20 kGy, 50 kGy, 100 kGy, or 200 kGy.

Ion Particle Beams

Particles heavier than electrons can be utilized to irradiate any of the biomass materials described herein. For example, protons, helium nuclei, argon ions, silicon ions, neon ions carbon ions, phoshorus ions, oxygen ions or nitrogen ions can be utilized. In some embodiments, particles heavier than electrons can induce higher amounts of chain scission (relative to lighter particles). In some instances, positively charged particles can induce higher amounts of chain scission than negatively charged particles due to their acidity.

Heavier particle beams can be generated, e.g., using linear accelerators or cyclotrons. In some embodiments, the energy of each particle of the beam is from about 1.0 MeV/atomic unit to about 6,000 MeV/atomic unit, e.g., from about 3 MeV/atomic unit to about 4,800 MeV/atomic unit, or from about 10 MeV/atomic unit to about 1,000 MeV/atomic unit.

In certain embodiments, ion beams used to irradiate carbon-containing materials, e.g., biomass materials, can include more than one type of ion. For example, ion beams can include mixtures of two or more (e.g., three, four or more) different types of ions. Exemplary mixtures can include carbon ions and protons, carbon ions and oxygen ions, nitrogen ions and protons, and iron ions and protons. More generally, mixtures of any of the ions discussed above (or any other ions) can be used to form irradiating ion beams. In particular, mixtures of relatively light and relatively heavier ions can be used in a single ion beam.

In some embodiments, ion beams for irradiating materials include positively-charged ions. The positively charged ions can include, for example, positively charged hydrogen ions (e.g., protons), noble gas ions (e.g., helium, neon, argon), carbon ions, nitrogen ions, oxygen ions, silicon atoms, phosphorus ions, and metal ions such as sodium ions, calcium ions, and/or iron ions. Without wishing to be bound by any theory, it is believed that such positively-charged ions behave chemically as Lewis acid moieties when exposed to materials, initiating and sustaining cationic ring-opening chain scission reactions in an oxidative environment.

In certain embodiments, ion beams for irradiating materials include negatively-charged ions. Negatively charged ions can include, for example, negatively charged hydrogen ions (e.g., hydride ions), and negatively charged ions of various relatively electronegative nuclei (e.g., oxygen ions, nitrogen ions, carbon ions, silicon ions, and phosphorus ions). Without wishing to be bound by any theory, it is believed that such negatively-charged ions behave chemically as Lewis base moieties when exposed to materials, causing anionic ring-opening chain scission reactions in a reducing environment.

In some embodiments, beams for irradiating materials can include neutral atoms. For example, any one or more of hydrogen atoms, helium atoms, carbon atoms, nitrogen atoms, oxygen atoms, neon atoms, silicon atoms, phosphorus atoms, argon atoms, and iron atoms can be included in beams that are used for irradiation of biomass materials. In general, mixtures of any two or more of the above types of atoms (e.g., three or more, four or more, or even more) can be present in the beams.

In certain embodiments, ion beams used to irradiate materials include singly-charged ions such as one or more of $H^+$, $H^-$, $He^+$, $Ne^+$, $Ar^+$, $C^+$, $C^-$, $O^+$, $O^-$, $N^+$, $N^-$, $Si^+$, $Si^-$, $P^+$, $P^-$, $Na^+$, $Ca^+$, and $Fe^+$. In some embodiments, ion beams can include multiply-charged ions such as one or more of $C^{2+}$, $C^{3+}$, $C^{4+}$, $N^{3+}$, $N^{5+}$, $N^{3-}$, $O^{2+}$, $O^{2-}$, $O_2^{2-}$, $Si^{2+}$, $Si^{4+}$, $Si^{2-}$, and $Si^{4-}$. In general, the ion beams can also include more complex polynuclear ions that bear multiple positive or negative charges. In certain embodiments, by virtue of the structure of the polynuclear ion, the positive or negative charges can be effectively distributed over substantially the entire structure of the ions. In some embodiments, the positive or negative charges can be somewhat localized over portions of the structure of the ions.

Electromagnetic Radiation

In embodiments in which the irradiating is performed with electromagnetic radiation, the electromagnetic radiation can have, e.g., energy per photon (in electron volts) of greater than $10^2$ eV, e.g., greater than $10^3$, $10^4$, $10^5$, $10^6$, or even greater than $10^7$ eV. In some embodiments, the electromagnetic radiation has energy per photon of between $10^4$ and $10^7$, e.g., between $10^5$ and $10^6$ eV. The electromagnetic radiation can have a frequency of, e.g., greater than $10^{16}$ hz, greater than $10^{17}$ hz, $10^{18}$, $10^{19}$, $10^{20}$, or even greater than $10^{21}$ hz. In some embodiments, the electromagnetic radiation has a frequency of between $10^{18}$ and $10^{22}$ hz, e.g., between $10^{19}$ to $10^{21}$ hz.

Quenching and Controlled Functionalization of Biomass

After treatment with ionizing radiation, any of the materials or mixtures described herein may become ionized; that is, the treated material may include radicals at levels that are detectable with an electron spin resonance spectrometer. If ionized biomass remains in the atmosphere, it will be oxidized, such as to an extent that carboxylic acid groups are generated by reacting with the atmospheric oxygen. In some instances with some materials, such oxidation is desired because it can aid in the further breakdown in molecular weight of the carbohydrate-containing biomass, and the oxidation groups, e.g., carboxylic acid groups can be helpful for solubility and microorganism utilization in some instances. However, since the radicals can "live" for some time after irradiation, e.g., longer than 1 day, 5 days, 30 days, 3 months, 6 months or even longer than 1 year, material properties can continue to change over time, which in some instances, can be undesirable. Thus, it may be desirable to quench the ionized material.

After ionization, any biomass material that has been ionized can be quenched to reduce the level of radicals in the ionized biomass, e.g., such that the radicals are no longer detectable with the electron spin resonance spectrometer. For example, the radicals can be quenched by the application of a sufficient pressure to the biomass and/or by utilizing a fluid in contact with the ionized biomass, such as a gas or liquid, that reacts with (quenches) the radicals. Using a gas or liquid to at least aid in the quenching of the radicals can be used to functionalize the ionized biomass with a desired amount and kind of functional groups, such as carboxylic acid groups, enol groups, aldehyde groups, nitro groups, nitrile groups, amino groups, alkyl amino groups, alkyl groups, chloroalkyl groups or chlorofluoroalkyl groups.

In some instances, such quenching can improve the stability of some of the ionized biomass materials. For example, quenching can improve the resistance of the biomass to oxidation. Functionalization by quenching can also improve the solubility of any biomass described herein, can improve its thermal stability, and can improve material utilization by various microorganisms. For example, the functional groups imparted to the biomass material by the quenching can act as receptor sites for attachment by microorganisms, e.g., to enhance cellulose hydrolysis by various microorganisms.

In some embodiments, quenching includes an application of pressure to the biomass, such as by mechanically deforming the biomass, e.g., directly mechanically compressing the biomass in one, two, or three dimensions, or applying pressure to a fluid in which the biomass is immersed, e.g., isostatic pressing. In such instances, the deformation of the material itself brings radicals, which are often trapped in crystalline domains, in close enough proximity so that the radicals can recombine, or react with another group. In some instances, the pressure is applied together with the application of heat, such as a sufficient quantity of heat to elevate the temperature of the biomass to above a melting point or softening point of a component of the biomass, such as lignin, cellulose or hemicellulose. Heat can improve molecular mobility in the material, which can aid in the quenching of the radicals. When pressure is utilized to quench, the pressure can be greater than about 1000 psi, such as greater than about 1250 psi, 1450 psi, 3625 psi, 5075 psi, 7250 psi, 10000 psi or even greater than 15000 psi.

In some embodiments, quenching includes contacting the biomass with a fluid, such as a liquid or gas, e.g., a gas capable of reacting with the radicals, such as acetylene or a mixture of acetylene in nitrogen, ethylene, chlorinated ethylenes or chlorofluoroethylenes, propylene or mixtures of these gases. In other particular embodiments, quenching includes contacting the biomass with a liquid, e.g., a liquid soluble in, or at least capable of penetrating into the biomass and reacting with the radicals, such as a diene, such as 1,5-cyclooctadiene. In some specific embodiments, quenching includes contacting the biomass with an antioxidant, such as Vitamin E. If desired, the biomass feedstock can include an antioxidant dispersed therein, and the quenching can come from contacting the antioxidant dispersed in the biomass feedstock with the radicals.

Functionalization can be enhanced by utilizing heavy charged ions, such as any of the heavier ions described herein. For example, if it is desired to enhance oxidation, charged oxygen ions can be utilized for the irradiation. If nitrogen functional groups are desired, nitrogen ions or anions that include nitrogen can be utilized. Likewise, if sulfur or phosphorus groups are desired, sulfur or phosphorus ions can be used in the irradiation.

Doses

In some instances, the irradiation is performed at a dosage rate of greater than about 0.25 Mrad per second, e.g., greater than about 0.5, 0.75, 1.0, 1.5, 2.0, or even greater than about 2.5 Mrad per second. In some embodiments, the irradiating is performed at a dose rate of between 5.0 and 1500.0 kilorads/hour, e.g., between 10.0 and 750.0 kilorads/hour or between 50.0 and 350.0 kilorads/hour.

In some embodiments, the irradiating (with any radiation source or a combination of sources) is performed until the material receives a dose of at least 0.1 Mrad, at least 0.25 Mrad, e.g., at least 1.0 Mrad, at least 2.5 Mrad, at least 5.0 Mrad, at least 10.0 Mrad, at least 60 Mrad or at least 100 Mrad. In some embodiments, the irradiating is performed until the material receives a dose of from about 0.1 Mrad to about 500 Mrad, from about 0.5 Mrad to about 200 Mrad, from about 1 Mrad to about 100 Mrad, or from about 5 Mrad to about 60 Mrad. In some embodiments, a relatively low dose of radiation is applied, e.g., less than 60 Mrad.

Sonication

Sonication can reduce the molecular weight and/or crystallinity of materials, such as one or more of any of the materials described herein, e.g., one or more carbohydrate sources, such as cellulosic or lignocellulosic materials, or starchy materials. Sonication can also be used to sterilize the materials.

In one method, a first material that includes cellulose having a first number average molecular weight ($M_{N1}$) is dispersed in a medium, such as water, and sonicated and/or otherwise cavitated, to provide a second material that includes cellulose having a second number average molecular weight ($M_{N2}$) lower than the first number average molecular weight. The second material (or the first and second material in certain embodiments) can be combined with a microorganism (with or without enzyme treatment) that can utilize the second and/or first material to produce an intermediate or product.

Since the second material includes cellulose having a reduced molecular weight relative to the first material, and in some instances, a reduced crystallinity as well, the second material is generally more dispersible, swellable, and/or soluble, e.g., in a solution containing a microorganism.

In some embodiments, the second number average molecular weight ($M_{N2}$) is lower than the first number average molecular weight ($M_{N1}$) by more than about 10 percent, e.g., more than about 15, 20, 25, 30, 35, 40, 50 percent, 60 percent, or even more than about 75 percent.

In some instances, the second material includes cellulose that has a crystallinity ($C_2$) that is lower than the crystallinity ($C_{N1}$) of the cellulose of the first material. For example, ($C_2$) can be lower than ($C_{N1}$) by more than about 10 percent, e.g., more than about 15, 20, 25, 30, 35, 40, or even more than about 50 percent.

In some embodiments, the starting crystallinity index (prior to sonication) is from about 40 to about 87.5 percent, e.g., from about 50 to about 75 percent or from about 60 to about 70 percent, and the crystallinity index after sonication is from about 10 to about 50 percent, e.g., from about 15 to about 45 percent or from about 20 to about 40 percent. However, in certain embodiments, e.g., after extensive sonication, it is possible to have a crystallinity index of lower than 5 percent. In some embodiments, the material after sonication is substantially amorphous.

In some embodiments, the starting number average molecular weight (prior to sonication) is from about 200,000 to about 3,200,000, e.g., from about 250,000 to about 1,000,000 or from about 250,000 to about 700,000, and the number average molecular weight after sonication is from about 50,000 to about 200,000, e.g., from about 60,000 to about 150,000 or from about 70,000 to about 125,000. However, in some embodiments, e.g., after extensive sonication, it is possible to have a number average molecular weight of less than about 10,000 or even less than about 5,000.

In some embodiments, the second material can have a level of oxidation ($O_2$) that is higher than the level of oxidation ($O_1$) of the first material. A higher level of oxidation of the material can aid in its dispersability, swellability and/or solubility, further enhancing the material's susceptibility to chemical, enzymatic or microbial attack. In some embodiments, to increase the level of the oxidation of the second material relative to the first material, the sonication is performed in an oxidizing medium, producing a second material that is more oxidized than the first material. For example, the second material can have more hydroxyl groups, aldehyde groups, ketone groups, ester groups or carboxylic acid groups, which can increase its hydrophilicity.

In some embodiments, the sonication medium is an aqueous medium. If desired, the medium can include an oxidant, such as a peroxide (e.g., hydrogen peroxide), a dispersing agent and/or a buffer. Examples of dispersing agents include ionic dispersing agents, e.g., sodium lauryl sulfate, and non-ionic dispersing agents, e.g., poly(ethylene glycol).

In other embodiments, the sonication medium is non-aqueous. For example, the sonication can be performed in a hydrocarbon, e.g., toluene or heptane, an ether, e.g., diethyl ether or tetrahydrofuran, or even in a liquefied gas such as argon, xenon, or nitrogen.

Pyrolysis

One or more pyrolysis processing sequences can be used to physically treat the biomass material. Pyrolysis can also be used to sterilize the material.

In one example, a first material that includes cellulose having a first number average molecular weight ($M_{N1}$) is pyrolyzed, e.g., by heating the first material in a tube furnace (in the presence or absence of oxygen), to provide a second material that includes cellulose having a second number average molecular weight ($M_{N2}$) lower than the first number average molecular weight.

Since the second material includes cellulose having a reduced molecular weight relative to the first material, and in some instances, a reduced crystallinity as well, the second material is generally more dispersible, swellable and/or soluble, e.g., in a solution containing a microorganism.

In some embodiments, the second number average molecular weight ($M_{N2}$) is lower than the first number average molecular weight ($M_{N1}$) by more than about 10 percent, e.g., more than about 15, 20, 25, 30, 35, 40, 50 percent, 60 percent, or even more than about 75 percent.

In some instances, the second material includes cellulose that has a crystallinity ($C_2$) that is lower than the crystallinity ($C_{N1}$) of the cellulose of the first material. For example, ($C_2$) can be lower than ($C_{N1}$) by more than about 10 percent, e.g., more than about 15, 20, 25, 30, 35, 40, or even more than about 50 percent.

In some embodiments, the starting crystallinity (prior to pyrolysis) is from about 40 to about 87.5 percent, e.g., from about 50 to about 75 percent or from about 60 to about 70 percent, and the crystallinity index after pyrolysis is from about 10 to about 50 percent, e.g., from about 15 to about 45 percent or from about 20 to about 40 percent. However, in certain embodiments, e.g., after extensive pyrolysis, it is possible to have a crystallinity index of lower than 5 percent. In some embodiments, the material after pyrolysis is substantially amorphous.

In some embodiments, the starting number average molecular weight (prior to pyrolysis) is from about 200,000 to about 3,200,000, e.g., from about 250,000 to about 1,000,000 or from about 250,000 to about 700,000, and the number average molecular weight after pyrolysis is from about 50,000 to about 200,000, e.g., from about 60,000 to about 150,000 or from about 70,000 to about 125,000. However, in some embodiments, e.g., after extensive pyrolysis, it is possible to have a number average molecular weight of less than about 10,000 or even less than about 5,000.

In some embodiments, the second material can have a level of oxidation ($O_2$) that is higher than the level of oxidation ($O_1$) of the first material. A higher level of oxidation of the material can aid in its dispersability, swellability and/or solubility, further enhancing the susceptibility of the material to chemical, enzymatic or microbial attack. In some embodiments, to increase the level of the oxidation of the second material relative to the first material, the pyrolysis is performed in an oxidizing environment, producing a second material that is more oxidized than the first material. For example, the second material can have more hydroxyl groups, aldehyde groups, ketone groups, ester groups or carboxylic acid groups, than the first material, thereby increasing the hydrophilicity of the material.

In some embodiments, the pyrolysis of the materials is continuous. In other embodiments, the material is pyrolyzed for a pre-determined time, and then allowed to cool for a second pre-determined time before pyrolyzing again.

Oxidation

One or more oxidative processing sequences can be used to physically treat the biomass material. The oxidation conditions can be varied, e.g., depending on the lignin content of the feedstock, with a higher degree of oxidation generally being desired for higher lignin content feedstocks.

In one method, a first material that includes cellulose having a first number average molecular weight ($M_{N1}$) and having a first oxygen content ($O_1$) is oxidized, e.g., by heating the first material in a stream of air or oxygen-enriched air, to provide a second material that includes cellulose having a second number average molecular weight ($M_{N2}$) and having a second oxygen content ($O_2$) higher than the first oxygen content ($O_1$).

The second number average molecular weight of the second material is generally lower than the first number average molecular weight of the first material. For example, the molecular weight may be reduced to the same extent as discussed above with respect to the other physical treatments. The crystallinity of the second material may also be reduced to the same extent as discussed above with respect to the other physical treatments.

In some embodiments, the second oxygen content is at least about five percent higher than the first oxygen content, e.g., 7.5 percent higher, 10.0 percent higher, 12.5 percent higher, 15.0 percent higher or 17.5 percent higher. In some preferred embodiments, the second oxygen content is at least about 20.0 percent higher than the first oxygen content of the first material. Oxygen content is measured by elemental analysis by pyrolyzing a sample in a furnace operating at 1300° C. or higher. A suitable elemental analyzer is the LECO CHNS-932 analyzer with a VTF-900 high temperature pyrolysis furnace.

Generally, oxidation of a material occurs in an oxidizing environment. For example, the oxidation can be effected or aided by pyrolysis in an oxidizing environment, such as in air or argon enriched in air. To aid in the oxidation, various chemical agents, such as oxidants, acids or bases can be added to the material prior to or during oxidation. For example, a peroxide (e.g., benzoyl peroxide) can be added prior to oxidation.

Some oxidative methods of reducing recalcitrance in a biomass feedstock employ Fenton-type chemistry. Such methods are disclosed, for example, in U.S. Ser. No. 12/639, 289, the complete disclosure of which is incorporated herein by reference.

Exemplary oxidants include peroxides, such as hydrogen peroxide and benzoyl peroxide, persulfates, such as ammonium persulfate, activated forms of oxygen, such as ozone, permanganates, such as potassium permanganate, perchlorates, such as sodium perchlorate, and hypochlorites, such as sodium hypochlorite (household bleach).

In some situations, pH is maintained at or below about 5.5 during contact, such as between 1 and 5, between 2 and 5, between 2.5 and 5 or between about 3 and 5. Oxidation conditions can also include a contact period of between 2 and 12 hours, e.g., between 4 and 10 hours or between 5 and 8 hours. In some instances, temperature is maintained at or below 300° C., e.g., at or below 250, 200, 150, 100 or 50° C. In some instances, the temperature remains substantially ambient, e.g., at or about 20-25° C.

In some embodiments, the one or more oxidants are applied as a gas, such as by generating ozone in-situ by irradiating the material through air with a beam of particles, such as electrons.

In some embodiments, the mixture further includes one or more hydroquinones, such as 2,5-dimethoxyhydroquinone (DMHQ) and/or one or more benzoquinones, such as 2,5-dimethoxy-1,4-benzoquinone (DMBQ), which can aid in electron transfer reactions.

In some embodiments, the one or more oxidants are electrochemically-generated in-situ. For example, hydrogen peroxide and/or ozone can be electro-chemically produced within a contact or reaction vessel.

Other Processes to Functionalize

Any of the processes of this paragraph can be used alone without any of the processes described herein, or in combination with any of the processes described herein (in any order): steam explosion, chemical treatment (e.g., acid treatment (including concentrated and dilute acid treatment with mineral acids, such as sulfuric acid, hydrochloric acid and organic acids, such as trifluoroacetic acid) and/or base treatment (e.g., treatment with lime or sodium hydroxide)), UV treatment, screw extrusion treatment (see, e.g., U.S. Patent Application Ser. No. 61/115,398, filed Nov. 17, 2008, solvent treatment (e.g., treatment with ionic liquids) and freeze milling (see, e.g., U.S. Ser. No. 12/502,629).

Fermentation

Microorganisms can produce a number of useful intermediates and products, such as those described herein, by fermenting a low molecular weight sugar in the presence of the functionalized biomass materials. For example, fermentation or other bioprocesses can produce alcohols, organic acids, hydrocarbons, hydrogen, proteins or mixtures of any of these materials.

The microorganism can be a natural microorganism or an engineered microorganism. For example, the microorganism can be a bacterium, e.g., a cellulolytic bacterium, a fungus, e.g., a yeast, a plant or a protist, e.g., an algae, a protozoa or a fungus-like protist, e.g., a slime mold. When the organisms are compatible, mixtures of organisms can be utilized.

Suitable fermenting microorganisms have the ability to convert carbohydrates, such as glucose, xylose, arabinose, mannose, galactose, oligosaccharides or polysaccharides into fermentation products. Fermenting microorganisms include strains of the genus *Saccharomyces* spp. e.g., *Saccharomyces cerevisiae* (baker's yeast), *Saccharomyces distaticus, Saccharomyces uvarum*; the genus *Kluyveromyces*, e.g., species *Kluyveromyces marxianus, Kluyveromyces fragilis*; the genus *Candida*, e.g., *Candida pseudotropicalis*, and *Candida brassicae, Pichia stipitis* (a relative of *Candida shehatae*, the genus *Clavispora*, e.g., species *Clavispora lusitaniae* and *Clavispora opuntiae*, the genus *Pachysolen*, e.g., species *Pachysolen tannophilus*, the genus *Bretannomyces*, e.g., species *Bretannomyces clausenii* (Philippidis, G. P., 1996, Cellulose bioconversion technology, in Handbook on Bioethanol: Production and Utilization, Wyman, C. E., ed., Taylor & Francis, Washington, D.C., 179-212).

Commercially available yeasts include, for example, Red Star®/Lesaffre Ethanol Red (available from Red Star/Lesaffre, USA), FALI® (available from Fleischmann's Yeast, a division of Burns Philip Food Inc., USA), SUPERSTART® (available from Alltech, now Lalemand), GERT STRAND® (available from Gert Strand AB, Sweden) and FERMOL® (available from DSM Specialties).

Bacteria may also be used in fermentation, e.g., *Zymomonas mobilis* and *Clostridium thermocellum* (Philippidis, 1996, supra).

The optimum pH for yeast is from about pH 4 to 5, while the optimum pH for *Zymomonas* bacteria is from about pH 5 to 6. Typical fermentation times are about 24 to 96 hours with temperatures in the range of 26° C. to 40° C., however thermophilic microorganisms prefer higher temperatures.

In some embodiments, all or a portion of the fermentation process can be interrupted before the low molecular weight sugar is completely converted to ethanol. The intermediate fermentation products include high concentrations of sugar and carbohydrates. These intermediate fermentation products can be used in preparation of food for human or animal consumption. Additionally or alternatively, the intermediate fermentation products can be ground to a fine particle size in a stainless-steel laboratory mill to produce a flour-like substance.

Mobile fermentors can be utilized, as described in U.S. Provisional Patent Application Ser. 60/832,735, now Published International Application No. WO 2008/011598.

Post-Processing

Distillation

After fermentation, the resulting fluids can be distilled using, for example, a "beer column" to separate ethanol and other alcohols from the majority of water and residual solids. The vapor exiting the beer column can be, e.g., 35% by weight ethanol and can be fed to a rectification column. A mixture of nearly azeotropic (92.5%) ethanol and water from the rectification column can be purified to pure (99.5%) ethanol using vapor-phase molecular sieves. The beer column bottoms can be sent to the first effect of a three-effect evaporator. The rectification column reflux condenser can provide heat for this first effect. After the first effect, solids can be separated using a centrifuge and dried in a rotary dryer. A portion (25%) of the centrifuge effluent can be recycled to fermentation and the rest sent to the second and third evaporator effects. Most of the evaporator condensate can be returned to the process as fairly clean condensate with a small portion split off to waste water treatment to prevent build-up of low-boiling compounds.

Intermediates and Products

The processes described herein can be used to produce one or more intermediates or products, such as energy, fuels, foods and materials. Specific examples of products include, but are not limited to, hydrogen, alcohols (e.g., monohydric alcohols or dihydric alcohols, such as ethanol, n-propanol or n-butanol), hydrated or hydrous alcohols, e.g., containing greater than 10%, 20%, 30% or even greater than 40% water, xylitol, sugars, biodiesel, organic acids (e.g., acetic acid and/or lactic acid), hydrocarbons, co-products (e.g., proteins, such as cellulolytic proteins (enzymes) or single cell proteins), and mixtures of any of these in any combination or relative concentration, and optionally in combination with any additives, e.g., fuel additives. Other examples include carboxylic acids, such as acetic acid or butyric acid, salts of a carboxylic acid, a mixture of carboxylic acids and salts of carboxylic acids and esters of carboxylic acids (e.g., methyl, ethyl and n-propyl esters), ketones (e.g., acetone), aldehydes (e.g., acetaldehyde), alpha, beta unsaturated acids, such as acrylic acid and olefins, such as ethylene. Other alcohols and alcohol derivatives include propanol, propylene glycol, 1,4-butanediol, 1,3-propanediol, methyl or ethyl esters of any of these alcohols. Other products include methyl acrylate, methylmethacrylate, lactic acid, propionic acid, butyric acid, succinic acid, 3-hydroxypropionic acid, a salt of any of the acids and a mixture of any of the acids and respective salts.

Other intermediates and products, including food and pharmaceutical products, are described in U.S. Ser. No. 12/417,900, the full disclosure of which is hereby incorporated by reference herein.

EXAMPLES

The following Examples are intended to illustrate, and do not limit the teachings of this disclosure.

Example 1

Preparation of Fibrous Material from Polycoated Paper

A 1500 pound skid of virgin, half-gallon juice cartons made of un-printed polycoated white Kraft board having a bulk density of 20 lb/ft$^3$ was obtained from International Paper. Each carton was folded flat, and then fed into a 3 hp Flinch Baugh shredder at a rate of approximately 15 to 20 pounds per hour. The shredder was equipped with two 12 inch rotary blades, two fixed blades and a 0.30 inch discharge screen. The gap between the rotary and fixed blades was adjusted to 0.10 inch. The output from the shredder resembled confetti having a width of between 0.1 inch and 0.5 inch, a length of between 0.25 inch and 1 inch and a thickness equivalent to that of the starting material (about 0.075 inch). The confetti-like material was fed to a Munson rotary knife cutter, Model SC30. Model SC30 is equipped with four rotary blades, four fixed blades, and a discharge screen having ⅛ inch openings. The gap between the rotary and fixed blades was set to approximately 0.020 inch. The rotary knife cutter sheared the confetti-like pieces across the knife-edges, tearing the pieces apart and releasing a fibrous material at a rate of about one pound per hour. The fibrous material had a BET surface area of 0.9748 m$^2$/g+/−0.0167 m$^2$/g, a porosity of 89.0437 percent and a bulk density (@0.53 psia) of 0.1260 g/mL. An average length of the fibers was 1.141 mm and an average width of the fibers was 0.027 mm, giving an average L/D of 42:1.

Example 2

Preparation of Fibrous Material from Bleached Kraft Board

A 1500 pound skid of virgin bleached white Kraft board having a bulk density of 30 lb/ft$^3$ was obtained from International Paper. The material was folded flat, and then fed into a 3 hp Flinch Baugh shredder at a rate of approximately 15 to 20 pounds per hour. The shredder was equipped with two 12 inch rotary blades, two fixed blades and a 0.30 inch discharge screen. The gap between the rotary and fixed blades was adjusted to 0.10 inch. The output from the shredder resembled confetti having a width of between 0.1 inch and 0.5 inch, a length of between 0.25 inch and 1 inch and a thickness equivalent to that of the starting material (about 0.075 inch). The confetti-like material was fed to a Munson rotary knife cutter, Model SC30. The discharge screen had ⅛ inch openings. The gap between the rotary and fixed blades was set to approximately 0.020 inch. The rotary knife cutter sheared the confetti-like pieces, releasing a fibrous material at a rate of about one pound per hour. The fibrous material had a BET surface area of 1.1316 m$^2$/g+/−0.0103 m$^2$/g, a porosity of 88.3285 percent and a bulk density (@0.53 psia) of 0.1497 g/mL. An average length of the fibers was 1.063 mm and an average width of the fibers was 0.0245 mm, giving an average L/D of 43:1.

Example 3

Preparation of Twice Sheared Fibrous Material from Bleached Kraft Board

A 1500 pound skid of virgin bleached white Kraft board having a bulk density of 30 lb/ft$^3$ was obtained from International Paper. The material was folded flat, and then fed into a 3 hp Flinch Baugh shredder at a rate of approximately 15 to 20 pounds per hour. The shredder was equipped with two 12 inch rotary blades, two fixed blades and a 0.30 inch discharge screen. The gap between the rotary and fixed blades was adjusted to 0.10 inch. The output from the shredder resembled confetti (as above). The confetti-like material was fed to a Munson rotary knife cutter, Model SC30. The discharge screen had 1/16 inch openings. The gap between the rotary and fixed blades was set to approximately 0.020 inch. The rotary knife cutter the confetti-like pieces, releasing a fibrous material at a rate of about one pound per hour. The material resulting from the first shearing was fed back into the same setup described above and sheared again. The resulting fibrous material had a BET surface area of 1.4408 $m^2/g$ +/- 0.0156 $m^2/g$, a porosity of 90.8998 percent and a bulk density (@0.53 psia) of 0.1298 g/mL. An average length of the fibers was 0.891 mm and an average width of the fibers was 0.026 mm, giving an average L/D of 34:1.

Example 4

Preparation of Thrice Sheared Fibrous Material from Bleached Kraft Board

A 1500 pound skid of virgin bleached white Kraft board having a bulk density of 30 lb/$ft^3$ was obtained from International Paper. The material was folded flat, and then fed into a 3 hp Flinch Baugh shredder at a rate of approximately 15 to 20 pounds per hour. The shredder was equipped with two 12 inch rotary blades, two fixed blades and a 0.30 inch discharge screen. The gap between the rotary and fixed blades was adjusted to 0.10 inch. The output from the shredder resembled confetti (as above). The confetti-like material was fed to a Munson rotary knife cutter, Model SC30. The discharge screen had ⅛ inch openings. The gap between the rotary and fixed blades was set to approximately 0.020 inch. The rotary knife cutter sheared the confetti-like pieces across the knife-edges. The material resulting from the first shearing was fed back into the same setup and the screen was replaced with a 1/16 inch screen. This material was sheared. The material resulting from the second shearing was fed back into the same setup and the screen was replaced with a 1/32 inch screen. This material was sheared. The resulting fibrous material had a BET surface area of 1.6897 $m^2/g$ +/- 0.0155 $m^2/g$, a porosity of 87.7163 percent and a bulk density (@0.53 psia) of 0.1448 g/mL. An average length of the fibers was 0.824 mm and an average width of the fibers was 0.0262 mm, giving an average L/D of 32:1.

Example 5

Electron Beam Processing

Samples were treated with electron beam using a vaulted Rhodotron® TT200 continuous wave accelerator delivering 5 MeV electrons at 80 kW of output power. Table 1 describes the parameters used. Table 2 reports the nominal dose used for the Sample ID (in Mrad) and the corresponding dose delivered to the sample (in kgy).

TABLE 1

| Rhodotron ® TT 200 Parameters | |
|---|---|
| Beam | |
| Beam Produced: | Accelerated electrons |
| Beam energy: | Nominal (fixed): 10 MeV (+0 keV-250 keV |
| Energy dispersion at 10 Mev: | Full width half maximum (FWHM) 300 keV |
| Beam power at 10 MeV: | Guaranteed Operating Range 1 to 80 kW |
| Power Consumption | |
| Stand-by condition (vacuum and cooling ON): | <15 kW |
| At 50 kW beam power: | <210 kW |
| At 80 kW beam power: | <260 kW |

TABLE 1-continued

| Rhodotron ® TT 200 Parameters | |
|---|---|
| RF System | |
| Frequency: | 107.5 ± 1 MHz |
| Tetrode type: | Thomson TH781 |
| Scanning Horn | |
| Nominal Scanning Length (measured at 25-35 cm from window): | 120 cm |
| Scanning Range: | From 30% to 100% of Nominal Scanning Length |
| Nominal Scanning Frequency (at max. scanning length): | 100 Hz ± 5% |
| Scanning Uniformity (across 90% of Nominal Scanning Length) | ±5% |

TABLE 2

Dosages Delivered to Samples

| Total Dosage (MRad) (Number Associated with Sample ID | Delivered Dose (kgy)[1] |
|---|---|
| 1 | 9.9 |
| 3 | 29.0 |
| 5 | 50.4 |
| 7 | 69.2 |
| 10 | 100.0 |
| 15 | 150.3 |
| 20 | 198.3 |
| 30 | 330.9 |
| 50 | 529.0 |
| 70 | 695.9 |
| 100 | 993.6 |

[1] For example, 9.9 kgy was delivered in 11 seconds at a beam current of 5 mA and a line speed of 12.9 feet/minute. Cool time between treatments was around 2 minutes.

Example 6

Methods of Determining Molecular Weight of Cellulosic and Lignocellulosic Materials by Gel Permeation Chromatography Cellulosic and lignocellulosic materials for analysis were treated according to Example 4. Sample materials presented in the following tables include Kraft paper (P), wheat straw (WS), alfalfa (A), cellulose (C), switchgrass (SG), grasses (G), and starch (ST), and sucrose (S). The number "132" of the Sample ID refers to the particle size of the material after shearing through a 1/32 inch screen. The number after the dash refers to the dosage of radiation (MRad) and "US" refers to ultrasonic treatment. For example, a sample ID "P132-10" refers to Kraft paper that has been sheared to a particle size of 132 mesh and has been irradiated with 10 Mrad.

For samples that were irradiated with e-beam, the number following the dash refers to the amount of energy delivered to the sample. For example, a sample ID "P-100e" refers to Kraft paper that has been delivered a dose of energy of about 100 MRad or about 1000 kgy (Table 2).

TABLE 3

Peak Average Molecular Weight of Irradiated Kraft Paper

| Sample Source | Sample ID | Dosage[1] (MRad) | Ultrasound[2] | Average MW ± Std Dev. |
|---|---|---|---|---|
| Kraft Paper | P132 | 0 | No | 32853 ± 10006 |
| | P132-10 | 10 | " | 61398 ± 2468** |
| | P132-100 | 100 | " | 8444 ± 580 |
| | P132-181 | 181 | " | 6668 ± 77 |
| | P132-US | 0 | Yes | 3095 ± 1013 |

**Low doses of radiation appear to increase the molecular weight of some materials
[1]Dosage Rate = 1 MRad/hour
[2]Treatment for 30 minutes with 20 kHz ultrasound using a 1000 W horn under re-circulating conditions with the material dispersed in water.

TABLE 4

Peak Average Molecular Weight of Irradiated Kraft Paper with E-Beam

| Sample Source | Sample ID | Dosage (MRad) | Average MW ± Std Dev. |
|---|---|---|---|
| Kraft Paper | P-1e | 1 | 63489 ± 595 |
| | P-5e | 5 | 56587 ± 536 |
| | P-10e | 10 | 53610 ± 327 |
| | P-30e | 30 | 38231 ± 124 |
| | P-70e | 70 | 12011 ± 158 |
| | P-100e | 100 | 9770 ± 2 |

TABLE 5

Peak Average Molecular Weight of Gamma Irradiated Materials

| Sample ID | Peak # | Dosage[1] (MRad) | Ultrasound[2] | Average MW ± Std Dev. |
|---|---|---|---|---|
| WS132 | 1 | 0 | No | 1407411 ± 175191 |
| | 2 | " | " | 39145 ± 3425 |
| | 3 | " | " | 2886 ± 177 |
| WS132-10* | 1 | 10 | " | 26040 ± 3240 |
| WS132-100* | 1 | 100 | " | 23620 ± 453 |
| A132 | 1 | 0 | " | 1604886 ± 151701 |
| | 2 | " | " | 37525 ± 3751 |
| | 3 | " | " | 2853 ± 490 |
| A132-10* | 1 | 10 | " | 50853 ± 1665 |
| | 2 | " | " | 2461 ± 17 |
| A132-100* | 1 | 100 | " | 38291 ± 2235 |
| | 2 | " | " | 2487 ± 15 |
| SG132 | 1 | 0 | " | 1557360 ± 83693 |
| | 2 | " | " | 42594 ± 4414 |
| | 3 | " | " | 3268 ± 249 |
| SG132-10* | 1 | 10 | " | 60888 ± 9131 |
| SG132-100* | 1 | 100 | " | 22345 ± 3797 |
| SG132-10-US | 1 | 10 | Yes | 86086 ± 43518 |
| | 2 | " | " | 2247 ± 468 |
| SG132-100-US | 1 | 100 | " | 4696 ± 1465 |

*Peaks coalesce after treatment
**Low doses of radiation appear to increase the molecular weight of some materials
[1]Dosage Rate = 1 MRad/hour
[2]Treatment for 30 minutes with 20 kHz ultrasound using a 1000 W horn under re-circulating conditions with the material dispersed in water.

TABLE 6

Peak Average Molecular Weight of Irradiated Material with E-Beam

| Sample ID | Peak # | Dosage | Average MW ± STD DEV. |
|---|---|---|---|
| A-1e | 1 | 1 | 1004783 ± 97518 |
| | 2 | | 34499 ± 482 |
| | 3 | | 2235 ± 1 |
| A-5e | 1 | 5 | 38245 ± 346 |
| | 2 | | 2286 ± 35 |
| A-10e | 1 | 10 | 44326 ± 33 |
| | 2 | | 2333 ± 18 |
| A-30e | 1 | 30 | 47366 ± 583 |
| | 2 | | 2377 ± 7 |
| A-50e | 1 | 50 | 32761 ± 168 |
| | 2 | | 2435 ± 6 |
| G-1e | 1 | 1 | 447362 ± 38817 |
| | 2 | | 32165 ± 779 |
| | 3 | | 3004 ± 25 |
| G-5e | 1 | 5 | 62167 ± 6418 |
| | 2 | | 2444 ± 33 |
| G-10e | 1 | 10 | 72636 ± 4075 |
| | 2 | | 3065 ± 34 |
| G-30e | 1 | 30 | 17159 ± 390 |
| G-50e | 1 | 50 | 18960 ± 142 |
| ST | 1 | 0 | 923336 ± 1883 |
| | 2 | | 150265 ± 4033 |
| ST-1e | 1 | 1 | 846081 ± 5180 |
| | 2 | | 131222 ± 1687 |
| ST-5e | 1 | 5 | 90664 ± 1370 |
| ST-10e | 1 | 10 | 98050 ± 255 |
| ST-30e | 1 | 30 | 41884 ± 223 |
| ST-70e | 1 | 70 | 9699 ± 31 |
| ST-100e | 1 | 100 | 8705 ± 38 |

Gel Permeation Chromatography (GPC) is used to determine the molecular weight distribution of polymers. During GPC analysis, a solution of the polymer sample is passed through a column packed with a porous gel trapping small molecules. The sample is separated based on molecular size with larger molecules eluting sooner than smaller molecules. The retention time of each component is most often detected by refractive index (RI), evaporative light scattering (ELS), or ultraviolet (UV) and compared to a calibration curve. The resulting data is then used to calculate the molecular weight distribution for the sample.

A distribution of molecular weights rather than a unique molecular weight is used to characterize synthetic polymers. To characterize this distribution, statistical averages are utilized. The most common of these averages are the "number average molecular weight" ($M_n$) and the "weight average molecular weight" ($M_w$).

Methods of calculating these values are described in the art, e.g., in Example 9 of WO 2008/073186.

The polydispersity index or PI is defined as the ratio of $M_w/M_n$. The larger the PI, the broader or more disperse the distribution. The lowest value that a PI can have is 1. This represents a monodisperse sample; that is, a polymer with all of the molecules in the distribution being the same molecular weight.

The peak molecular weight value ($M_P$) is another descriptor defined as the mode of the molecular weight distribution. It signifies the molecular weight that is most abundant in the distribution. This value also gives insight to the molecular weight distribution.

Most GPC measurements are made relative to a different polymer standard. The accuracy of the results depends on how closely the characteristics of the polymer being analyzed match those of the standard used. The expected error in reproducibility between different series of determinations, calibrated separately, is ca. 5-10% and is characteristic to the limited precision of GPC determinations. Therefore, GPC results are most useful when a comparison between the molecular weight distributions of different samples is made during the same series of determinations.

The lignocellulosic samples required sample preparation prior to GPC analysis. First, a saturated solution (8.4% by weight) of lithium chloride (LiCl) was prepared in dimethyl acetamide (DMAc). Approximately 100 mg of the sample was added to approximately 10 g of a freshly prepared saturated LiCl/DMAc solution, and the mixture was heated to approximately 150° C.-170° C. with stirring for 1 hour. The resulting solutions were generally light- to dark-yellow in color. The temperature of the solutions was decreased to approximately 100° C. and heated for an additional 2 hours. The temperatures of the solutions were then decreased to approximately 50° C. and the sample solutions were heated for approximately 48 to 60 hours. Of note, samples irradiated at 100 MRad were more easily solubilized as compared to their untreated counterpart. Additionally, the sheared samples (denoted by the number 132) had slightly lower average molecular weights as compared with uncut samples.

The resulting sample solutions were diluted 1:1 using DMAc as solvent and were filtered through a 0.45 μm PTFE filter. The filtered sample solutions were then analyzed by GPC using the parameters described in Table 7. The peak average molecular weights (Mp) of the samples, as determined by Gel Permeation Chromatography (GPC), are summarized in Tables 3-6. Each sample was prepared in duplicate and each preparation of the sample was analyzed in duplicate (two injections) for a total of four injections per sample. The EasiCal® polystyrene standards PS1A and PS1B were used to generate a calibration curve for the molecular weight scale from about 580 to 7,500,00 Daltons.

TABLE 7

| GPC Analysis Conditions | |
|---|---|
| Instrument: | Waters Alliance GPC 2000 |
| | Plgel 10μ Mixed-B |
| Columns (3): | S/N's: 10M-MB-148-83; |
| | 10M-MB-148-84; 10M-MB-174-129 |
| Mobile Phase (solvent): | 0.5% LiCl in DMAc (1.0 mL/min.) |
| Column/Detector Temperature: | 70° C. |
| Injector Temperature: | 70° C. |
| Sample Loop Size: | 323.5 μL |

Example 7

Time-of-Flight Secondary Ion Mass Spectrometry (ToF-SIMS) Surface Analysis

Time-of-Flight Secondary Ion Mass Spectroscopy (ToF-SIMS) is a surface-sensitive spectroscopy that uses a pulsed ion beam (Cs or microfocused Ga) to remove molecules from the very outermost surface of the sample. The particles are removed from atomic monolayers on the surface (secondary ions). These particles are then accelerated into a "flight tube" and their mass is determined by measuring the exact time at which they reach the detector (i.e. time-of-flight). ToF-SIMS provides detailed elemental and molecular information about the surface, thin layers, interfaces of the sample, and gives a full three-dimensional analysis. The use is widespread, including semiconductors, polymers, paint, coatings, glass, paper, metals, ceramics, biomaterials, pharmaceuticals and organic tissue. Since ToF-SIMS is a survey technique, all the elements in the periodic table, including H, are detected. ToF-SIMS data is presented in Tables 8-11. Parameters used are reported in Table 12.

TABLE 8

Normalized Mean Intensities of Various Positive Ions of Interest
(Normalized relative to total ion counts × 10000)

| | P132 | | P132-10 | | P132-100 | |
|---|---|---|---|---|---|---|
| m/z species | Mean | σ | Mean | σ | Mean | σ |
| 23 Na | 257 | 28 | 276 | 54 | 193 | 36 |
| 27 Al | 647 | 43 | 821 | 399 | 297 | 44 |
| 28 Si | 76 | 45.9 | 197 | 89 | 81.7 | 10.7 |
| 15 $CH_3$ | 77.9 | 7.8 | 161 | 26 | 133 | 12 |
| 27 $C_2H_3$ | 448 | 28 | 720 | 65 | 718 | 82 |
| 39 $C_3H_3$ | 333 | 10 | 463 | 37 | 474 | 26 |
| 41 $C_3H_5$ | 703 | 19 | 820 | 127 | 900 | 63 |
| 43 $C_3H_7$ | 657 | 11 | 757 | 162 | 924 | 118 |
| 115 $C_9H_7$ | 73 | 13.4 | 40.3 | 4.5 | 42.5 | 15.7 |
| 128 $C_{10}H_8$ | 55.5 | 11.6 | 26.8 | 4.8 | 27.7 | 6.9 |
| 73 $C_3H_9Si$* | 181 | 77 | 65.1 | 18.4 | 81.7 | 7.5 |
| 147 $C_5H_{15}OSi_2$* | 72.2 | 33.1 | 24.9 | 10.9 | 38.5 | 4 |
| 207 $C_5H_{15}O_3Si_3$* | 17.2 | 7.8 | 6.26 | 3.05 | 7.49 | 1.77 |
| 647 $C_{42}H_{64}PO_3$ | 3.63 | 1.05 | 1.43 | 1.41 | 10.7 | 7.2 |

TABLE 9

Normalized Mean Intensities of Various Negative Ions of Interest
(Normalized relative to total ion counts × 10000)

| | P132 | | P132-10 | | P132-100 | |
|---|---|---|---|---|---|---|
| m/z species | Mean | σ | Mean | σ | Mean | σ |
| 19 F | 15.3 | 2.1 | 42.4 | 37.8 | 19.2 | 1.9 |
| 35 Cl | 63.8 | 2.8 | 107 | 33 | 74.1 | 5.5 |
| 13 CH | 1900 | 91 | 1970 | 26 | 1500 | 6 |
| 25 $C_2H$ | 247 | 127 | 220 | 99 | 540 | 7 |
| 26 CN | 18.1 | 2.1 | 48.6 | 30.8 | 43.9 | 1.4 |
| 42 CNO | 1.16 | 0.71 | 0.743 | 0.711 | 10.8 | 0.9 |
| 46 $NO_2$ | 1.87 | 0.38 | 1.66 | 1.65 | 12.8 | 1.8 |

TABLE 10

Normalized Mean Intensities of Various Positive Ions of Interest
(Normalized relative to total ion counts × 10000)

| | | P-1e | | P-5e | | P-10e | | P-30e | | P-70e | | P-100e | |
|---|---|---|---|---|---|---|---|---|---|---|---|---|---|
| m/z | Species | Mean | σ | Mean | σ | Mean | σ | Mean | σ | Mean | σ | Mean | σ |
| 23 | Na | 232 | 56 | 370 | 37 | 241 | 44 | 518 | 57 | 350 | 27 | 542 | 104 |
| 27 | Al | 549 | 194 | 677 | 86 | 752 | 371 | 761 | 158 | 516 | 159 | 622 | 166 |
| 28 | Si | 87.3 | 11.3 | 134 | 24 | 159 | 100 | 158 | 32 | 93.7 | 17.1 | 124 | 11 |
| 15 | $CH_3$ | 114 | 23 | 92.9 | 3.9 | 128 | 18 | 110 | 16 | 147 | 16 | 141 | 5 |
| 27 | $C_2H_3$ | 501 | 205 | 551 | 59 | 645 | 165 | 597 | 152 | 707 | 94 | 600 | 55 |
| 39 | $C_3H_3$ | 375 | 80 | 288 | 8 | 379 | 82 | 321 | 57 | 435 | 61 | 417 | 32 |
| 41 | $C_3H_5$ | 716 | 123 | 610 | 24 | 727 | 182 | 607 | 93 | 799 | 112 | 707 | 84 |
| 43 | $C_3H_7$ | 717 | 121 | 628 | 52 | 653 | 172 | 660 | 89 | 861 | 113 | 743 | 73 |

TABLE 10-continued

Normalized Mean Intensities of Various Positive Ions of Interest
(Normalized relative to total ion counts × 10000)

| | | P-1e | | P-5e | | P-10e | | P-30e | | P-70e | | P-100e | |
|---|---|---|---|---|---|---|---|---|---|---|---|---|---|
| m/z | Species | Mean | σ | Mean | σ | Mean | σ | Mean | σ | Mean | σ | Mean | σ |
| 115 | $C_9H_7$ | 49.9 | 14.6 | 43.8 | 2.6 | 42.2 | 7.9 | 41.4 | 10.1 | 27.7 | 8 | 32.4 | 10.5 |
| 128 | $C_{10}H_8$ | 38.8 | 13.1 | 39.2 | 1.9 | 35.2 | 11.8 | 31.9 | 7.8 | 21.2 | 6.1 | 24.2 | 6.8 |
| 73 | $C_3H_9Si^*$ | 92.5 | 3.0 | 80.6 | 2.9 | 72.3 | 7.7 | 75.3 | 11.4 | 63 | 3.4 | 55.8 | 2.1 |
| 147 | $C_5H_{15}OSi_2^*$ | 27.2 | 3.9 | 17.3 | 1.2 | 20.4 | 4.3 | 16.1 | 1.9 | 21.7 | 3.1 | 16.3 | 1.7 |
| 207 | $C_5H_{15}O_3Si_3^*$ | 6.05 | 0.74 | 3.71 | 0.18 | 4.51 | 0.55 | 3.54 | 0.37 | 5.31 | 0.59 | 4.08 | 0.28 |
| 647 | $C_{42}H_{64}PO_3$ | 1.61 | 1.65 | 1.09 | 1.30 | 0.325 | 0.307 | nd | ~ | 0.868 | 1.31 | 0.306 | 0.334 |

TABLE 11

Normalized Mean Intensities of Various Negative Ions of Interest
(Normalized relative to total ion counts × 10000)

| | | P-1e | | P-5e | | P-10e | | P-30e | | P-70e | | P-100e | |
|---|---|---|---|---|---|---|---|---|---|---|---|---|---|
| m/z | species | Mean | σ | Mean | σ | Mean | σ | Mean | σ | Mean | σ | Mean | σ |
| 13 | CH | 1950 | 72 | 1700 | 65 | 1870 | 91 | 1880 | 35 | 2000 | 46 | 2120 | 102 |
| 25 | $C_2H$ | 154 | 47 | 98.8 | 36.3 | 157 | 4 | 230 | 17 | 239 | 22 | 224 | 19 |
| 19 | F | 25.4 | 1 | 24.3 | 1.4 | 74.3 | 18.6 | 40.6 | 14.9 | 25.6 | 1.9 | 21.5 | 2 |
| 35 | Cl | 39.2 | 13.5 | 38.7 | 3.5 | 46.7 | 5.4 | 67.6 | 6.2 | 45.1 | 2.9 | 32.9 | 10.2 |
| 26 | CN | 71.9 | 18.9 | 6.23 | 2.61 | 28.1 | 10.1 | 34.2 | 29.2 | 57.3 | 28.9 | 112 | 60 |
| 42 | CNO | 0.572 | 0.183 | 0.313 | 0.077 | 0.62 | 0.199 | 1.29 | 0.2 | 1.37 | 0.55 | 1.38 | 0.28 |
| 46 | $NO_2$ | 0.331 | 0.057 | 0.596 | 0.255 | 0.668 | 0.149 | 1.44 | 0.19 | 1.92 | 0.29 | 0.549 | 0.1 |

TABLE 12

ToF-SIMS Parameters
Instrument Conditions:

| | |
|---|---|
| Instrument: | PHI TRIFT II |
| Primary Ion Source: | $^{69}Ga$ |
| Primary Ion Beam Potential: | 12 kV + ions |
| | 18 kV − ions |
| Primary Ion Current (DC): | 2 na for P#E samples |
| | 600 pA for P132 samples |
| Energy Filter/CD: | Out/Out |
| Masses Blanked: | None |
| Charge Compensation: | On |

ToF-SIMS uses a focused, pulsed particle beam (typically Cs or Ga) to dislodge chemical species on a materials surface. Particles produced closer to the site of impact tend to be dissociated ions (positive or negative). Secondary particles generated farther from the impact site tend to be molecular compounds, typically fragments of much larger organic macromolecules. The particles are then accelerated into a flight path on their way towards a detector. Because it is possible to measure the "time-of-flight" of the particles from the time of impact to detector on a scale of nano-seconds, it is possible to produce a mass resolution as fine as 0.00× atomic mass units (i.e. one part in a thousand of the mass of a proton). Under typical operating conditions, the results of ToF-SIMS analysis include: a mass spectrum that surveys all atomic masses over a range of 0-10,000 amu, the rastered beam produces maps of any mass of interest on a sub-micron scale, and depth profiles are produced by removal of surface layers by sputtering under the ion beam. Negative ion analysis showed that the polymer had increasing amounts of CNO, CN, and $NO_2$ groups.

Example 8

Porosimetry Analysis of Irradiated Materials

Mercury pore size and pore volume analysis (Table 21) is based on forcing mercury (a non-wetting liquid) into a porous structure under tightly controlled pressures. Since mercury does not wet most substances and will not spontaneously penetrate pores by capillary action, it must be forced into the voids of the sample by applying external pressure. The pressure required to fill the voids is inversely proportional to the size of the pores. Only a small amount of force or pressure is required to fill large voids, whereas much greater pressure is required to fill voids of very small pores.

TABLE 21

Pore Size and Volume Distribution by Mercury Porosimetry

| Sample ID | Total Intrusion Volume (mL/g) | Total Pore Area (m²/g) | Median Pore Diameter (Volume) (μm) | Median Pore Diameter (Area) (μm) | Average Pore Diameter (4V/A) (μm) | Bulk Density @ 0.50 psia (g/mL) | Apparent (skeletal) Density (g/mL) | Porosity (%) |
|---|---|---|---|---|---|---|---|---|
| P132 | 6.0594 | 1.228 | 36.2250 | 13.7278 | 19.7415 | 0.1448 | 1.1785 | 87.7163 |
| P132-10 | 5.5436 | 1.211 | 46.3463 | 4.5646 | 18.3106 | 0.1614 | 1.5355 | 89.4875 |
| P132-100 | 5.3985 | 0.998 | 34.5235 | 18.2005 | 21.6422 | 0.1612 | 1.2413 | 87.0151 |
| P132-181 | 3.2866 | 0.868 | 25.3448 | 12.2410 | 15.1509 | 0.2497 | 1.3916 | 82.0577 |

TABLE 21-continued

Pore Size and Volume Distribution by Mercury Porosimetry

| Sample ID | Total Intrusion Volume (mL/g) | Total Pore Area (m²/g) | Median Pore Diameter (Volume) (μm) | Median Pore Diameter (Area) (μm) | Average Pore Diameter (4V/A) (μm) | Bulk Density @ 0.50 psia (g/mL) | Apparent (skeletal) Density (g/mL) | Porosity (%) |
|---|---|---|---|---|---|---|---|---|
| P132-US | 6.0005 | 14.787 | 98.3459 | 0.0055 | 1.6231 | 0.1404 | 0.8894 | 84.2199 |
| A132 | 2.0037 | 11.759 | 64.6308 | 0.0113 | 0.6816 | 0.3683 | 1.4058 | 73.7990 |
| A132-10 | 1.9514 | 10.326 | 53.2706 | 0.0105 | 0.7560 | 0.3768 | 1.4231 | 73.5241 |
| A132-100 | 1.9394 | 10.205 | 43.8966 | 0.0118 | 0.7602 | 0.3760 | 1.3889 | 72.9264 |
| SG132 | 2.5267 | 8.265 | 57.6958 | 0.0141 | 1.2229 | 0.3119 | 1.4708 | 78.7961 |
| 5G132-10 | 2.1414 | 8.643 | 26.4666 | 0.0103 | 0.9910 | 0.3457 | 1.3315 | 74.0340 |
| 5G132-100 | 2.5142 | 10.766 | 32.7118 | 0.0098 | 0.9342 | 0.3077 | 1.3590 | 77.3593 |
| 5G132-10-US | 4.4043 | 1.722 | 71.5734 | 1.1016 | 10.2319 | 0.1930 | 1.2883 | 85.0169 |
| 5G132-100-US | 4.9665 | 7.358 | 24.8462 | 0.0089 | 2.6998 | 0.1695 | 1.0731 | 84.2010 |
| WS132 | 2.9920 | 5.447 | 76.3675 | 0.0516 | 2.1971 | 0.2773 | 1.6279 | 82.9664 |
| WS132-10 | 3.1138 | 2.901 | 57.4727 | 0.3630 | 4.2940 | 0.2763 | 1.9808 | 86.0484 |
| WS132-100 | 3.2077 | 3.114 | 52.3284 | 0.2876 | 4.1199 | 0.2599 | 1.5611 | 83.3538 |
| A-1e | 1.9535 | 3.698 | 25.3411 | 0.0810 | 2.1130 | 0.3896 | 1.6299 | 76.0992 |
| A-5e | 1.9697 | 6.503 | 29.5954 | 0.0336 | 1.2117 | 0.3748 | 1.4317 | 73.8225 |
| A-10e | 2.0897 | 12.030 | 45.5493 | 0.0101 | 0.6948 | 0.3587 | 1.4321 | 74.9545 |
| A-50e | 2.1141 | 7.291 | 37.0760 | 0.0304 | 1.1599 | 0.3577 | 1.4677 | 75.6264 |
| G-1e | 2.4382 | 7.582 | 58.5521 | 0.0201 | 1.2863 | 0.3144 | 1.3472 | 76.6610 |
| G-5e | 2.4268 | 6.436 | 44.4848 | 0.0225 | 1.5082 | 0.3172 | 1.3782 | 76.9831 |
| G-10e | 2.6708 | 6.865 | 62.8605 | 0.0404 | 1.5562 | 0.2960 | 1.4140 | 79.0638 |
| G-50e | 2.8197 | 6.798 | 56.5048 | 0.0315 | 1.6591 | 0.2794 | 1.3179 | 78.7959 |
| P-1e | 7.7692 | 1.052 | 49.8844 | 22.9315 | 29.5348 | 0.1188 | 1.5443 | 92.3065 |
| P-5e | 7.1261 | 1.212 | 46.6400 | 12.3252 | 23.5166 | 0.1268 | 1.3160 | 90.3644 |
| P-10e | 6.6096 | 1.113 | 41.4252 | 17.4375 | 23.7513 | 0.1374 | 1.4906 | 90.7850 |
| P-50e | 6.5911 | 1.156 | 40.7837 | 15.9823 | 22.7974 | 0.1362 | 1.3302 | 89.7616 |
| P-100e | 5.3507 | 1.195 | 35.3622 | 10.7400 | 17.9063 | 0.1648 | 1.3948 | 88.1840 |
| S | 0.4362 | 0.030 | 102.8411 | 42.5047 | 57.8208 | 0.9334 | 1.5745 | 40.7160 |
| S-1e | 0.3900 | 0.632 | 90.6808 | 0.0041 | 2.4680 | 0.9772 | 1.5790 | 38.1140 |
| S-5e | 0.3914 | 0.337 | 97.1991 | 0.0070 | 4.6406 | 0.9858 | 1.6052 | 38.5847 |
| S-10e | 0.4179 | 0.349 | 113.4360 | 0.0042 | 4.7873 | 0.9469 | 1.5669 | 39.5678 |
| S-30e | 0.4616 | 5.329 | 102.0559 | 0.0042 | 0.3464 | 0.9065 | 1.5585 | 41.8388 |
| S-50e | 0.5217 | 7.162 | 137.2124 | 0.0051 | 0.2914 | 0.8521 | 1.5342 | 44.4582 |
| S-100e | 0.8817 | 15.217 | 76.4577 | 0.0053 | 0.2318 | 0.6478 | 1.5105 | 57.1131 |
| St | 0.6593 | 17.631 | 4.2402 | 0.0053 | 0.1496 | 0.7757 | 1.5877 | 51.1438 |
| St-1e | 0.6720 | 18.078 | 4.3360 | 0.0052 | 0.1487 | 0.7651 | 1.5750 | 51.4206 |
| St-5e | 0.6334 | 19.495 | 4.2848 | 0.0051 | 0.1300 | 0.7794 | 1.5395 | 49.3706 |
| St-10e | 0.6208 | 16.980 | 4.3362 | 0.0056 | 0.1462 | 0.7952 | 1.5703 | 49.3630 |
| St-30e | 0.6892 | 18.066 | 4.4152 | 0.0050 | 0.1526 | 0.7475 | 1.5417 | 51.5165 |
| St-50e | 0.6662 | 18.338 | 4.3759 | 0.0054 | 0.1453 | 0.7637 | 1.5548 | 50.8778 |
| St-100e | 0.6471 | 23.154 | 5.4032 | 0.0048 | 0.1118 | 0.7229 | 1.3582 | 46.7761 |

The AutoPore 9520 can attain a maximum pressure of 414 MPa or 60,000 psia. There are four low pressure stations for sample preparation and collection of macropore data from 0.2 psia to 50 psia. There are two high pressure chambers, which collect data from 25 psia to 60,000 psia. The sample is placed in a bowl-like apparatus called a penetrometer, which is bonded to a glass capillary stem with a metal coating. As mercury invades the voids in and around the sample, it moves down the capillary stem. The loss of mercury from the capillary stem results in a change in the electrical capacitance. The change in capacitance during the experiment is converted to volume of mercury by knowing the stem volume of the penetrometer in use. A variety of penetrometers with different bowl (sample) sizes and capillaries are available to accommodate most sample sizes and configurations. Table 22 below defines some of the key parameters calculated for each sample.

TABLE 22

Definition of Parameters

| Parameter | Description |
|---|---|
| Total Intrusion Volume: | The total volume of mercury intruded during an experiment. This can include interstitial filling between small particles, porosity of sample, and compression volume of sample. |
| Total Pore Area: | The total intrusion volume converted to an area assuming cylindrical shaped pores. |
| Median Pore Diameter (volume): | The size at the 50$^{th}$ percentile on the cumulative volume graph. |
| Median Pore Diameter (area): | The size at the 50$^{th}$ percentile on the cumulative area graph. |
| Average Pore Diameter: | The total pore volume divided by the total pore area (4 V/A). |
| Bulk Density: | The mass of the sample divided by the bulk volume. Bulk volume is determined at the filling pressure, typically 0.5 psia. |

TABLE 22-continued

Definition of Parameters

| Parameter | Description |
|---|---|
| Apparent Density: | The mass of sample divided by the volume of sample measured at highest pressure, typically 60,000 psia. |
| Porosity: | (Bulk Density/Apparent Density) × 100% |

Example 9

Particle Size Analysis of Irradiated Materials

The technique of particle sizing by static light scattering is based on Mie theory (which also encompasses Fraunhofer theory). Mie theory predicts the intensity vs. angle relationship as a function of the size for spherical scattering particles provided that other system variables are known and held constant. These variables are the wavelength of incident light and the relative refractive index of the sample material. Application of Mie theory provides the detailed particle size information. Table 23 summarizes particle size using median diameter, mean diameter, and modal diameter as parameters.

TABLE 23

Particle Size by Laser Light Scattering (Dry Sample Dispersion)

| Sample ID | Median Diameter (μm) | Mean Diameter (μm) | Modal Diameter (μm) |
|---|---|---|---|
| A132 | 380.695 | 418.778 | 442.258 |
| A132-10 | 321.742 | 366.231 | 410.156 |
| A132-100 | 301.786 | 348.633 | 444.169 |
| SG132 | 369.400 | 411.790 | 455.508 |
| SG132-10 | 278.793 | 325.497 | 426.717 |
| SG132-100 | 242.757 | 298.686 | 390.097 |
| WS132 | 407.335 | 445.618 | 467.978 |
| WS132-10 | 194.237 | 226.604 | 297.941 |
| WS132-100 | 201.975 | 236.037 | 307.304 |

Particle size was determined by Laser Light Scattering (Dry Sample Dispersion) using a Malvern Mastersizer 2000 using the following conditions:
  Feed Rate: 35%
  Disperser Pressure: 4 Bar
  Optical Model: (2.610, 1.000i), 1.000

An appropriate amount of sample was introduced onto a vibratory tray. The feed rate and air pressure were adjusted to ensure that the particles were properly dispersed. The key component is selecting an air pressure that will break up agglomerations, but does not compromise the sample integrity. The amount of sample needed varies depending on the size of the particles. In general, samples with fine particles require less material than samples with coarse particles.

Example 10

Surface Area Analysis of Irradiated Materials

Surface area of each sample was analyzed using a Micromeritics ASAP 2420 Accelerated Surface Area and Porosimetry System. The samples were prepared by first degassing for 16 hours at 40° C. Next, free space (both warm and cold) with helium is calculated and then the sample tube is evacuated again to remove the helium. Data collection begins after this second evacuation and consists of defining target pressures, which control how much gas is dosed onto the sample. At each target pressure, the quantity of gas adsorbed and the actual pressure are determined and recorded. The pressure inside the sample tube is measured with a pressure transducer. Additional doses of gas will continue until the target pressure is achieved and allowed to equilibrate. The quantity of gas adsorbed is determined by summing multiple doses onto the sample. The pressure and quantity define a gas adsorption isotherm and are used to calculate a number of parameters, including BET surface area (Table 24).

TABLE 24

Summary of Surface Area by Gas Adsorption

| Sample ID | Single point surface area (m$^2$/g) | | BET Surface Area (m$^2$/g) |
|---|---|---|---|
| P132 | @ P/Po = 0.250387771 | 1.5253 | 1.6897 |
| P132-10 | @ P/Po = 0.239496722 | 1.0212 | 1.2782 |
| P132-100 | @ P/Po = 0.240538100 | 1.0338 | 1.2622 |
| P132-181 | @ P/Po = 0.239166091 | 0.5102 | 0.6448 |
| P132-US | @ P/Po = 0.217359072 | 1.0983 | 1.6793 |
| A132 | @ P/Po = 0.240040610 | 0.5400 | 0.7614 |
| A132-10 | @ P/Po = 0.211218936 | 0.5383 | 0.7212 |
| A132-100 | @ P/Po = 0.238791097 | 0.4258 | 0.5538 |
| SG132 | @ P/Po = 0.237989353 | 0.6359 | 0.8350 |
| SG132-10 | @ P/Po = 0.238576905 | 0.6794 | 0.8689 |
| SG132-100 | @ P/Po = 0.241960361 | 0.5518 | 0.7034 |
| SG132-10-US | @ P/Po = 0.225692889 | 0.5693 | 0.7510 |
| SG132-100-US | @ P/Po = 0.225935246 | 1.0983 | 1.4963 |
| G-10-US | | | 0.751 |
| G100-US | | | 1.496 |
| G132-US | | | 1.679 |
| WS132 | @ P/Po = 0.237823664 | 0.6582 | 0.8663 |
| WS132-10 | @ P/Po = 0.238612476 | 0.6191 | 0.7912 |
| WS132-100 | @ P/Po = 0.238398832 | 0.6255 | 0.8143 |
| A-1e | @ P/Po = 0.238098138 | 0.6518 | 0.8368 |
| A-5e | @ P/Po = 0.243184477 | 0.6263 | 0.7865 |
| A-10e | @ P/Po = 0.243163236 | 0.4899 | 0.6170 |
| A-50e | @ P/Po = 0.243225512 | 0.4489 | 0.5730 |
| G-1e | @ P/Po = 0.238496102 | 0.5489 | 0.7038 |
| G-5e | @ P/Po = 0.242792602 | 0.5621 | 0.7086 |
| G-10e | @ P/Po = 0.243066031 | 0.5021 | 0.6363 |
| G-50e | @ P/Po = 0.238291132 | 0.4913 | 0.6333 |
| P-1e | @ P/Po = 0.240842223 | 1.1413 | 1.4442 |
| P-5e | @ P/Po = 0.240789274 | 1.0187 | 1.3288 |
| P-10e | @ P/Po = 0.240116967 | 1.1015 | 1.3657 |
| P-50e | @ P/Po = 0.240072114 | 1.0089 | 1.2593 |
| P-100e | @ P/Po = 0.236541386 | 0.9116 | 1.1677 |
| S | @ P/Po = 0.225335038 | 0.0147 | 0.0279 |
| S-1e | @ P/Po = 0.217142291 | 0.0193 | 0.0372 |
| S-5e | @ P/Po = 0.133107838 | 0.0201 | 0.0485 |
| S-10e | @ P/Po = 0.244886517 | 0.0236 | 0.0317 |
| S-30e | @ P/Po = 0.237929400 | 0.0309 | 0.0428 |
| S-50e | @ P/Po = 0.245494494 | 0.0262 | 0.0365 |
| S-100e | @ P/Po = 0.224698551 | 0.0368 | 0.0506 |
| St | @ P/Po = 0.238324949 | 0.3126 | 0.4013 |
| St-1e | @ P/Po = 0.238432726 | 0.3254 | 0.4223 |
| St-5e | @ P/Po = 0.238363587 | 0.3106 | 0.4071 |
| St-10e | @ P/Po = 0.238341099 | 0.3205 | 0.4268 |
| St-30e | @ P/Po = 0.238629889 | 0.3118 | 0.4189 |
| St-50e | @ P/Po = 0.244630980 | 0.3119 | 0.3969 |
| St-100e | @ P/Po = 0.238421621 | 0.2932 | 0.3677 |

The BET model for isotherms is a widely used theory for calculating the specific surface area. The analysis involves determining the monolayer capacity of the sample surface by calculating the amount required to cover the entire surface with a single densely packed layer of krypton. The monolayer capacity is multiplied by the cross sectional area of a molecule of probe gas to determine the total surface area. Specific surface area is the surface area of the sample aliquot divided by the mass of the sample.

Example 11

Fiber Length Determination of Irradiated Materials

Fiber length distribution testing was performed in triplicate on the samples submitted using the Techpap MorFi LB01 system. The average fiber length and width are reported in Table 25.

TABLE 25

Summary of Lignocellulosic Fiber Length and Width Data

| Sample ID | Arithmetic Average (mm) | Average Length Weighted in Length (mm) | Statistically Corrected Average Length Weighted in Length (mm) | Width (micrometers) (μm) |
| --- | --- | --- | --- | --- |
| P132-10 | 0.484 | 0.615 | 0.773 | 24.7 |
| P132-100 | 0.369 | 0.423 | 0.496 | 23.8 |
| P132-181 | 0.312 | 0.342 | 0.392 | 24.4 |
| A132-10 | 0.382 | 0.423 | 0.650 | 43.2 |
| A132-100 | 0.362 | 0.435 | 0.592 | 29.9 |
| SG132-10 | 0.328 | 0.363 | 0.521 | 44.0 |
| SG132-100 | 0.325 | 0.351 | 0.466 | 43.8 |
| WS132-10 | 0.353 | 0.381 | 0.565 | 44.7 |
| WS132-100 | 0.354 | 0.371 | 0.536 | 45.4 |

Example 12

Fourier Transform Infrared (FT-IR) Spectrum of Irradiated and Unirradiated Kraft Paper FT-IR analysis was performed on a Nicolet/Impact 400. The results indicate that samples P132, P132-10, P132-100, P-1e, P-5e, P-10e, P-30e, P-70e, and P-100e are consistent with a cellulose-based material.

FIG. 3 is an infrared spectrum of Kraft board paper sheared according to Example 4, while FIG. 4 is an infrared spectrum of the Kraft paper of FIG. 3 after irradiation with 100 Mrad of gamma radiation. The irradiated sample shows an additional peak in region A (centered about 1730 cm$^{-1}$) that is not found in the un-irradiated material. Of note, an increase in the amount of a carbonyl absorption at ~1650 cm$^{-1}$ was detected when going from P132 to P132-10 to P132-100. Similar results were observed for the samples P-1e, P-5e, P-10e, P-30e, P-70e, and P-100e.

Example 13

Proton and Carbon-13 Nuclear Magnetic Resonance ($^1$H-NMR and $^{13}$C-NMR) Spectra of Irradiated and Unirradiated Kraft Paper Sample Preparation The samples P132, P132-10, P132-100, P-1e, P-5e, P-10e, P-30e, P-70e, and P-100e were prepared for analysis by dissolution with DMSO-$d_6$ with 2% tetrabutyl ammonium fluoride trihydrate. The samples that had undergone lower levels of irradiation were significantly less soluble than the samples with higher irradiation. Unirradiated samples formed a gel in this solvent mixture, but heating to 60° C. resolved the peaks in the NMR spectra. The samples having undergone higher levels of irradiation were soluble at a concentration of 10% wt/wt.

Analysis $^1$H-NMR spectra of the samples at 15 mg/mL showed a distinct very broad resonance peak centered at 16 ppm (FIGS. 5A-5J). This peak is characteristic of an exchangeable —OH proton for an enol and was confirmed by a "$d_2$O shake." Model compounds (acetylacetone, glucuronic acid, and ketogulonic acid) were analyzed and made a convincing case that this peak was indeed an exchangeable enol proton. This proposed enol peak was very sensitive to concentration effects, and we were unable to conclude whether this resonance was due to an enol or possibly a carboxylic acid.

Figure 5A:
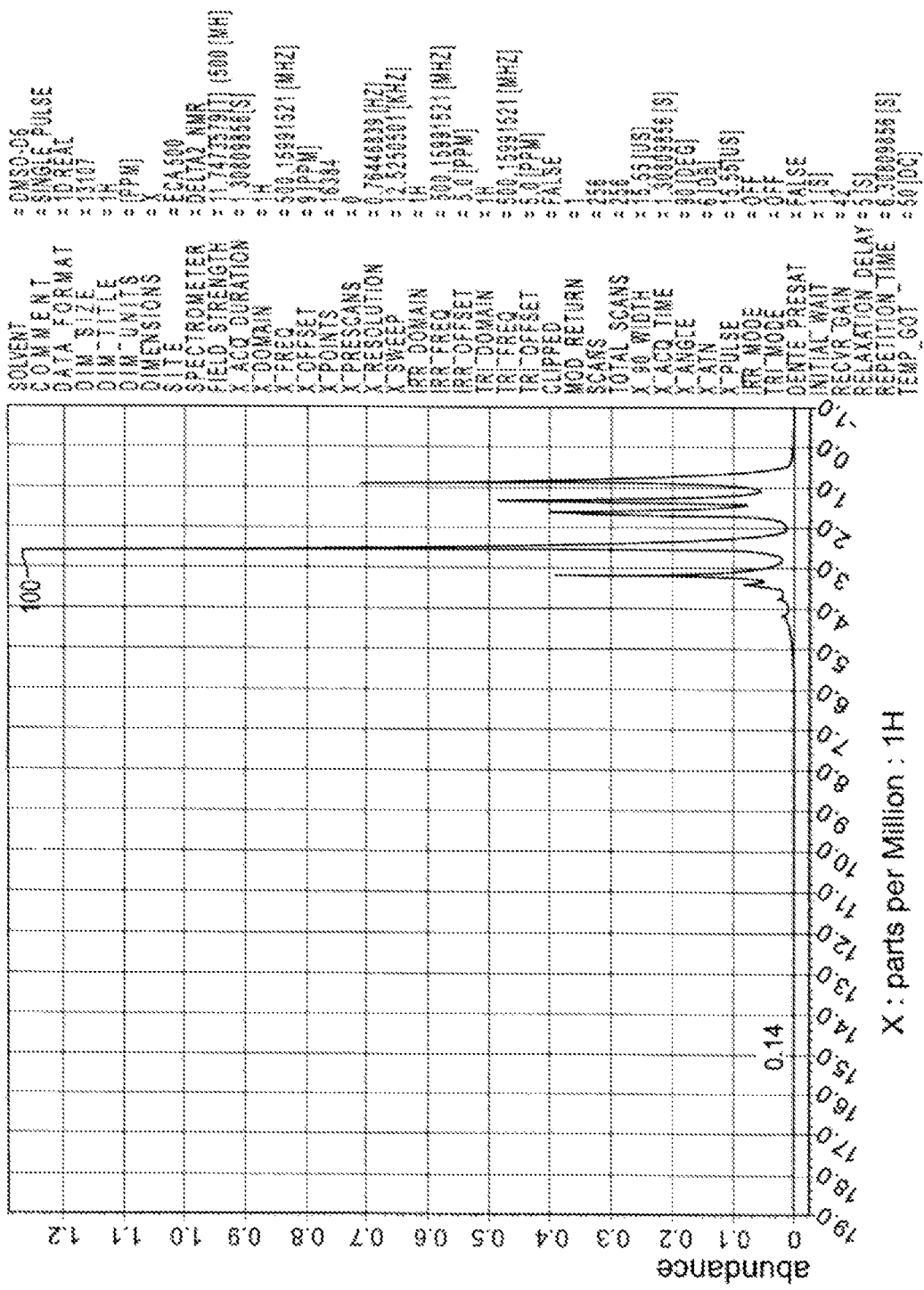
FIGS. 5A-5I are $^1$H-NMR spectra of samples P132, P132-10, P132-100, P-1e, P-5e, P-10e, P-30e, P-70e, and P-100e in Example 13.
Figure 5B:
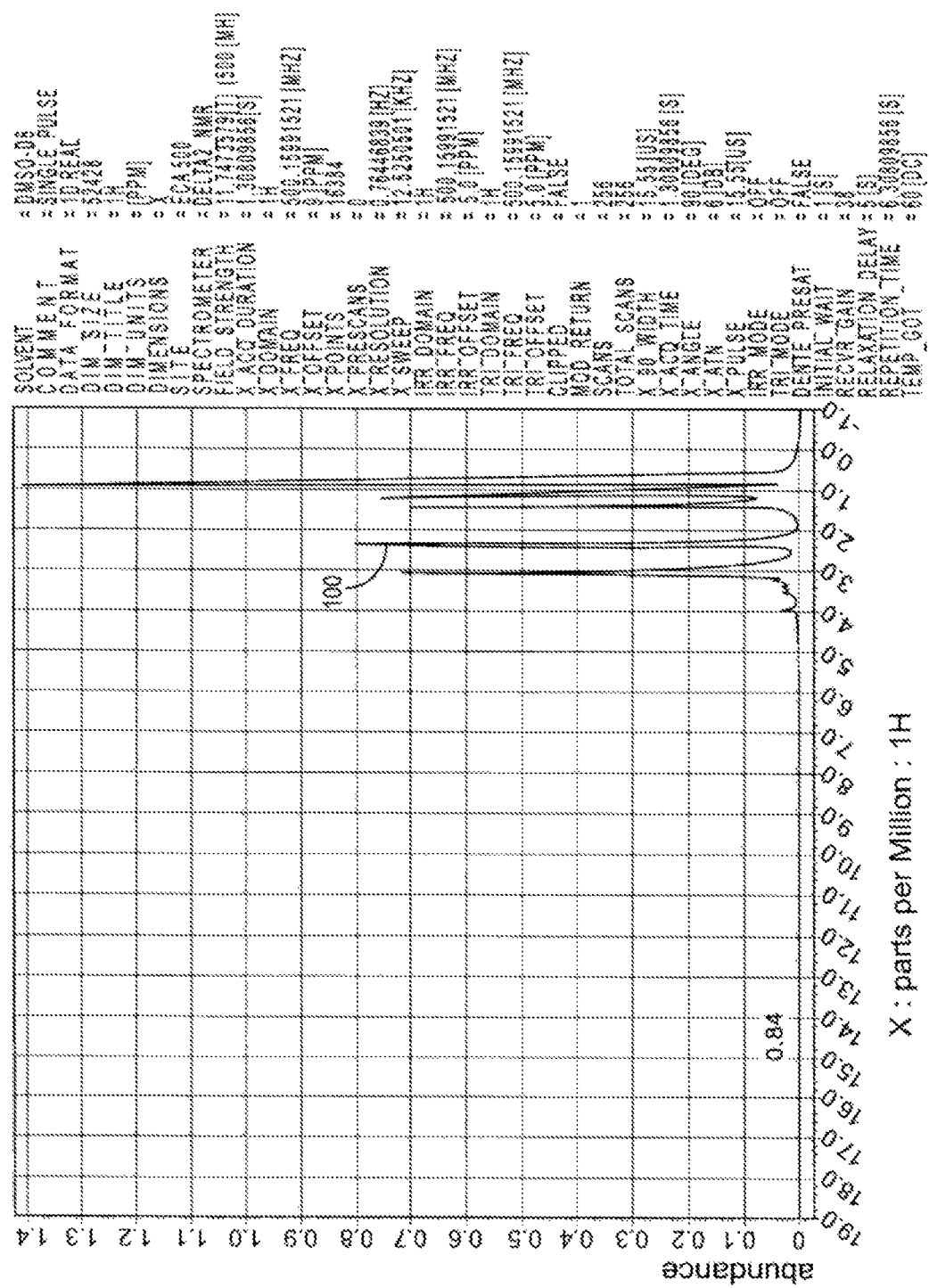
Figure 5C:
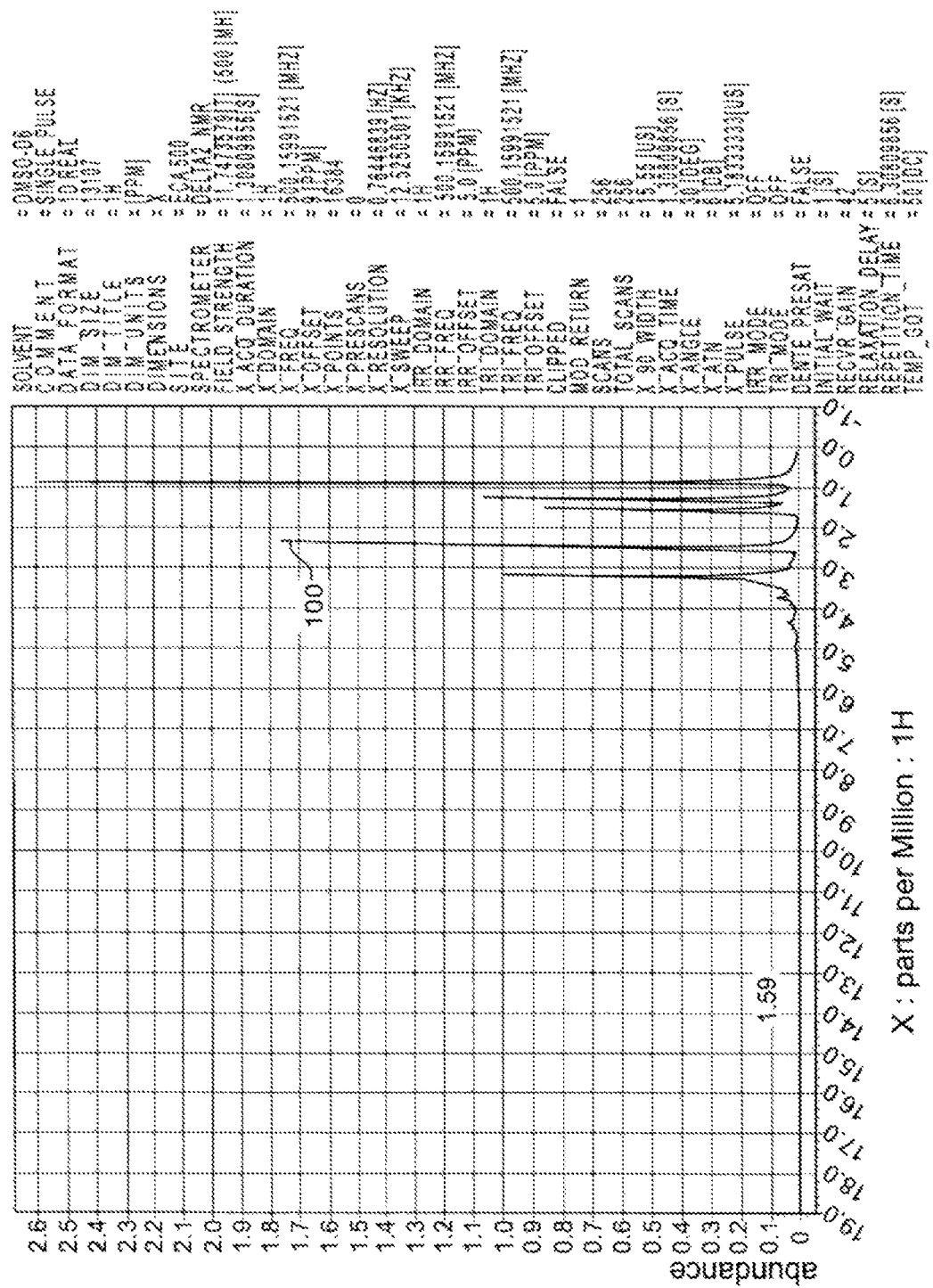
Figure 5D:
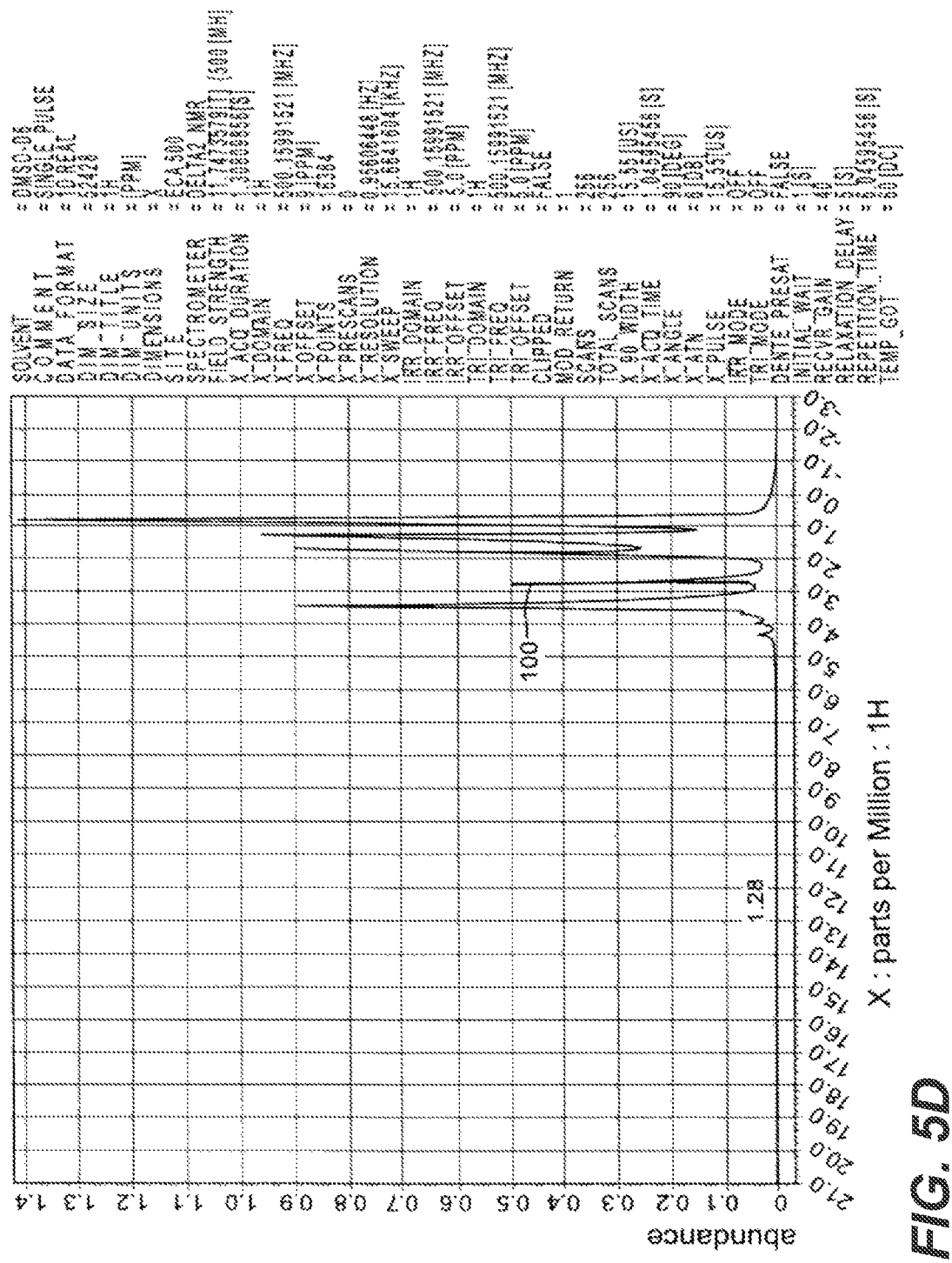
Figure 5E:
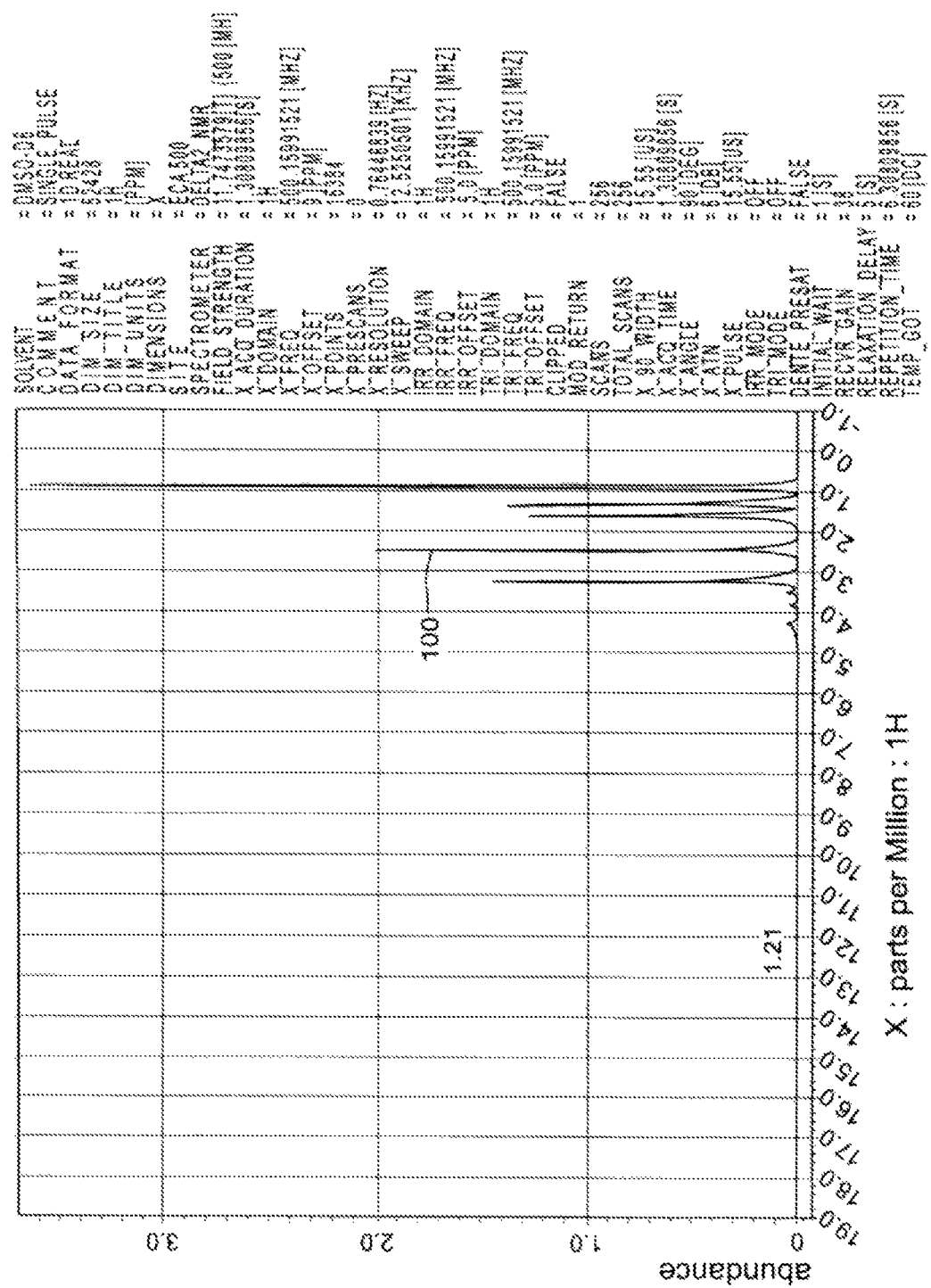
Figure 5F:
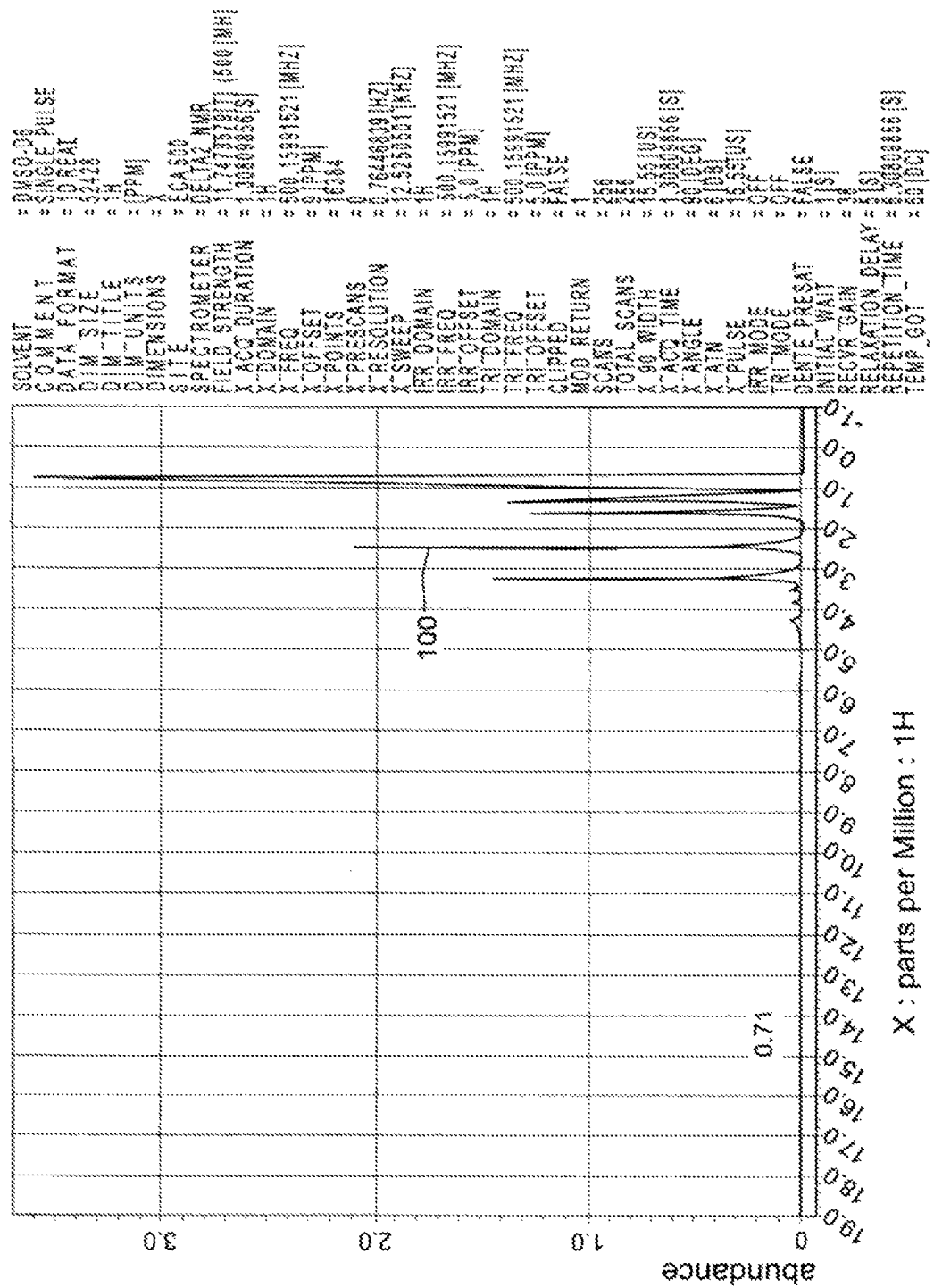
Figure 5G:
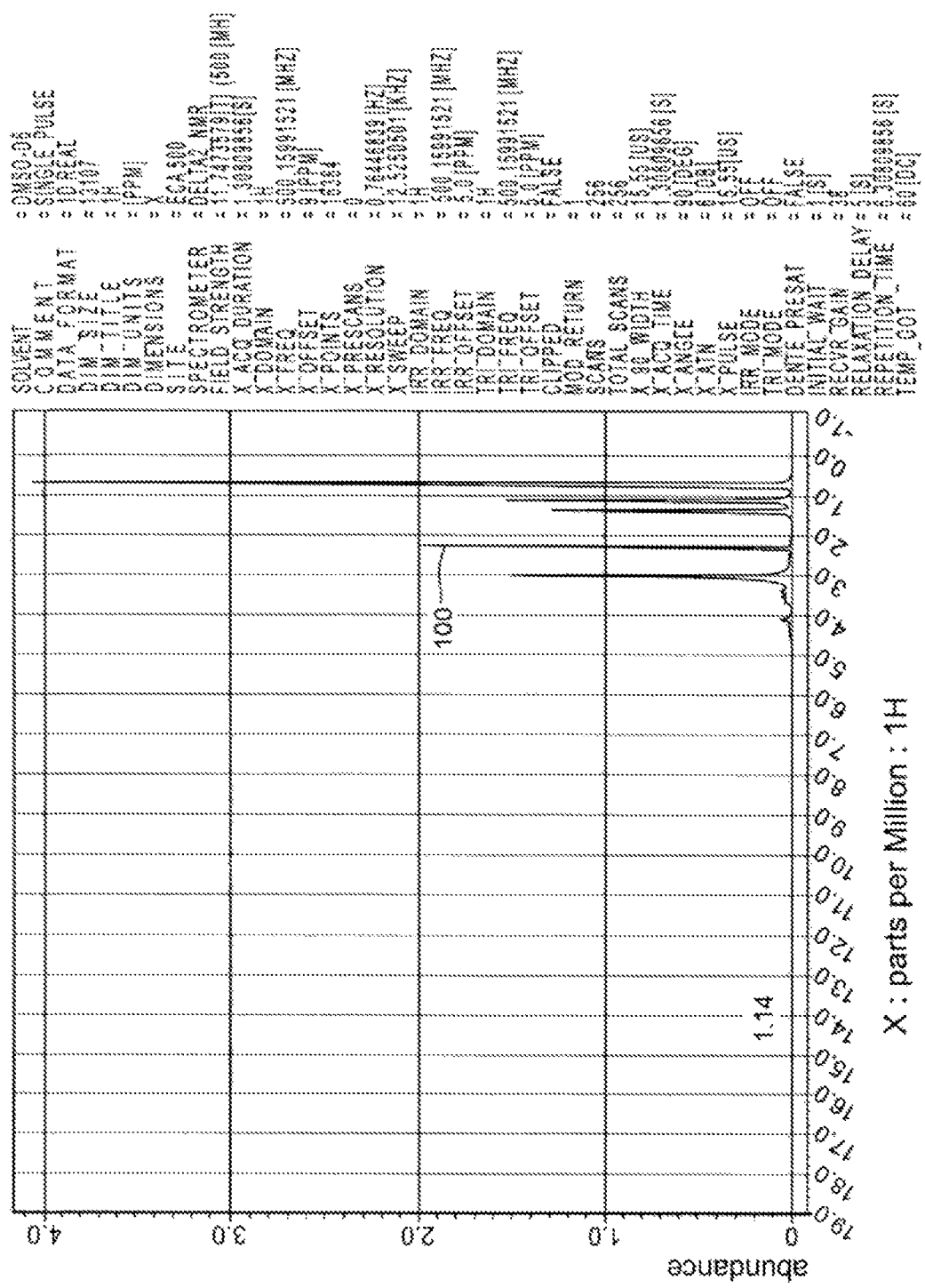
Figure 5H:
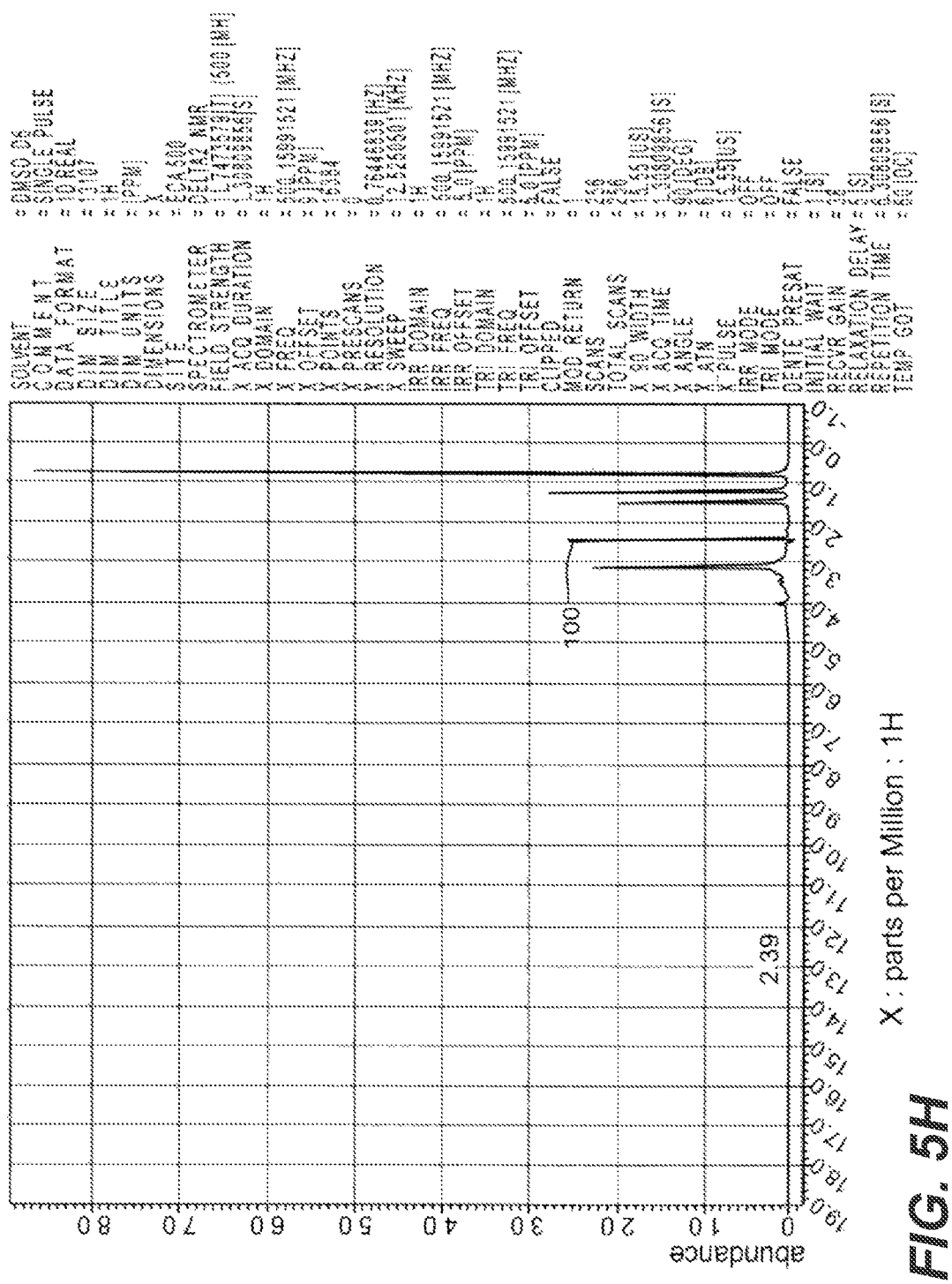
Figure 5I:
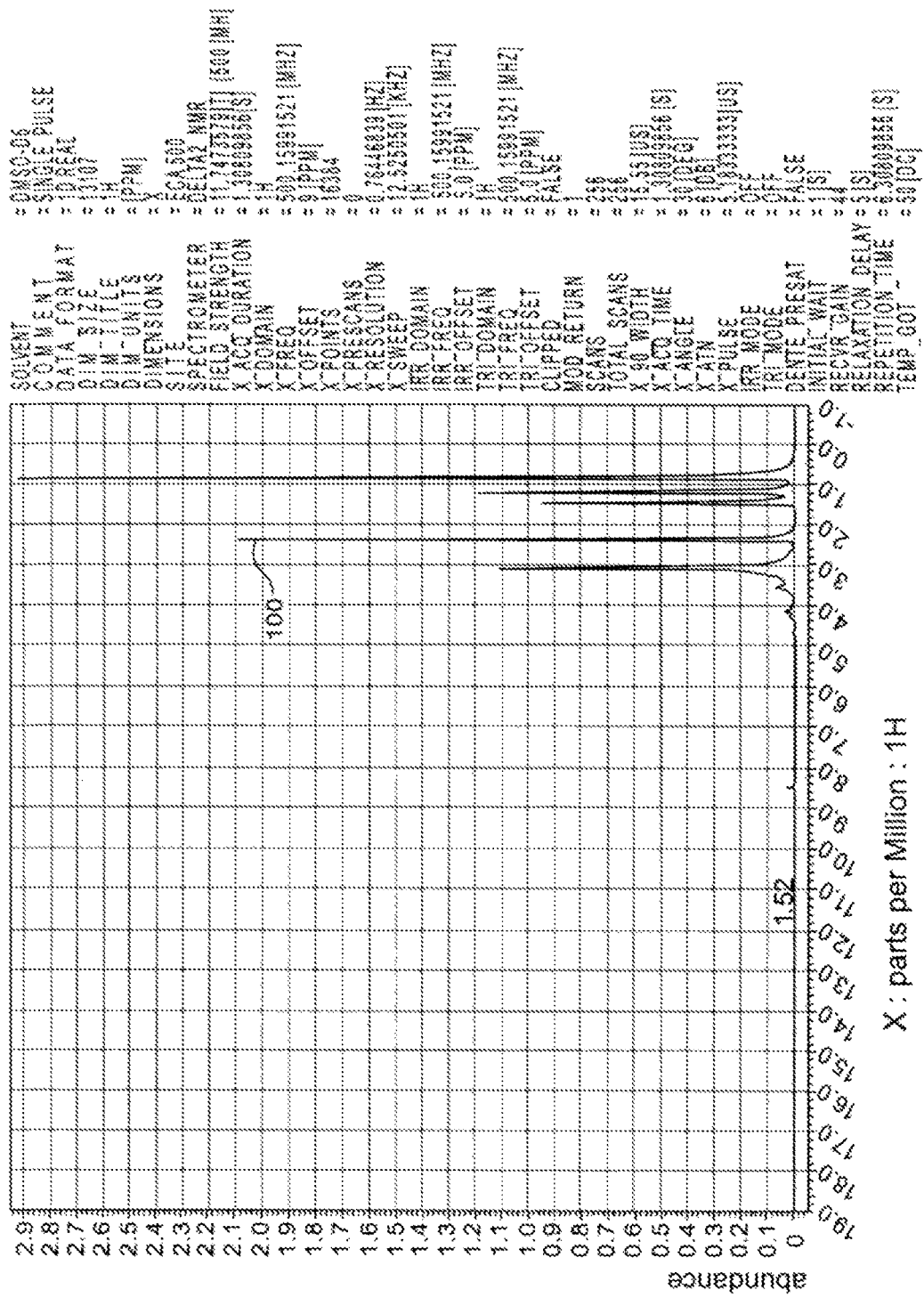
Figure 5J:
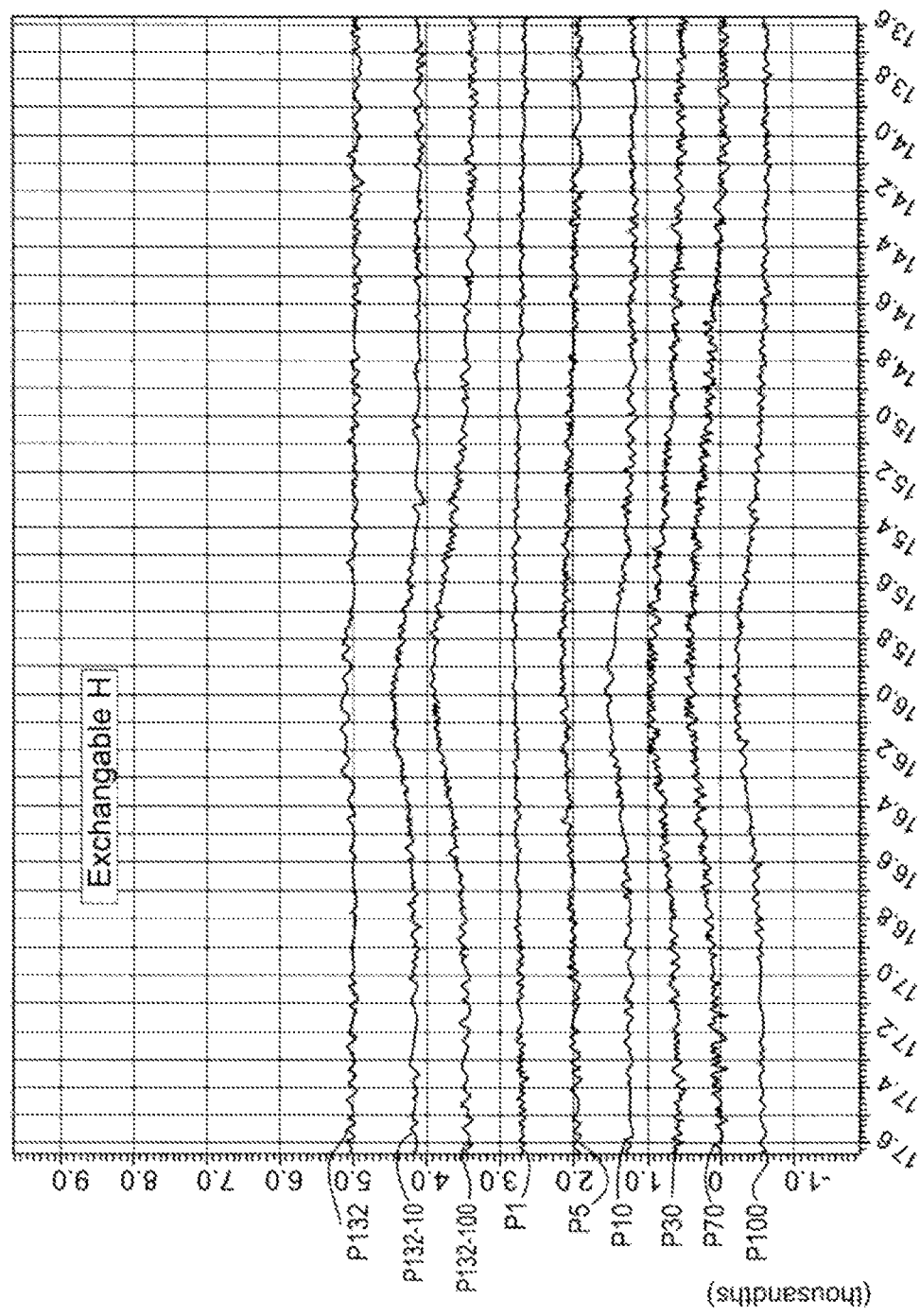
FIG. 5J is a comparison of the exchangeable proton at ~16 ppm from FIGS. 5A-5I.
Figure 5K:
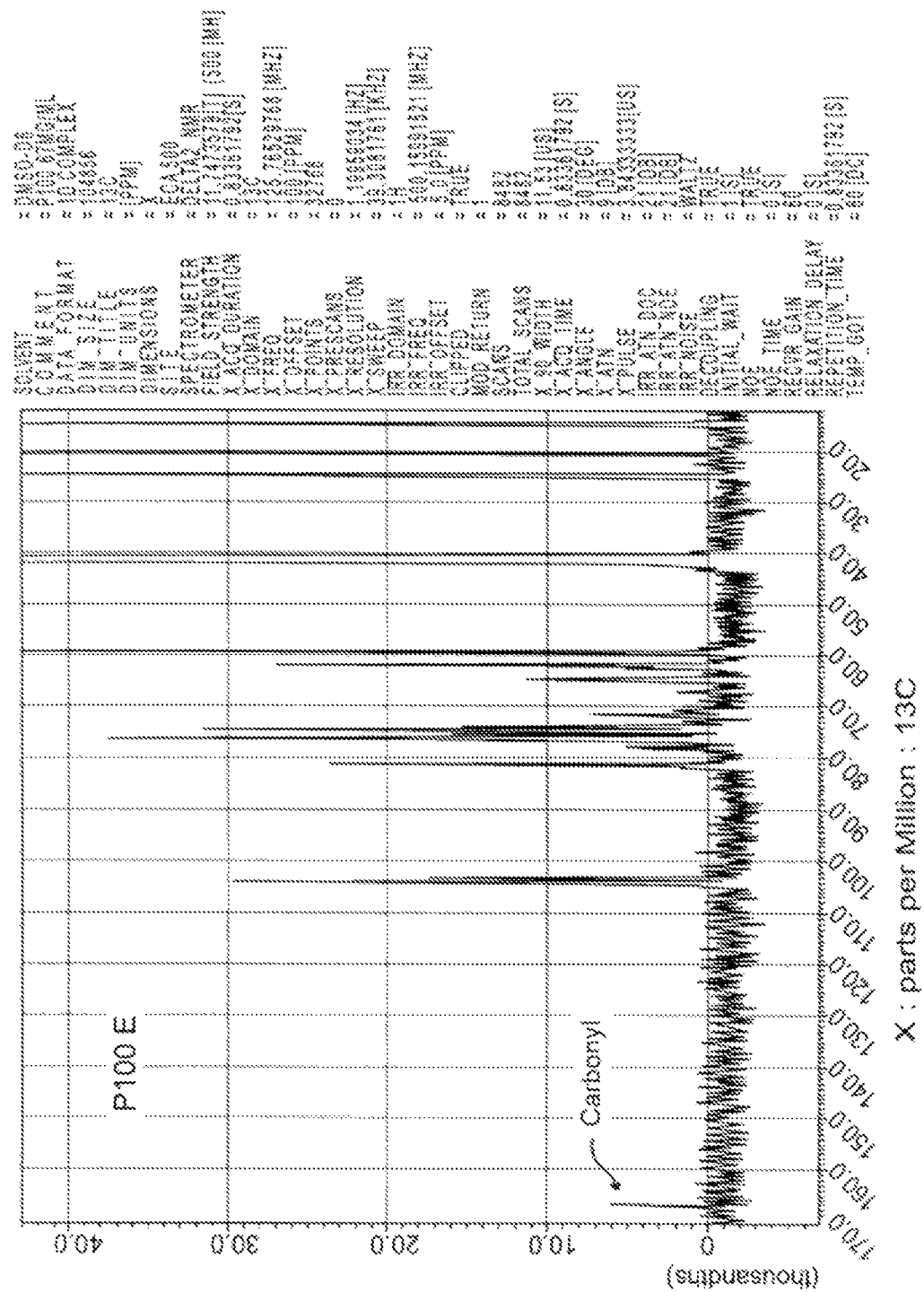
FIG. 5K is a $^{13}$C-NMR of sample P-100e.
Figure 5L:
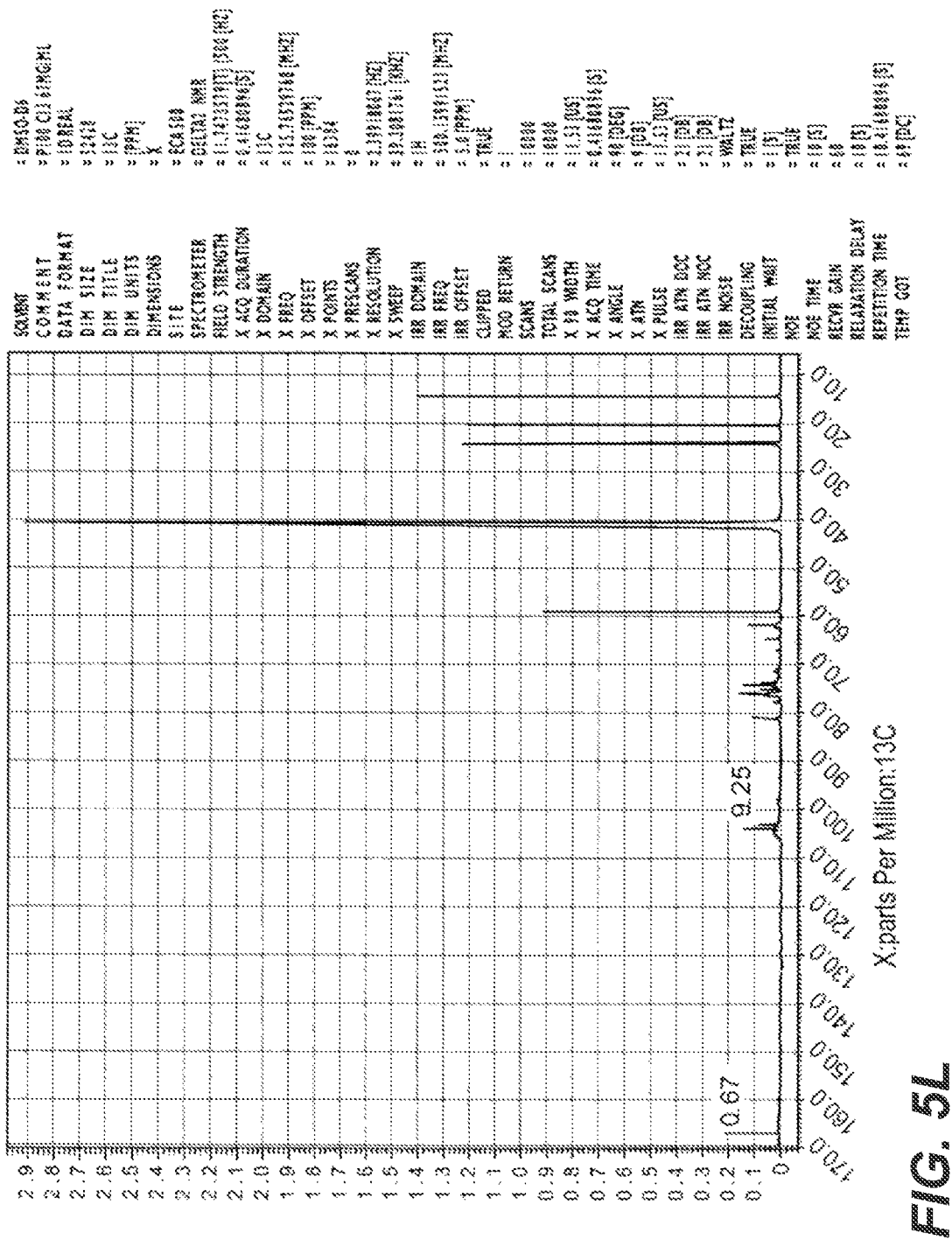
FIGS. 5L-5M are $^{13}$C-NMR of sample P-100e with a delay time of 10 seconds.
Figure 5M:
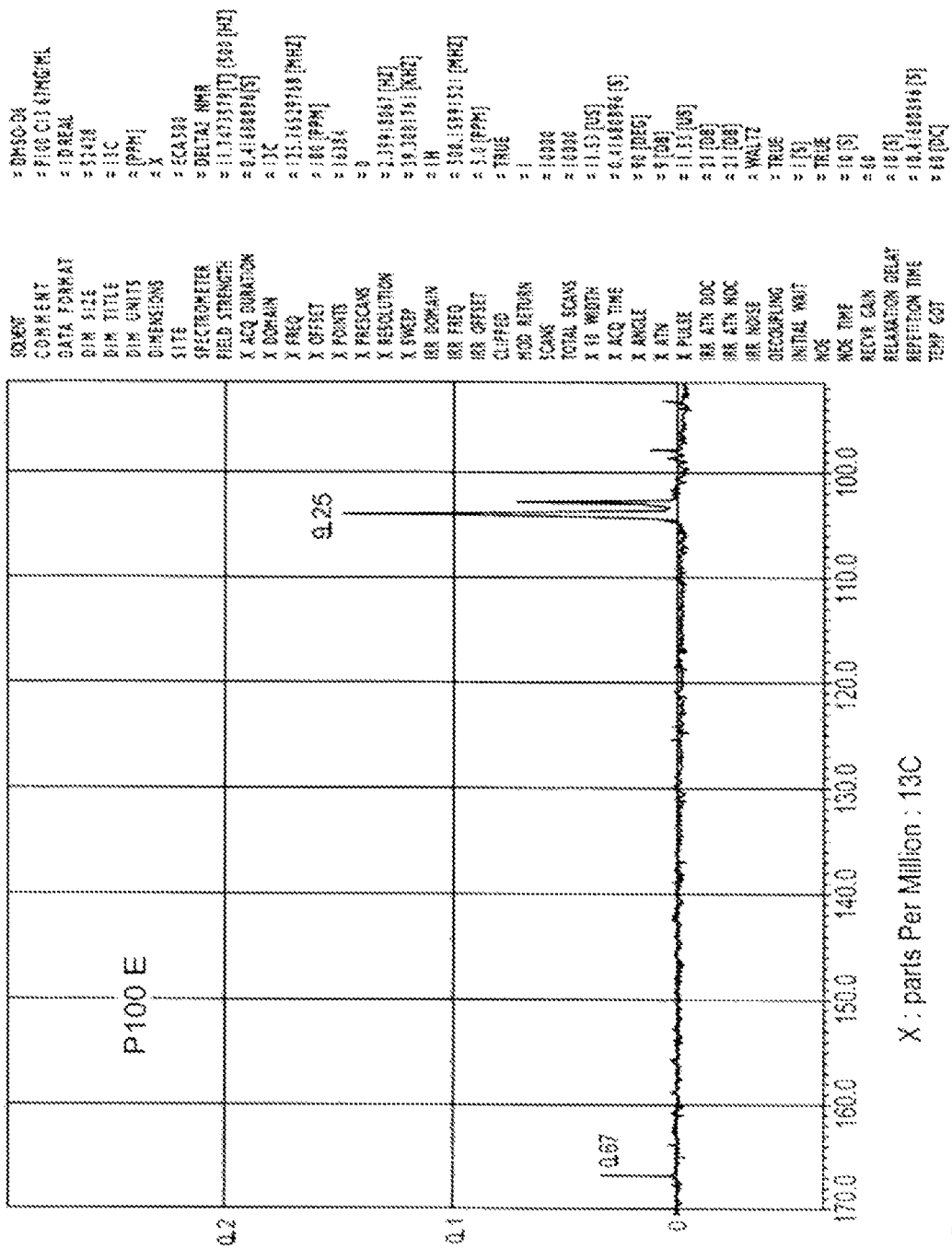
Figure 5N:
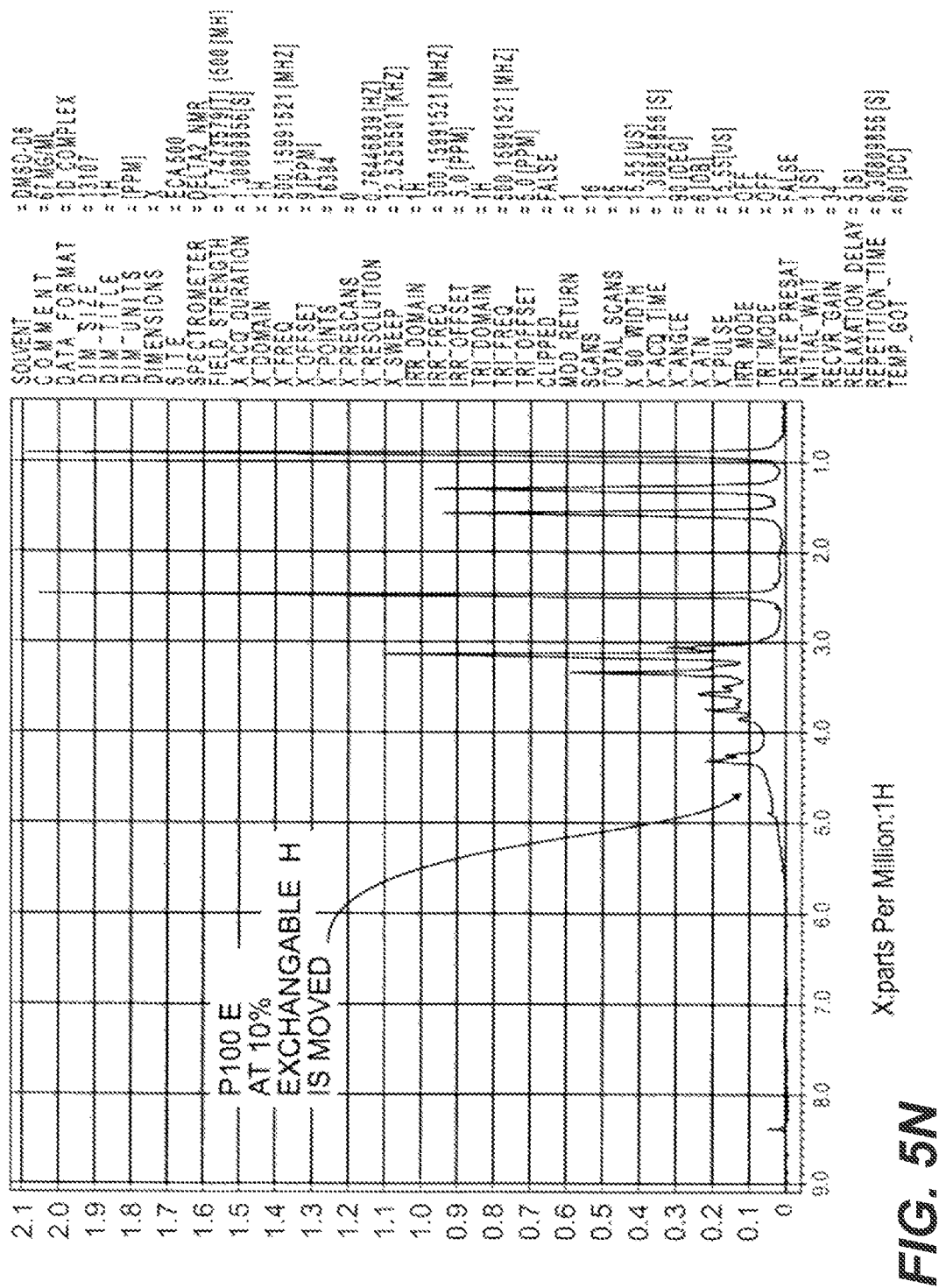
FIG. 5N is a $^1$H-NMR at a concentration of 10% wt./wt. of sample P-100e.
Figure 6:
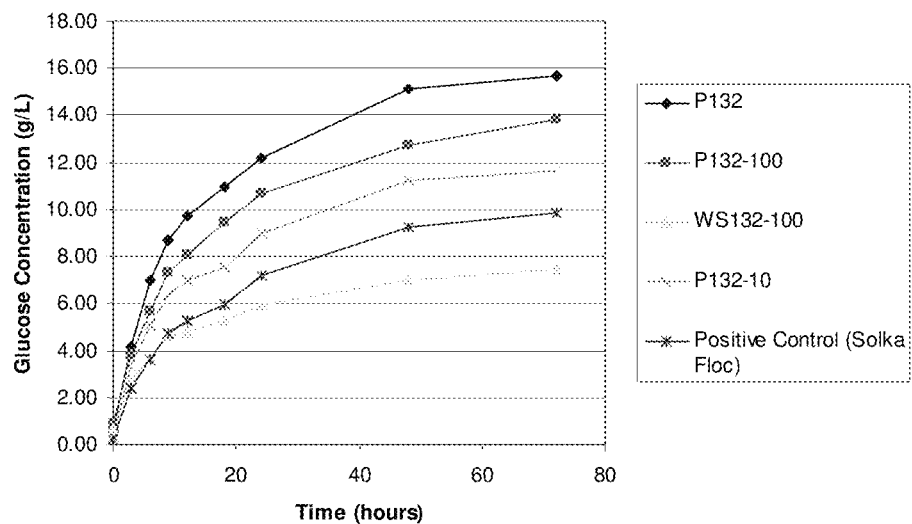
FIG. 6 is a graph showing glucose concentration over time.

The carboxylic acid proton resonances of the model compounds were similar to what was observed for the treated cellulose samples. These model compounds were shifted up field to ~5-6 ppm. Preparation of P-100e at higher concentrations (~10% wt/wt) led to the dramatic down field shifting to where the carboxylic acid resonances of the model compounds were found (~6 ppm) (FIG. 5N). These results lead to the conclusion that this resonance is unreliable for characterizing this functional group, however the data suggests that the number of exchangeable hydrogens increases with increasing irradiation of the sample. Also, no vinyl protons were detected.

The $^{13}$C NMR spectra of the samples confirm the presence of a carbonyl of a carboxylic acid or a carboxylic acid derivative. This new peak (at 168 ppm) is not present in the untreated samples (FIG. 5K). A $^{13}$C NMR spectrum with a long delay allowed the quantitation of the signal for P-100e (FIGS. 5L-5M). Comparison of the integration of the carbonyl resonance to the resonances at approximately 100 ppm (the C1 signals) suggests that the ratio of the carbonyl carbon to C1 is 1:13.8 or roughly 1 carbonyl for every 14 glucose units. The chemical shift at 100 ppm correlates well with glucuronic acid.

Titration

Samples P-100e and P132-100 (1 g) were suspended in deionized water (25 mL). The indicator alizarin yellow was added to each sample with stirring. P-100e was more difficult to wet. Both samples were titrated with a solution of 0.2M NaOH. The end point was very subtle and was confirmed by using pH paper. The starting pH of the samples was ~4 for both samples. P132-100 required 0.4 milliequivalents of hydroxide, which gives a molecular weight for the carboxylic acid of 2500 amu. If 180 amu is used for a monomer, this suggests there is one carboxylic acid group for 13.9 monomer units. Likewise, P-100e required 3.2 milliequivalents of hydroxide, which calculates to be one carboxylic acid group for every 17.4 monomer units.

Conclusions

The C-6 carbon of cellulose appears to be oxidized to the carboxylic acid (a glucuronic acid derivative) in this oxidation is surprisingly specific. This oxidation is in agreement with the IR band that grows with irradiation at ~1740 cm$^{-1}$, which corresponds to an aliphatic carboxylic acid. The titration results are in agreement with the quantitative $^{13}$C NMR. The increased solubility of the sample with the higher levels of irradiation correlates well with the increasing number of carboxylic acid protons. A proposed mechanism for the degradation of "C-6 oxidized cellulose" is provided below in Scheme 1.

Scheme 1

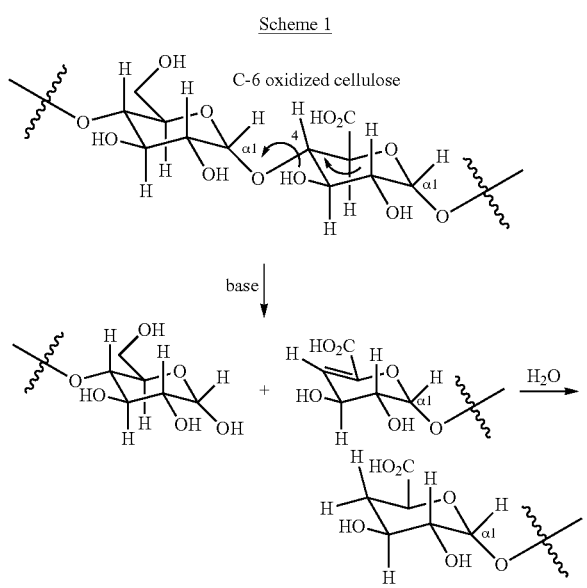

Example 14

Microbial Testing of Pretreated Biomass

Specific lignocellulosic materials pretreated as described herein are analyzed for toxicity to common strains of yeast and bacteria used in the biofuels industry for the fermentation step in ethanol production. Additionally, sugar content and compatibility with cellulase enzymes are examined to determine the viability of the treatment process. Testing of the pretreated materials is carried out in two phases as follows.

Phase 1: Toxicity and Sugar Content

Toxicity of the pretreated grasses and paper feedstocks is measured in yeast *Saccharomyces cerevisiae* (wine yeast) and *Pichia stipitis* (ATCC 66278) as well as the bacteria *Zymomonas mobilis* (ATCC 31821) and *Clostridium thermocellum* (ATCC 31924). A growth study is performed with each of the organisms to determine the optimal time of incubation and sampling.

Each of the feedstocks is then incubated, in duplicate, with *S. cerevisiae*, *P. stipitis*, *Z. mobilis*, and *C. thermocellum* in a standard microbiological medium for each organism. YM broth is used for the two yeast strains, *S. cerevisiae* and *P. stipitis*. RM medium is used for *Z. mobilis* and CM4 medium for *C. thermocellum*. A positive control, with pure sugar added, but no feedstock, is used for comparison. During the incubation, a total of five samples is taken over a 12 hour period at time 0, 3, 6, 9, and 12 hours and analyzed for viability (plate counts for *Z. mobilis* and direct counts for *S. cerevisiae*) and ethanol concentration.

Sugar content of the feedstocks is measured using High Performance Liquid Chromatography (HPLC) equipped with either a Shodex™ sugar SP0810 or Biorad Aminex® HPX-87P column. Each of the feedstocks (approx. 5 g) is mixed with reverse osmosis (RO) water for 1 hour. The liquid portion of the mixture is removed and analyzed for glucose, galactose, xylose, mannose, arabinose, and cellobiose content. The analysis is performed according to National Bioenergy Center protocol Determination of Structural Carbohydrates and Lignin in Biomass.

Phase 2: Cellulase Compatibility

Feedstocks are tested, in duplicate, with commercially available Accellerase® 1000, which contains a complex of enzymes that reduces lignocellulosic biomass into fermentable sugars, at the recommended temperature and concentration in an Erlenmeyer flask. The flasks are incubated with moderate shaking at around 200 rpm for 12 hours. During that time, samples are taken every three hours at time 0, 3, 6, 9, and 12 hours to determine the concentration of reducing sugars (Hope and Dean, Biotech J., 1974, 144:403) in the liquid portion of the flasks.

Example 15

Sugar Concentration Analysis Using HPLC 13 samples were analyzed for sugar concentration (HPLC) and toxicity against 3 microorganisms (*Pichia stipitis*, *Saccharomyces cerevisiae*, and *Zymomonas mobilis*. Table 26 lists the equipment used for these experiments. Table 27 and 28 provide a list of the sugars (including vendor and lot numbers) used to prepare the HPLC standard and the protocol used to prepare the HPLC standard, respectively.

TABLE 26

Equipment Utilized in Experiments

| Equipment | Manufacturer, Name |
|---|---|
| pH meter | Orion |
| Shakers (2) | B. Braun Biotech, Certomat BS-1 |
| HPLC | Waters, 2690 HPLC Module |
| Spectrophotometer | Unicam, UV300 |
| YSI Biochem Analyzer | Interscience, YSI |

TABLE 27

Sugars used in HPLC analysis

| Sugar | Manufacturer | Ref # | Lot # |
|---|---|---|---|
| glucose | BioChemika | 49140 | 1284892 |
| xylose | | 95731 | 1304473 51707231 |
| cellobiose | | 22150 | 1303157 14806191 |
| arabinose | | 10840 | 1188979 24105272 |
| mannose | | 63582 | 363063/1 22097 |
| galactose | | 48259 | 46032/1 33197 |

TABLE 28

Preparation of HPLC standards

| Desired Concentration (mg/mL) | Volume of sugar solution | Volume of Nanopure Water (mL) | Total Volume (mL) |
|---|---|---|---|
| 4 | 50 mL of 4 mg/mL | 0 | 50 |
| 2 | 25 mL of 4 mg/mL | 25 | 50 |
| 1 | 25 mL of 2 mg/mL | 25 | 50 |
| 0.5 | 25 mL of 1 mg/mL | 25 | 50 |
| 0.1 | 5 ml of 1 mg/mL | 20 | 25 |
| Verification Standard 1.5 mg/mL | 18.75 mL of 4 mg/mL | 31.25 | 50 |

Analysis

Each sample (1 gram) was mixed with reverse osmosis water at 200 rpm and 50° C. overnight. The pH of the sample was adjusted to between 5 and 6 and filtered through a 0.2 μm syringe filter. Samples were stored at −20° C. prior to analysis to maintain integrity of the samples. The observations made during the preparation of the samples are presented in Table 29.

TABLE 29

Observations During HPLC Sample Preparation

| Sample | Amount used (g) | Water added (mL) | pH | Observations |
|---|---|---|---|---|
| P132 | 1 | 30 | 5.38 | Fluffy, difficult to mix |
| P132-10 | 1 | 25 | 6.77 | Fluffy, difficult to mix |
| P132-100 | 1 | 20 | 3.19 | pH is low, difficult to bring to pH 5.0, used 10N NaOH |
| P132-US | 0.3 | 5 | 6.14 | |
| A132 | 1 | 15 | 5.52 | |
| A132-10 | 1 | 15 | 4.9 | |
| A132-100 | 1 | 15 | 5.39 | |
| SG132 | 1 | 15 | 5.59 | |
| SG132-10 | 1 | 15 | 5.16 | |
| SG132-100 | 1 | 15 | 4.7 | |
| SG132-10-US | 0.3 | 5 | 5.12 | |
| SG132-100-US | 0.3 | 5 | 4.97 | |
| WS132 | 1 | 15 | 5.63 | |
| WS132-10 | 1 | 15 | 5.43 | |
| WS132-100 | 1 | 15 | 5.02 | |

*pH of these samples was adjusted to pH using 1N NaOH

Standards were prepared fresh from a 4 mg/mL stock solution of the 6 combined sugars, glucose, xylose, cellobiose, arabinose, mannose, and galactose. The stock solution was prepared by dissolving 0.400 grams of each sugar into 75 mL of nanopure water (0.3 micron filtered). Once dissolved, the stock solution was diluted to 100 mL using a volumetric flask and stored at −20° C. Working standard solutions of 0.1, 0.5, 1, 2, and 4 mg/mL were prepared by serial dilution of the stock solution with nanopure water. In addition, a verification standard of 1.5 mg/mL was also prepared from the stock solution.

Sugar concentrations were analyzed according to the protocol Determination of Structural Carbohydrates in Biomass (NREL Biomass Program, 2006) and this protocol is incorporated herein by reference in its entirety. A SHODEX SUGAR SP0810 COLUMN with an Evaporative Light Scattering Detector was used. A verification standard (1.5 mg/mL of standard) was analyzed every 8 injections to ensure that the integrity of the column and detector were maintained during the experiment. The standard curve coefficient of variation ($R^2$ value) was at least 0.989 and the concentration of the verification standards were within 10% of the actual concentration. The HPLC conditions were as follows:

TABLE 30

HPLC Parameters

| | |
|---|---|
| Injection volume: | 20 μL |
| Mobile phase: | nanopure water*, 0.45 μm filtered and degassed |
| Flow rate: | 0.5 mL/min |
| Column temperature: | 85° C. |
| Detector temperature: | evaporator temperature 110° C., nebulizer temperature 90° C. |

*Initial tests noted that better separation was observed when using nanopure water than 15/85 acetonitrile:water in the mobile phase (manufacturer does not recommend using greater than 20% acetonitrile with this column).

Results

The results of the HPLC analysis are presented in Tables 31, 32, and 33.

TABLE 31

Sugar Concentration Expressed as mg/mL and mg/g of Extract

| Sample ID | Xylose mW ~ 150 $C_5H_{10}O_5$ Mono | | Arabinose mW ~ 150 $C_5H_{10}O_5$ Mono | | Glucose mW ~ 180 $C_6H_{12}O_6$ Mono | | Galactose (see gluc) mg/mL:mg/g | | Mannose (see gluc) mg/mL:mg/g | | Cellobiose mW ~ 342 $C_{12}H_{22}O_{11}$ Disacc | |
|---|---|---|---|---|---|---|---|---|---|---|---|---|
| | mg/mL | mg/g | mg/mL | mg/g | mg/mL | mg/g | mg/mL | mg/g | mg/mL | mg/g | mg/mL | mg/g |
| P | | | | | | | | | | | | |
| P-132 | 0.00 | 0.00 | 0.00 | 0.00 | 0.00 | 0.00 | 0.00 | 0.00 | 0.00 | 0.00 | 0.00 | 0.00 |
| P-132-10 | 0.00 | 0.00 | 0.00 | 0.00 | 0.34 | 8.60 | 0.00 | 0.00 | 0.00 | 0.00 | 00.33 | 8.13 |
| P-132-100 | 0.35 | 7.04 | 0.00 | 0.00 | 0.34 | 6.14 | 0.00 | 0.00 | 0.00 | 0.00 | 0.36 | 7.20 |
| P-132-BR | 0.35 | 5.80 | 0.43 | 7.17 | 0.34 | 5.62 | 0.00 | 0.00 | 0.00 | 0.00 | 0.00 | 0.00 |
| G | | | | | | | | | | | | |
| G-132 | 0.39 | 5.88 | 0.38 | 5.73 | 0.84 | 12.66 | 0.34 | 5.04 | 0.92 | 13.76 | 0.00 | 0.00 |
| G-132-10 | 0.50 | 7.50 | 0.41 | 6.18 | 1.07 | 16.04 | 0.35 | 5.19 | 0.98 | 14.66 | 0.00 | 0.00 |
| G-132-100 | 0.00 | 0.00 | 0.37 | 5.54 | 0.41 | 6.14 | 0.00 | 0.00 | 0.55 | 8.28 | 0.45 | 6.71 |
| G-132-10-US | 0.34 | 5.73 | 0.39 | 6.45 | 0.33 | 5.43 | 0.00 | 0.00 | 0.00 | 0.00 | 0.00 | 0.00 |
| G-132-100-US | 0.00 | 0.00 | 0.37 | 6.22 | 0.35 | 5.90 | 0.33 | 5.43 | 0.40 | 6.70 | 0.39 | 6.45 |
| A | | | | | | | | | | | | |
| A-132 | 1.36 | 20.39 | 0.00 | 0.00 | 1.08 | 16.22 | 0.39 | 5.84 | 1.07 | 16.02 | 0.00 | 0.00 |
| A-132-10 | 1.19 | 17.87 | 0.00 | 0.00 | 0.00 | 0.00 | 0.00 | 0.00 | 0.37 | 5.52 | 0.00 | 0.00 |
| A-132-100 | 1.07 | 16.11 | 0.00 | 0.00 | 0.35 | 5.18 | 0.00 | 0.00 | 0.00 | 0.00 | 0.81 | 12.2 |
| WS | | | | | | | | | | | | |
| WS-132 | 0.49 | 7.41 | 0.41 | 6.15 | 0.39 | 5.90 | 0.00 | 0.00 | 0.00 | 0.00 | 0.00 | 0.00 |
| WS-132-10 | 0.57 | 8.49 | 0.40 | 5.99 | 0.73 | 10.95 | 0.34 | 5.07 | 0.50 | 7.55 | 0.00 | 0.00 |
| WS-132-100 | 0.43 | 6.39 | 0.37 | 5.51 | 0.36 | 5.36 | 0.00 | 0.00 | 0.36 | 5.33 | 0.35 | 5.25 |

TABLE 32

Sugar Concentration Expressed at % of Paper

| Sugar concentration (% of dry sample) | P132 | P132-10 | P132-100 | P132-US |
|---|---|---|---|---|
| cellobiose | 0.00 | 0.81 | 0.72 | 0.00 |
| glucose | 0.00 | 0.86 | 0.67 | 0.56 |
| xylose | 0.00 | 0.00 | 0.70 | 0.58 |
| galactose | 0.00 | 0.00 | 0.00 | 0.00 |
| arabinose | 0.00 | 0.00 | 0.00 | 0.72 |
| mannose | 0.00 | 0.00 | 0.00 | 0.00 |

TABLE 33

Sugar Concentration Expressed at % of Total Sample

| Sugar concentration (% of dry sample) | A132 | A132-10 | A132-100 | SG132 | SG132-10 | SG132-100 | SG132-10-US | SG132-100-US | WS132 | WS132-10 | WS132-100 |
|---|---|---|---|---|---|---|---|---|---|---|---|
| Cellobiose | 0.00 | 0.00 | 1.22 | 0.00 | 0.00 | 0.67 | 0.00 | 0.65 | 0.00 | 0.00 | 0.53 |
| Glucose | 1.62 | 0.00 | 0.52 | 1.27 | 1.60 | 0.61 | 0.54 | 0.59 | 0.59 | 1.10 | 0.54 |
| Xylose | 2.04 | 1.79 | 1.61 | 0.59 | 0.75 | 0.00 | 0.57 | 0.00 | 0.74 | 0.85 | 0.64 |
| Galactose | 0.58 | 0.00 | 0.00 | 0.50 | 0.52 | 0.00 | 0.00 | 0.54 | 0.00 | 0.51 | 0.00 |
| Arabinose | 0.00 | 0.00 | 0.00 | 0.57 | 0.62 | 0.55 | 0.65 | 0.62 | 0.62 | 0.60 | 0.55 |
| Mannose | 1.60 | 0.55 | 0.00 | 1.38 | 1.47 | 0.83 | 0.00 | 0.67 | 0.00 | 0.76 | 0.53 |

Example 16

Toxicity Study

Twelve samples were analyzed for toxicity against a panel of three ethanol-producing cultures. In this study, glucose was added to the samples in order to distinguish between starvation of the cultures and toxicity of the samples. A thirteenth sample was tested for toxicity against *Pichia stipitis*. A summary of the protocol used is listed in Table 32. A description of the chemicals and equipment used in the toxicity testing is reported in Tables 34-36.

TABLE 34

Conditions for Toxicity Testing

| | Organism | | |
|---|---|---|---|
| Variable | *Zymomonas mobilis* ATCC 31821 | *Saccharomyces cerevesiae* ATCC 24858 | *Pichia stipitis* NRRL Y-7124 |
| Test Repetition | | Duplicate | |
| Inoculation Volume (mL) | 1 | 0.1 | 1 |
| Incubation Temperature | 30° C. | 25° C. | 25° C. |
| Shaker Speed (rpm) | 125 | 200 | 125 |
| Erlenmeyer Flask Volume | 250 mL | 500 mL | 250 mL |
| Media volume | 100 mL | 100 mL | 100 mL |
| Total Incubation time (hours) | 36 | 36 | 48 |
| Ethanol Analysis (hours) | 24, 30, 36 | 24, 30, 36 | 24, 36, 48 |
| Cell Counts (hours) | 24, 36 | 24, 36 | 24, 48 |
| pH | 0 hours | 0 hours | 0 hours |

TABLE 35

Reagents Used for Toxicity Testing

| Media Component | Manufacturer | Reference # | Lot # |
|---|---|---|---|
| Urea | ScholAR Chemistry | 9472706 | AD-7284-43 |
| Yeast Nitrogen Base | Becton Dickinson | 291940 | 7128171 |
| Peptone | Becton Dickinson | 211677 | 4303198 |
| Xylose | Fluka | 95731 | 1304473 51707231 |
| Glucose | Sigma | G-5400 | 107H0245 |

TABLE 35-continued

Reagents Used for Toxicity Testing

| Media Component | Manufacturer | Reference # | Lot # |
|---|---|---|---|
| Yeast Extract (used for *S. cerevisiae*) | Becton Dickinson | 288620 | 4026828 |
| Yeast Extract (used for *P. stipitis* and *Z. mobilis*) | Becton Dickinson | 212750 | 7165593 |
| $MgSO_4 \cdot 7H_2O$ | Sigma | M5921 | 034K0066 |
| $(NH_4)_2SO_4$ | Sigma | A4418 | 117K5421 |
| $KH_2PO_4$ | Sigma | P5379 | 074K0160 |
| YM Broth | Becton Dickinson | 271120 | 6278265 |

TABLE 36

YSI Components Used in Shake Flask Study

| Component | Catalog # | Lot # |
|---|---|---|
| YSI Ethanol Membrane | 2786 | 07L100153 |
| YSI Ethanol Standard (3.2 g/L) | 2790 | 012711040 |
| YSI Ethanol Buffer | 2787 | 07M1000053, 07100215 |

Testing was performed using the three microorganisms as described below.

*Saccharomyces cerevisiae* ATCC 24858 (American Type Culture Collection)

A slant of *S. cerevisiae* was prepared from a rehydrated lyophilized culture obtained from ATCC. A portion of the slant material was streaked onto an YM Broth+20 g/L agar (pH 5.0) and incubated at 30° C. for 2 days. A 250 mL Erlenmeyer flask containing 50 mL of medium (20 g/L glucose, 3 g/L yeast extract, and 5.0 g/L peptone, pH 5.0) was inoculated with one colony from the YM plate and incubated for 24 hours at 25° C. and 200 rpm. After 23 hours of growth, a sample was taken and analyzed for optical density (600 nm in a UV spectrophotometer) and purity (Gram stain). Based on these results, one flask (called the Seed Flask) with an OD of 14.8 and clean Gram Stain was chosen to inoculate all of the test flasks.

The test vessels were 500 mL Erlenmeyer flasks containing 100 mL of the sterile medium described above. All flasks were autoclaved at 121° C. and 15 psi prior to the addition of the test materials. The test materials were not sterilized, as autoclaving will change the content of the samples. The test samples were added at the time of inoculation (rather than prior to) to reduce the possibility of contamination. In addition to the test samples, 1 mL (1% v/v) of seed flask material was added to each flask. The flasks were incubated as described above for 36 hours.

Pichia stipitis NRRL Y-7124 (ARS Culture Collection)

A slant of P. stipitis was prepared from a rehydrated lyophilized culture obtained from ARS Culture Collection. A portion of the slant material was streaked onto an YM Broth+ 20 g/L agar (pH 5.0) and incubated at 30° C. for 2 days. A 250 mL Erlenmeyer flask containing 100 mL of medium (40 g/L glucose, 1.7 g/L yeast nitrogen base, 2.27 g/L urea, 6.56 g/L peptone, 40 g/L xylose, pH 5.0) was inoculated with a small amount of plate material and incubated for 24 hours at 25° C. and 125 rpm. After 23 hours of growth, a sample was taken and analyzed for optical density (600 nm in a UV spectrophotometer) and purity (Gram stain). Based on these results, one flask (called the Seed Flask) at an optical density of 5.23 and with a clean Gram Stain was chosen to inoculate all of the test flasks.

The test vessels were 250 mL Erlenmeyer flasks containing 100 mL of the sterile medium described above. All flasks were autoclaved empty at 121° C. and 15 psi and filter sterilized (0.22 μm filter) media added to the flasks prior to the addition of the test materials. The test materials were not sterilized, as autoclaving will change the content of the samples and filter sterilization not appropriate for sterilization of solids. The test samples were added at the time of inoculation (rather than prior to) to reduce the possibility of contamination. In addition to the test samples, 1 mL (1% v/v) of seed flask material was added to each flask. The flasks were incubated as described above for 48 hours.

Zymomonas mobilis ATCC 31821 (American Type Culture)

A slant of Z. mobilis was prepared from a rehydrated lyophilized culture obtained from ATTC. A portion of the slant material was streaked onto DYE plates (glucose 20 g/L, Yeast Extract 10 g/L, Agar 20 g/L, pH 5.4) and incubated at 30° C. and 5% $CO_2$ for 2 days. A 20 mL screw-cap test tube containing 15 mL of medium (25 g/L glucose, 10 g/L yeast extract, 1 g/L $MgSO_4 \cdot 7H_2O$, 1 g/L $(NH_4)_2SO_4$, 2 g/L $KH_2PO_4$, pH 5.4) was inoculated with one colony and incubated for 24 hours at 30° C. with no shaking. After 23 hours of growth, a sample was taken and analyzed for optical density (600 nm in a UV spectrophotometer) and purity (gram stain). Based on these results, one tube (OD 1.96) was chosen to inoculate the second seed flask. The second seed flask was a 125 ml flask containing 70 mL of the media described above and was inoculated with 700 μL (1% v/v) and incubated for 24 hours at 30° C. with no shaking. After 23 hours of growth, a sample was taken and analyzed for optical density (600 nm in a UV spectrophotometer) and purity (gram stain). Based on these results, one flask (called the Seed Flask) with an OD of 3.72 was chosen to inoculate all of the test flasks.

The test vessels were 250 mL Erlenmeyer flasks containing 100 mL of the sterile medium described above with the exception of yeast extract at 5 g/L. All flasks were autoclaved empty at 121° C. and 15 psi and filter sterilized (0.22 μm filter) media added to the flasks prior to the addition of the test materials. The test materials were not sterilized, as autoclaving will change the content of the samples and filter sterilization not appropriate for sterilization of solids. The test samples were added at the time of inoculation to reduce the possibility of contamination. In addition to the test samples, 1 mL (1% v/v) of seed flask material was added to each flask. The flasks were incubated as described above for 36 hours Analysis Two samples were analyzed for cell concentration (using spread plating for Z. mobilis and direct counts (haemocytometer and microscope for S. cerevisiae and P. stipitis). Appropriately diluted samples of Z. mobilis were spread on Dextrose Yeast Extract (glucose 20 g/L, Yeast Extract 10 g/L, Agar 20 g/L, pH 5.4) plates, incubated at 30° C. and 5% CO2 for 2 days, and the number of colonies counted. Appropriately diluted samples of S. cerevisiae and P. stipitis were mixed with 0.05% Trypan blue, loaded into a Neubauer haemocytometer. The cells were counted under 40× magnification.

Three samples were analyzed for ethanol concentration using the YSI Biochem Analyzer based on the alcohol dehydrogenase assay (YSI, Interscience). Samples were centrifuged at 14,000 rpm for 20 minutes and the supernatant stored at −20° C. to preserve integrity. The samples were diluted to between 0-3.2 g/L ethanol prior to analysis. A standard of 3.2 g/L ethanol was analyzed approximately every 30 samples to ensure the integrity of the membrane was maintained during analysis. The optical density (600 nm) of the samples is not reported because the solid test samples interfered with absorbance measurement by increasing the turbidity of the samples and are inaccurate.

Results of Ethanol Analysis

Performance was used to compare each sample to the control for each microorganism (Tables 37-39). However, the % performance cannot be used to compare between strains. When comparing strains, the total concentration of ethanol should be used. When analyzing the data, a % performance of less than 80% may indicate toxicity when accompanied by low cell number. The equation used to determine % performance is:

% Performance=(ethanol in the sample/ethanol in control)×100

TABLE 37

Ethanol Concentration and % Performance Using Saccharomyces cerevisiae

| | 24 hours | | 30 hours | | 36 hours | |
|---|---|---|---|---|---|---|
| Sample # | Ethanol Concentration (g/L) | % Performance | Ethanol Concentration (g/L) | % Performance | Ethanol Concentration (g/L) | % Performance |
| P132 | 4.0 | 140 | 5.2 | 127 | 3.26 | 176 |
| P132-10 | 4.2 | 147 | 5.1 | 125 | 3.86 | 209 |
| P132-100 | 4.3 | 149 | 5.6 | 136 | 3.47 | 187 |
| A132 | 5.5 | 191 | 6.5 | 160 | 5.24 | 283 |

TABLE 37-continued

Ethanol Concentration and % Performance Using *Saccharomyces cerevisiae*

| Sample # | 24 hours Ethanol Concentration (g/L) | 24 hours % Performance | 30 hours Ethanol Concentration (g/L) | 30 hours % Performance | 36 hours Ethanol Concentration (g/L) | 36 hours % Performance |
|---|---|---|---|---|---|---|
| A132-10 | 1.9 | 67 | 6.3 | 153 | 5.54 | 299 |
| A132-100 | 4.4 | 154 | 5.6 | 137 | 4.04 | 218 |
| G132 | 5.3 | 186 | 6.0 | 146 | 3.99 | 215 |
| G132-10 | 5.2 | 180 | 6.4 | 156 | 4.63 | 250 |
| G132-100 | 5.5 | 191 | 6.3 | 155 | 4.60 | 248 |
| WS132 | 4.8 | 168 | 6.3 | 155 | 4.51 | 244 |
| WS132-10 | 4.9 | 172 | 6.0 | 146 | 4.55 | 246 |
| WS132-100 | 4.9 | 170 | 5.7 | 140 | 4.71 | 254 |
| Control | 2.9 | 100 | 4.1 | 100 | 1.85 | 100 |

TABLE 38

Ethanol Concentration and % Performance Using *Pichia stipitis*

| Sample # | 24 hours Ethanol Concentration (g/L) | 24 hours % Performance | 36 hours Ethanol Concentration (g/L) | 36 hours % Performance | 48 hours Ethanol Concentration (g/L) | 48 hours % Performance |
|---|---|---|---|---|---|---|
| P132 | 2.8 | 130 | 3.4 | 188 | 8.1 | 176 |
| P132-10 | 7.3 | 344 | 11.9 | 655 | 15.8 | 342 |
| P132-100 | 5.2 | 247 | 8.6 | 472 | 13.3 | 288 |
| A132 | 12.2 | 575 | 14.7 | 812 | 14.9 | 324 |
| A132-10 | 15.1 | 710 | 18.7 | 1033 | 26.0 | 565 |
| A132-100 | 10.9 | 514 | 16.7 | 923 | 22.2 | 483 |
| G132 | 8.0 | 375 | 12.9 | 713 | 13.3 | 288 |
| G132-10 | 10.1 | 476 | 16.0 | 884 | 22.3 | 485 |
| G132-100 | 8.6 | 406 | 15.2 | 837 | 21.6 | 470 |
| WS132 | 9.8 | 460 | 14.9 | 820 | 17.9 | 389 |
| WS132-10 | 7.8 | 370 | 16.1 | 890 | 19.3 | 418 |
| WS132-100 | 9.1 | 429 | 15.0 | 829 | 15.1 | 328 |
| Sample A* | 13.2 | 156 | 19.0 | 166 | 20.6 | 160 |
| Control | 2.1 | 100 | 1.8 | 100 | 4.6 | 100 |

Samples in BOLD were the highest ethanol producers, over 20 g/L and similar to the concentrations in wood hydrolyzates (H.K. Sreenath and T.W. Jeffries Bioresource Technology 72 (2000) 253-260).
*Analyzed in later shake flask experiment.

TABLE 39

Ethanol Concentration and % Performance Using *Zymomonas mobilis*

| Sample # | 24 hours Ethanol Concentration (g/L) | 24 hours % Performance | 30 hours Ethanol Concentration (g/L) | 30 hours % Performance | 36 hours Ethanol Concentration (g/L) | 36 hours % Performance |
|---|---|---|---|---|---|---|
| P132 | 7.5 | 85 | 6.8 | 84 | 7.5 | 93 |
| P132-10 | 7.5 | 85 | 4.8 | 59 | 6.8 | 84 |
| P132-100 | 7.3 | 83 | 6.2 | 77 | 7.1 | 88 |
| A132 | 9.6 | 109 | 8.3 | 103 | 9.1 | 112 |
| A132-10 | 9.2 | 105 | 8.4 | 105 | 8.8 | 109 |
| A132-100 | 8.2 | 93 | 7.6 | 94 | 7.6 | 93 |
| WS132 | 7.9 | 89 | 7.1 | 88 | 7.7 | 94 |
| WS132-10 | 8.2 | 93 | 6.8 | 85 | 7.3 | 90 |
| WS132-100 | 8.7 | 98 | 6.9 | 86 | 8.3 | 102 |
| G132 | 8.7 | 99 | 7.1 | 88 | 8.1 | 99 |
| G132-10 | 7.8 | 88 | 7.0 | 88 | 7.3 | 90 |
| G132-100 | 8.6 | 98 | 7.8 | 98 | 8.3 | 102 |
| Control | 8.8 | 100 | 8.0 | 100 | 8.1 | 100 |

Results from Cell Concentration Analysis

% Cells is used to compare each sample to the control for each organism (Tables 40-42). However, the % cells cannot be used to compare between strains. When comparing strains, the total concentration of cells should be used. When analyzing the data, a % performance of less than 70% may indicate toxicity when accompanied by low ethanol concentration. The equation used to determine % performance is:

% cells=(number of cell in the sample/number of cells in control)×100

TABLE 40

Results from Cell Concentration Analysis for *Saccharomyces cerevisiae*

| | 24 hours | | 36 hours | |
| --- | --- | --- | --- | --- |
| Sample # | Cell Concentration ($\times 10^8$/mL) | % Cells | Cell Concentration ($\times 10^8$/mL) | % Cells |
| P132 | 1.99 | 166 | 2.51 | 83 |
| P132-10 | 2.51 | 209 | 1.91 | 63 |
| P132-100 | 1.35 | 113 | 1.99 | 66 |
| A132 | 3.80 | 316 | 2.59 | 85 |
| A132-10 | 1.73 | 144 | 3.90 | 129 |
| A132-100 | 3.98 | 331 | 2.51 | 83 |
| G132 | 2.14 | 178 | 3.12 | 103 |
| G132-10 | 2.33 | 194 | 2.59 | 85 |
| G132-100 | 3.57 | 298 | 2.66 | 88 |
| WS132 | 4.10 | 341 | 2.66 | 88 |
| WS132-10 | 2.63 | 219 | 2.81 | 93 |
| WS132-100 | 2.29 | 191 | 2.40 | 79 |
| Control | 1.20 | 100 | 3.03 | 100 |

TABLE 41

Results from Cell Concentration Analysis for *Pichia stipitis*

| | 24 hours | | 48 hours | |
| --- | --- | --- | --- | --- |
| Sample # | Cell Concentration ($\times 10^8$/mL) | % Cells | Cell Concentration ($\times 10^8$/mL) | % Cells |
| P132 | 16.4 | 108 | 20.3 | 87 |
| P132-10 | 11.5 | 76 | 9.5 | 41 |
| P132-100 | 6.5 | 43 | 17.8 | 76 |
| A132 | 7.1 | 47 | 10.2 | 44 |
| A132-10 | 12.7 | 84 | 9.3 | 40 |
| A132-100 | 11.8 | 78 | 18.3 | 78 |
| G132 | 4.5 | 30 | 4.8 | 21 |
| G132-10 | 22.8 | 151 | 9.8 | 42 |
| G132-100 | 10.1 | 67 | 21.7 | 93 |
| WS132 | 17.6 | 117 | 8.2 | 35 |
| WS132-10 | 5.3 | 35 | 10.8 | 46 |
| WS132-100 | 9.3 | 62 | 10.7 | 46 |
| Control | 15.1 | 100 | 23.4 | 100 |

TABLE 42

Results from Cell Concentration Analysis for *Zymomonas mobilis*

| | 24 hours | | 36 hours | |
| --- | --- | --- | --- | --- |
| Sample # | Cell Concentration ($\times 10^8$/mL) | % Cells | Cell Concentration ($\times 10^8$/mL) | % Cells |
| P132 | 7.08 | 86 | 2.97 | 66 |
| P132-10 | 21.80 | 264 | 4.37 | 98 |
| P132-100 | 4.50 | 54 | 3.35 | 75 |
| A132 | 6.95 | 84 | 1.99 | 44 |
| A132-10 | 6.13 | 74 | 4.05 | 91 |
| A132-100 | 9.60 | 116 | 4.20 | 94 |
| G132 | 7.48 | 90 | 3.84 | 86 |
| G132-10 | 14.75 | 178 | 2.89 | 65 |
| G132-100 | 6.00 | 72 | 2.55 | 57 |
| WS132 | 9.70 | 117 | 4.55 | 102 |
| WS132-10 | 13.20 | 160 | 4.32 | 97 |
| WS132-100 | 5.15 | 62 | 2.89 | 65 |
| Control | 8.27 | 100 | 4.47 | 100 |

Example 17

Shake Flask Fermentation of Cellulose Samples Using *P. stipitis*

Summary

Thirteen samples were tested for ethanol production in *P. stipitis* culture without sugar added. They were tested in the presence and absence of cellulase (Accellerase 1000® enzyme complex, Genencor). Equipment and reagents used for the experiment are listed below in Tables 43-45.

TABLE 43

Equipment and frequency of maintenance

| Equipment | Manufacturer | Frequency of Maintenance |
| --- | --- | --- |
| Shakers (2) | B. Braun Biotech, Certomat BS-1 | Quarterly |
| Spectrophotometer | Unicam, UV300 | Biannual |
| YSI Biochem Analyzer | Interscience, YSI | Monthly |

TABLE 44

YSI Components used in shake flask study

| Component | Catalog # | Lot # |
| --- | --- | --- |
| YSI Ethanol Membrane | 2786 | 07L100153 |
| YSI Ethanol Standard (3.2 g/L) | 2790 | 012711040 |
| YSI Ethanol Buffer | 2787 | 07M1000053, 07100215 |

TABLE 45

Chemicals used for shake flask fermentation

| Media Component | Manufacturer | Reference # | Lot # |
| --- | --- | --- | --- |
| Urea | ScholAR Chemistry | 9472706 | AD-7284-43 |
| Yeast Nitrogen Base | Becton Dickinson | 291940 | 7128171 |
| Peptone | Becton Dickinson | 211677 | 4303198 |
| YM Broth | Becton Dickinson | 271120 | 6278265 |
| Accellerase ® Enzyme complex | Genencor | Accellerase ® 1000 | 1600794133 |
| Xylose | BioChemika | 95731 | 1304473 51707231 |
| Glucose | Sigma | G-5400 | 107H0245 |

A slant of *P. stipitis* NRRL Y-7124 was prepared from a rehydrated lyophilized culture obtained from ARS Culture Collection. A portion of the slant material was streaked onto a Yeast Mold (YM) Broth+20 g/L agar (pH 5.0) and incubated at 30° C. for 2 days. A 250 mL Erlenmeyer flask containing 100 mL of medium (40 g/L glucose, 1.7 g/L yeast nitrogen base, 2.27 g/L urea, 6.56 g/L peptone, 40 g/L xylose, pH 5.0) was inoculated with one colony and incubated for 24 hours at 25° C. and 100 rpm. After 23 hours of growth, a sample was taken and analyzed for optical density (600 nm in a UV spectrophotometer) and purity (Gram stain). Based on these results, one flask (called the Seed Flask) at an optical density of 6.79 and with a clean Gram stain was chosen to inoculate all of the test flasks.

The test vessels were 250 mL Erlenmeyer flasks containing 100 mL of medium (1.7 g/L yeast nitrogen base, 2.27 g/L urea, and 6.56 g/L peptone). No sugar (glucose or xylose) was added to the growth flask medium. All flasks were autoclaved empty at 121° C. and 15 psi and filter sterilized (0.22 μm filter) media added to the flasks prior to the addition of the test materials. The test materials were not sterilized, as autoclaving will change the content of the samples and filter sterilization is not appropriate for sterilization of solids. The test samples (listed in Table 46) were added at the time of inoculation (rather than prior to) to reduce the possibility of contamination. In addition to the test samples, 1 mL (1% v/v) of seed flask material was added to each flask. Flasks containing sample P132-100 required the addition of 0.4 mL 1 M NaOH to bring the pH to 5.0. The flasks were incubated at 30° C. and 150 rpm above for 96 hours.

One set of duplicate flasks per feedstock contained Accellerase® enzyme complex (1.25 mL per flask, highest recommended dosage is 0.25 mL per gram of biomass, Genencor) to attempt simultaneous saccharification and fermentation (SSF). The other set of duplicate flasks did not contain Accellerase® enzyme complex. A total of 52 flasks were analyzed.

Six control flasks were also analyzed. Positive control flasks contained SolkaFloc 200 NF Powdered Cellulose (lot # UA158072, International Fiber Corporation) at a concentration of 2.5 grams per 100 mL flask (25 grams per L) with and without addition of Accellerase® enzyme complex. In addition, a control containing sugars (glucose and xylose) only was used.

TABLE 46

The amount of each feedstock added to each flask

| Xyleco Number | Amount added to Flask (g/100 mL) |
|---|---|
| P132 | 2.5 |
| P132-10 | 2.5 |
| P132-100 | 2.5 |
| A132 | 5 |
| A132-10 | 5 |
| A132-100 | 5 |
| G132 | 5 |
| G132-10 | 5 |
| G132-100 | 5 |
| WS132 | 5 |
| WS132-10 | 5 |
| WS132-100 | 5 |
| Sample A | 5 |

Analysis

Samples were analyzed for ethanol concentration (Tables 47, 48, and 49) using the YSI Biochem Analyzer based on the alcohol dehydrogenase assay (YSI, Interscience). Samples were centrifuged at 14,000 rpm for 20 minutes and the supernatant stored at −20° C. The samples were diluted to between 0-3.2 g/L ethanol prior to analysis. A standard of 2.0 g/L ethanol was analyzed approximately every 30 samples to ensure the integrity of the membrane was maintained during analysis.

Results

TABLE 47

Results of Control Flasks

| Control | Ethanol Concentration (g/L) | | | |
|---|---|---|---|---|
| | 24 hours | 36 hours | 48 hours | 96 hours |
| Containing Glucose, no cellulose, no enzyme | 13.20 | 19.00 | 20.60 | 21.60 |
| Containing Crystalline Cellulose (Solka Floc), no sugar, no enzyme | 0.00 | 0.00 | 0.00 | 0.00 |
| Containing Crystalline Cellulose (Solka Floc) at 25 g/L, no sugar, Accellerase ® added | 6.56 | 7.88 | 9.80 | 8.65 |

TABLE 48

Results of Shake Flasks without Accellerase ® 1000 Enzyme Complex

| Sample Number | Ethanol Concentration (g/L) | | | |
|---|---|---|---|---|
| | 24 hours | 36 hours | 48 hours | 96 hours |
| P132 | 0.09 | 0.00 | 0.00 | 0.12 |
| P132-10 | 0.02 | 0.01 | 0.02 | 0.17 |
| P132-100 | 0.09 | 0.01 | 0.00 | 0.02 |
| A132 | 1.74 | 1.94 | 2.59 | 3.70 |
| A132-10 | 1.82 | 2.36 | 2.30 | 2.96 |
| A132-100 | 0.30 | 0.73 | 1.31 | 2.38 |
| G132 | 0.40 | 0.09 | 0.24 | 0.42 |
| G132-10 | 0.69 | 0.42 | 0.22 | 0.24 |
| G132-100 | 0.19 | 0.05 | 0.05 | 0.21 |
| WS132 | 0.47 | 0.50 | 0.68 | 0.65 |
| WS132-10 | 0.47 | 0.49 | 0.34 | 0.92 |
| WS132-100 | 0.14 | 0.07 | 0.08 | 0.22 |
| Sample A | 1.88 | 1.89 | 2.30 | 3.28 |

TABLE 49

Results of Shake Flasks with Accellerase ® 1000 Enzyme Complex

| Sample Number | Ethanol Concentration (g/L) | | | |
|---|---|---|---|---|
| | 24 hours | 36 hours | 48 hours | 96 hours |
| P132 | 7.04 | 8.72 | 9.30 | 5.80 |
| P132-10 | 4.22 | 4.48 | 4.49 | 1.24 |
| P132-100 | 3.18 | 4.28 | 4.70 | 3.35 |
| A132 | 2.79 | 2.91 | 2.03 | 4.30 |
| A132-10 | 3.31 | 1.62 | 2.11 | 2.71 |
| A132-100 | 2.06 | 1.92 | 1.02 | 1.47 |
| G132 | 0.87 | 0.40 | 0.32 | 0.44 |
| G132-10 | 1.38 | 1.04 | 0.63 | 0.07 |
| G132-100 | 2.21 | 2.56 | 2.34 | 0.12 |
| WS132 | 1.59 | 1.47 | 1.07 | 0.99 |
| WS132-10 | 1.92 | 1.18 | 0.73 | 0.23 |
| WS132-100 | 2.90 | 3.69 | 3.39 | 0.27 |
| Sample A | 2.21 | 2.35 | 3.39 | 2.98 |

Example 18

Cellulase Assay

Summary

Thirteen samples were tested for cellulase susceptibility using an industry cellulase (Accellerase® 1000, Genencor) under optimum conditions of temperature and pH.

Protocol

The protocol is a modification of the NREL "Laboratory Analytical Procedure LAP-009 Enzymatic Saccharification of Lignocellulosic Biomass". A sample of material was added to 10 mL 0.1 M sodium citrate buffer (pH 4.8) and 40 mg/mL tetracycline (to prevent growth of bacteria) in a 50 mL tube in duplicate. The amount of sample added to each tube is listed in Table 50. Some samples were difficult to mix (P132, P132-10, P132-100), so were added at a lower concentration. A positive control of 0.2 grams SolkaFloc 200 NF Powdered Cellulose (lot # UA158072, International Fiber Corporation) and a negative control (no sample) were also included. Enough reverse osmosis (RO) water to bring the volume to a total of 20 mL was added to the tubes. Both the sodium citrate buffer and water were heated to 50° C. prior to use.

Accellerase® 1000 enzyme was added to each tube at a dosage of 0.25 mL per gram of biomass (highest dosage recommended by Genencor). The tubes were incubated at 45° angle at 150 rpm and 50 degrees C. (recommended by Genencor) for 72 hours. Samples were taken at 0, 3, 6, 9, 12, 18, 24, 48, and 72 hours (Table 52 and 53), centrifuged at 14,000 rpm for 20 minutes and the supernatant frozen at −20° C. The glucose concentration in the samples was analyzed using the YSI Biochem Analyzer (Interscience) using the conditions described in Table 51. A glucose standard solution of 2.5 g/L was prepared by dissolving 2.500 grams glucose (Sigma Cat# G7528-5KG, Lot#:107H0245) in distilled water. Once dissolved, the total volume was brought to 1 L with distilled water in a volumetric flask. The standard was prepared fresh weekly and stored at 4° C.

TABLE 50

Amount of Each Sample Added

| Xyleco Number | Amount added to Tube (g/20 mL) |
|---|---|
| P132 | 0.5 |
| P132-10 | 0.5 |
| P132-100 | 0.5 |
| A132 | 0.75 |
| A132-10 | 0.75 |
| A132-100 | 0.75 |
| G132 | 0.75 |
| G132-10 | 0.75 |
| G132-100 | 0.75 |
| WS132 | 0.75 |
| WS132-10 | 0.75 |
| WS132-100 | 0.75 |
| Sample A | 0.75 |
| SolkaFloc 200NF (Control) | 0.2 |
| Negative Control | 0 |

TABLE 51

YSI Components Used in Shake Flask Study

| Component | Catalog # | Lot # |
|---|---|---|
| YSI Glucose Membrane | 2365 | 07D100124 |
| YSI Glucose Buffer | 2357 | 014614A |

Results

TABLE 52

Cellulase Assay Results

| Sample Number | Glucose Concentration (mg/mL) at Incubation Time (hours) | | | | | | | | |
|---|---|---|---|---|---|---|---|---|---|
| | 0 | 3 | 6 | 9 | 12 | 18 | 24 | 48 | 72 |
| P132 | 0.59 | 4.19 | 7.00 | 8.72 | 9.70 | 10.95 | 12.19 | 15.10 | 15.65 |
| P132-10 | 0.36 | 3.37 | 5.08 | 6.39 | 6.98 | 7.51 | 8.99 | 11.25 | 11.65 |
| P132-100 | 0.91 | 3.86 | 5.67 | 7.31 | 8.08 | 9.47 | 10.70 | 12.70 | 13.80 |
| A132 | 0.39 | 1.51 | 1.92 | 2.40 | 2.64 | 3.04 | 3.30 | 3.90 | 4.06 |
| A132-10 | 0.42 | 1.80 | 2.27 | 2.63 | 2.86 | 3.16 | 3.43 | 4.02 | 4.14 |
| A132-100 | 0.46 | 2.09 | 2.72 | 3.16 | 3.43 | 3.78 | 4.09 | 4.84 | 5.26 |
| G132 | 0.40 | 1.16 | 1.35 | 1.52 | 1.60 | 1.67 | 1.85 | 2.10 | 2.21 |
| G132-10 | 0.34 | 1.34 | 1.64 | 1.95 | 2.03 | 2.09 | 2.36 | 2.77 | 3.02 |
| G132-100 | 0.61 | 1.84 | 2.32 | 2.89 | 3.14 | 3.52 | 3.97 | 4.81 | 5.44 |
| WS132 | 0.35 | 1.48 | 1.81 | 2.14 | 2.26 | 2.50 | 2.70 | 3.18 | 3.26 |
| WS132-10 | 0.44 | 1.77 | 2.22 | 2.60 | 2.76 | 2.61 | 3.15 | 3.62 | 3.82 |
| WS132-100 | 0.70 | 2.76 | 3.63 | 4.59 | 4.78 | 5.29 | 5.96 | 6.99 | 7.43 |
| Sample A | 0.42 | 1.09 | 1.34 | 1.55 | 1.69 | 1.66 | 2.17 | 2.96 | 3.71 |
| Negative Control (no sample) | 0.03 | 0.03 | 0.01 | 0.01 | 0.02 | 0.01 | 0.02 | 0.02 | 0.02 |
| Positive Control (SolkaFloc) | 0.17 | 2.38 | 3.65 | 4.71 | 5.25 | 5.98 | 7.19 | 9.26 | 9.86 |

The amount of cellulose digested in the tube was calculated as follows:

g/mL glucose×20 mL (volume of sample)×0.9 (to correct for the water molecule added upon hydrolysis of cellulose)

The percent of the total sample released as glucose (in Table 53 below) was calculated as follows:

g of cellulose digested/g of sample added (see Table 5 for details)*100

TABLE 53

Cellulase Assay Results

| Sample Number | Percent of the Total Sample Released as Glucose (%) at Incubation Time (h) | | | | | | | | |
|---|---|---|---|---|---|---|---|---|---|
| | 0 | 3 | 6 | 9 | 12 | 18 | 24 | 48 | 72 |
| P132 | 2.02 | 14.98 | 25.16 | 31.36 | 34.85 | 39.38 | 43.81 | 54.29 | 56.27 |
| P132-10 | 1.19 | 12.02 | 18.25 | 22.97 | 25.06 | 27.00 | 32.29 | 40.43 | 41.87 |
| P132-100 | 3.17 | 13.79 | 20.38 | 26.28 | 29.02 | 34.06 | 38.45 | 45.65 | 49.61 |
| A132 | 0.86 | 3.55 | 4.58 | 5.74 | 6.29 | 7.27 | 7.87 | 9.31 | 9.70 |
| A132-10 | 0.94 | 4.25 | 5.42 | 6.29 | 6.82 | 7.56 | 8.18 | 9.60 | 9.89 |
| A132-100 | 1.03 | 4.94 | 6.50 | 7.56 | 8.18 | 9.05 | 9.77 | 11.57 | 12.58 |
| G132 | 0.89 | 2.71 | 3.22 | 3.62 | 3.79 | 3.98 | 4.39 | 4.99 | 5.26 |
| G132-10 | 0.74 | 3.14 | 3.91 | 4.66 | 4.82 | 4.99 | 5.62 | 6.60 | 7.20 |
| G132-100 | 1.39 | 4.34 | 5.54 | 6.91 | 7.49 | 8.42 | 9.48 | 11.50 | 13.01 |
| WS132 | 0.77 | 3.48 | 4.32 | 5.11 | 5.38 | 5.98 | 6.43 | 7.58 | 7.78 |
| WS132-10 | 0.98 | 4.18 | 5.30 | 6.22 | 6.58 | 6.24 | 7.51 | 8.64 | 9.12 |
| WS132-100 | 1.61 | 6.55 | 8.69 | 10.99 | 11.42 | 12.67 | 14.26 | 16.73 | 17.78 |
| Sample A | 0.94 | 2.54 | 3.19 | 3.70 | 4.01 | 3.96 | 5.16 | 7.06 | 8.86 |
| Positive Control (SolkaFloc) | 1.29 | 21.15 | 32.72 | 42.30 | 47.07 | 53.73 | 64.53 | 83.16 | 88.56 |

Example 19

Shake Flask Fermentation Using *Pichia stipitis*

Summary

Shake flask fermentation using *Pichia stipitis* was performed using four cellulosic materials having the highest % performance from Table 36.

Protocol

Experiments were run under the parameters outlined in Tables 54-56.

TABLE 54

Equipment and Frequency of Maintenance

| Equipment | Manufacturer, Name | Frequency of Maintenance |
|---|---|---|
| Shakers (2) | B. Braun Biotech, Certomat BS-1 | Quarterly |
| Spectrophotometer | Unicam, UV300 | Biannual |
| YSI Biochem Analyzer | Interscience, YSI | Monthly |

TABLE 55

YSI Components Used in Shake Flask Study

| Component | Reference # | Lot # |
|---|---|---|
| YSI Ethanol Membrane | 2786 | 07M100361 |
| YSI Ethanol Standard (3.2 g/L) | 2790 | 1271040 |
| YSI Ethanol Buffer | 2787 | 07J100215 |

TABLE 56

Chemicals Used for Shake Flask Fermentation

| Media Component | Manufacturer | Reference # | Lot # |
|---|---|---|---|
| Urea | ScholAR Chemistry | 9472706 | AD-7284-43 |
| Yeast Nitrogen Base | Becton Dickinson | 291940 | 7128171 |
| Peptone | Becton Dickinson | 211677 | 4303198 |

TABLE 56-continued

Chemicals Used for Shake Flask Fermentation

| Media Component | Manufacturer | Reference # | Lot # |
|---|---|---|---|
| YM Broth | Becton Dickinson | 271120 | 6278265 |
| Xylose | Alfa Aesar | A10643 | 10130919 |
| Glucose | Fisher Scientific | BP350-1 | 030064 |

Seed Development

For all the following shake flask experiments the seed flasks were prepared using the following procedure.

A working cell bank of *P. stipitis* NRRL Y-7124 was prepared from a rehydrated lyophilized culture obtained from ARS Culture Collection. Cryovials containing *P. stipitis* culture in 15% v/v glycerol were stored at −75° C. A portion of the thawed working cell bank material was streaked onto a Yeast Mold (YM) Broth+20 g/L agar (pH 5.0) and incubated at 30° C. for 2 days. The plates were held for 2 days at 4° C. before use. A 250 mL Erlenmeyer flask containing 100 mL of medium (40 g/L glucose, 1.7 g/L yeast nitrogen base, 2.27 g/L urea, 6.56 g/L peptone, 40 g/L xylose, pH 5.0) was inoculated with one colony and incubated for 24 hours at 25° C. and 100 rpm. After 23 hours of growth, a sample was taken and analyzed for optical density (600 nm in a UV spectrophotometer) and purity (Gram stain). Based on these results, one flask (called the Seed Flask) at an optical density of between 4 and 8 and with a clean Gram stain was used to inoculate all of the test flasks.

Three experiments were run using samples A132-10, A132-100, G132-10, and G132-100. Experiment #1 tested these four samples for ethanol concentration at varying concentrations of xylose and at constant concentrations of glucose. Experiment #2 tested these four samples for ethanol concentration at double the concentration of feedstock used in the experiments of Table 36. Finally, experiment #3 tested these four samples for ethanol concentration while varying both the xylose and the glucose concentrations, simultaneously.

Experiment #1—Varying the Xylose Concentration

Four cellulosic samples (A132-10, A132-100, G132-10, and G132-100) were tested at varying xylose concentrations as listed in Table 57 below.

TABLE 57

Media Composition of Experiment #1 Flasks

| Treatment | Xylose Concentration (g/L) | Glucose Concentration (g/L) |
|---|---|---|
| 100% Xylose | 40.0 | 40.0 |
| 50% Xylose | 20.0 | 40.0 |
| 25% Xylose | 10.0 | 40.0 |
| 10% Xylose | 4.0 | 40.0 |
| 0% Xylose | 0.0 | 40.0 |

The test vessels (a total of 40, 250 mL Erlenmeyer flasks) contained 100 mL of medium. Five different types of media were prepared with the amount of xylose and glucose outlined in Table 57. In addition, the media contained 1.7 g/L yeast nitrogen base (Becton Dickinson #291940) 2.27 g/L urea (ScholAR Chemistry #9472706), and 6.56 g/L peptone (Becton Dickinson #211677). All flasks were autoclaved empty at 121° C. and 15 psi and filter sterilized (0.22 μm filter) media was added to the flasks prior to the addition of the test materials. Flasks were held at room temperature for 4 days and inspected for contamination (cloudiness) prior to use. The test materials were not sterilized, as autoclaving will change the content of the samples and filter sterilization not appropriate for sterilization of solids. The test samples (A132-10, A132-100, G132-10, and G132-100 at 5 g per 100 mL) were added at the time of inoculation (rather than prior to) to reduce the possibility of contamination. In addition to the test samples, 1 mL (1% v/v) of seed flask material was added to each flask. The flasks were incubated at 30° C. and 150 rpm for 72 hours.

Unfortunately, one flask (sample A132-100 with 100% Xylose) was broken during the testing. Therefore, all results past 24 hours of incubation are reported as a single flask. After 72 hours of incubation, 100% of the original amount of cellulosic material (5.0 g) was added to the 100% Xylose flasks (7 flasks in total, one flask containing sample A132-100 was broken) and incubated as above for an additional 48 hours.

TABLE 58

Addition of Feedstock to 100% Xylose Flasks at Incubation Time 72 hours

| Feedstock | Added at 72 hours (grams) |
|---|---|
| A132-10 | 5 |
| A132-100 | 5 |
| G132-10 | 5 |
| G132-100 | 5 |

Analysis

Samples were taken from the 40 test flasks at incubation times of 0, 6, 12, 24, 36, 48, and 72 hours. In addition, samples were taken at 24 and 48 hours post-addition of the second feedstock amount in the 100% Xylose flasks (see Table 58).

A total of 292 samples were analyzed for ethanol concentration using a YSI Biochem Analyzer based on the alcohol dehydrogenase assay (YSI, Interscience). Samples were centrifuged at 14,000 rpm for 20 minutes and the supernatant stored at −20° C. Of note, time 0 samples required filtration through a 0.45 μm syringe filter. The samples will be diluted to between 0-3.2 g/L ethanol prior to analysis. A standard of 2.0 g/L ethanol was analyzed approximately every 30 samples to ensure the integrity of the membrane was maintained.

A total of 47 samples were analyzed for cell count. Samples will be taken at 72 hours incubation and 48 hours post-addition of more cellulosic material. Appropriately diluted samples were mixed with 0.05% Trypan blue and loaded into a Neubauer haemocytometer. The cells were counted under 40× magnification.

Experiment #2—Analysis of 2× Feedstock Concentration

The test vessels (a total of 8, 250 mL Erlenmeyer flasks) contained 100 mL of medium. The media contained 40 g/L glucose, 40 g/L xylose, 1.7 g/L yeast nitrogen base (Becton Dickinson #291940) 2.27 g/L urea (ScholAR Chemistry #9472706), and 6.56 g/L peptone (Becton Dickinson #211677). Flasks were prepared as in Experiment #1. The test samples (A132-10, A132-100, G132-10, and G132-100 at 10 g per 100 mL) were added at the time of inoculation (rather than prior to) to reduce the possibility of contamination. In addition to the test samples, 1 mL (1% v/v) of seed flask material was added to each flask. The flasks were incubated at 30° C. and 150 rpm above for 72 hours.

Analysis

Samples were from the 8 test flasks at an incubation time of 0, 6, 12, 24, 36, 48, and 72 hours. Ethanol analyses of the 56 samples were performed as per experiment #1 and are reported in Table 59. A cell count was performed on the 72 hour sample as per experiment #1 and is presented in Table 60.

TABLE 59

Ethanol Concentration in Flasks with Double Feedstock

| Sample Time | Ethanol Concentration (g/L) | | | |
|---|---|---|---|---|
| | A132-10 | A132-100 | G132-10 | G132-100 |
| 0 | 1.38 | 0.26 | 0.12 | 0.11 |
| 6 | 1.75 | 0.21 | 0.20 | 0.10 |
| 12 | 2.16 | 0.73 | 0.69 | 0.31 |
| 24 | 19.05 | 15.35 | 16.55 | 12.60 |
| 36 | 21.75 | 17.55 | 18.00 | 15.30 |
| 48 | 26.35 | 23.95 | 24.65 | 20.65 |
| 72 | 26.95 | 27.35 | 28.90 | 27.40 |

TABLE 60

Cell Concentration at 72 hour Incubation Time in Flasks with Double Feedstock

| Sample | Cell Concentration (×10$^8$/mL) |
|---|---|
| A132-10 | 4.06 |
| A132-100 | 5.37 |
| G132-10 | 5.18 |
| G132-100 | 4.47 |

Experiment #3—Varying Xylose and Glucose Concentrations

Four cellulosic samples (A132-10, A132-100, G132-10, and G132-100) were tested at varying xylose and glucose concentrations as listed in the table below (Table 60).

TABLE 61

Media Composition of Experiment #3 Flasks

| Treatment | Xylose Concentration (g/L) | Glucose Concentration (g/L) |
|---|---|---|
| 50% Sugar | 20.0 | 20.0 |
| 25% Sugar | 10.0 | 10.0 |
| 10% Sugar | 4.0 | 4.0 |
| 0% Sugar | 0.0 | 0 |

The test vessels (a total of 32, 250 mL Erlenmeyer flasks) contained 100 mL of medium. Four different types of media were prepared with the amount of xylose and glucose outlined in Table 61. In addition, the media contained 1.7 g/L yeast nitrogen base (Becton Dickinson #291940) 2.27 g/L urea (ScholAR Chemistry #9472706), and 6.56 g/L peptone (Becton Dickinson #211677). The flasks were prepared as per Experiment #1. The test samples (A132-10, A132-100, G132-10, and G132-100) were added at the time of inoculation (rather than prior to) to reduce the possibility of contamination. In addition to the test samples, 1 mL (1% v/v) of seed flask material was added to each flask. The flasks were incubated at 30° C. and 150 rpm for 72 hours.

Analysis

Samples were taken from the 32 test flasks at an incubation time of 0, 6, 12, 24, 36, 48, and 72 hours (see Tables 62-65). A total of 224 samples were analyzed for ethanol concentration using the YSI Biochem Analyzer based on the alcohol dehydrogenase assay (YSI, Interscience). Samples were centrifuged at 14,000 rpm for 20 minutes and the supernatant stored at −20° C. Of note, some of the samples required centrifugation and then filtration through a 0.45 µm syringe filter. The samples were diluted to between 0-3.2 g/L ethanol prior to analysis. A standard of 2.0 g/L ethanol was analyzed approximately every 30 samples to ensure the integrity of the YSI membrane was maintained.

TABLE 62

Ethanol Results Sample A132-10

| Sample Time | Ethanol Concentration (g/L) | | | | | | | | |
|---|---|---|---|---|---|---|---|---|---|
| | 0% Xylose | 10% Xylose | 25% Xylose | 50% Xylose | 100% Xylose | 0% Sugars* | 10% Sugars* | 25% Sugars* | 50% Sugars* |
| 0 | 0.43 | 0.42 | 0.42 | 0.41 | 0.39 | 0.53 | 0.57 | 0.56 | 0.56 |
| 6 | 1.16 | 1.16 | 1.15 | 1.16 | 1.12 | 0.93 | 0.91 | 0.83 | 0.88 |
| 12 | 1.72 | 1.86 | 1.71 | 1.79 | 1.90 | 1.21 | 2.13 | 2.47 | 2.32 |
| 24 | 15.55 | 15.90 | 17.05 | 17.05 | 16.95 | 1.02 | 4.88 | 9.77 | 13.35 |
| 36 | 17.10 | 17.40 | 20.25 | 21.35 | 20.25 | 1.29 | 4.27 | 9.99 | 17.55 |
| 48 | 16.40 | 17.05 | 19.70 | 23.00 | 26.80 | 1.47 | 3.03 | 8.33 | 16.60 |
| 72 | 15.15 | 15.55 | 19.25 | 21.85 | 28.00 | 1.14 | 1.52 | 5.08 | 14.20 |
| 24 hours post-addition | — | — | — | — | 23.15 | — | — | — | — |
| 48 hours post-addition | — | — | — | — | 21.55 | — | — | — | — |

*Analysis from experiment #3.

TABLE 63

Ethanol Results Sample A132-100

| Sample Time | Ethanol Concentration (g/L) | | | | | | | | |
|---|---|---|---|---|---|---|---|---|---|
| | 0% Xylose | 10% Xylose | 25% Xylose | 50% Xylose | 100% Xylose | 0% Sugars* | 10% Sugars* | 25% Sugars* | 50% Sugars* |
| 0 | 0.11 | 0.09 | 0.17 | 0.20 | 0.18 | 0.12 | 0.14 | 0.09 | 0.13 |
| 6 | 0.13 | 0.15 | 0.15 | 0.15 | 0.14 | 0.10 | 0.11 | 0.11 | 0.13 |
| 12 | 0.88 | 1.00 | 1.18 | 1.25 | 0.89 | 0.18 | 1.58 | 1.55 | 1.57 |
| 24 | 15.90 | 15.70 | 16.50 | 16.05 | 14.60** | 0.18 | 3.33 | 7.99 | 11.15 |
| 36 | 16.00 | 17.90 | 16.90 | 19.45 | 17.80** | 0.21 | 2.85 | 8.37 | 16.10 |
| 48 | 15.75 | 16.70 | 19.30 | 22.15 | 27.00** | 0.54 | 1.47 | 7.54 | 15.60 |
| 72 | 14.85 | 15.35 | 18.55 | 21.30 | 28.50** | 0.78 | 0.51 | 4.47 | 12.90 |
| 24 hours post-addition | — | — | — | — | 24.80** | — | — | — | — |
| 48 hours post-addition | — | — | — | — | 23.60** | — | — | — | — |

*Analysis from experiment #3.
**All results based on analysis of one flask.

TABLE 64

Ethanol Results Sample G132-10

Ethanol Concentration (g/L)

| Sample Time | 0% Xylose | 10% Xylose | 25% Xylose | 50% Xylose | 100% Xylose | 0% Sugars* | 10% Sugars* | 25% Sugars* | 50% Sugars* |
|---|---|---|---|---|---|---|---|---|---|
| 0 | 0.09 | 0.08 | 0.08 | 0.08 | 0.08 | 0.05 | 0.05 | 0.05 | 0.06 |
| 6 | 0.14 | 0.13 | 0.14 | 0.14 | 0.13 | 0.11 | 0.12 | 0.11 | 0.12 |
| 12 | 1.01 | 0.96 | 1.00 | 0.87 | 1.14 | 0.48 | 1.60 | 1.79 | 1.71 |
| 24 | 15.90 | 15.70 | 16.30 | 16.05 | 14.60 | 0.13 | 3.96 | 8.54 | 11.10 |
| 36 | 15.10 | 17.45 | 16.80 | 18.75 | 22.15 | 0.09 | 3.02 | 8.69 | 16.55 |
| 48 | 15.95 | 16.90 | 19.25 | 21.10 | 24.00 | 0.07 | 2.05 | 8.10 | 16.50 |
| 72 | 13.50 | 15.80 | 18.55 | 21.25 | 26.55 | 0.09 | 0.11 | 5.55 | 14.15 |
| 24 hours post-addition | — | — | — | — | 24.95 | — | — | — | — |
| 48 hours post-addition | — | — | — | — | 24.20 | — | — | — | — |

*Analysis from experiment #3.

TABLE 65

Ethanol Results Sample G132-100

Ethanol Concentration (g/L)

| Sample Time | 0% Xylose | 10% w/v Xylose | 25% w/v Xylose | 50% w/v Xylose | 100% w/v Xylose | 0% Sugars* | 10% Sugars* | 25% Sugars* | 50% Sugars* |
|---|---|---|---|---|---|---|---|---|---|
| 0 | 0.04 | 0.04 | 0.04 | 0.04 | 0.05 | 0.05 | 0.05 | 0.05 | 0.06 |
| 6 | 0.07 | 0.07 | 0.08 | 0.08 | 0.07 | 0.04 | 0.05 | 0.05 | 0.06 |
| 12 | 0.60 | 0.56 | 0.67 | 0.58 | 0.71 | 0.13 | 1.37 | 1.48 | 1.44 |
| 24 | 13.05 | 14.45 | 14.90 | 13.95 | 12.05 | 0.03 | 3.67 | 7.62 | 10.55 |
| 36 | 15.10 | 17.10 | 18.25 | 18.20 | 19.25 | 0.01 | 3.09 | 8.73 | 16.10 |
| 48 | 14.40 | 17.00 | 19.35 | 22.55 | 24.45 | 0.01 | 1.91 | 7.76 | 15.85 |
| 72 | 14.70 | 15.40 | 18.45 | 22.10 | 27.55 | 0.03 | 0.01 | 5.08 | 14.30 |
| 24 hours post-addition | — | — | — | — | 25.20 | — | — | — | — |
| 48 hours post-addition | — | — | — | — | 24.60 | — | — | — | — |

*Analysis from experiment #3.

Samples were taken at 72 hours incubation for cell counts (see Tables 66-67). Appropriately diluted samples were mixed with 0.05% Trypan blue and loaded into a Neubauer haemocytometer. The cells were counted under 40× magnification.

Results

One seed flask was used to inoculate all Experiment #1 and #2 test flasks. The optical density (600 nm) of the seed flask was measured to be 5.14 and the cell concentration was 4.65× $10^8$ cells/mL (Tables 65-66). Therefore, the initial concentration of cells in the test flasks was approximately 4.65× $10^6$ cells/mL.

A second seed flask was used to inoculate Experiment #3 flasks. The optical density (600 nm) of the seed flask was 5.78 and the cell concentration was 3.75× $10^8$ cells/mL. Therefore, the initial concentration of cells in the test flasks was approximately 3.75× $10^6$ cells/mL.

TABLE 66

Cell Counts at Incubation Time of 72 hours

Cell Concentration (× $10^8$/mL)

| Sample | 0% Xylose | 10% Xylose | 25% Xylose | 50% Xylose | 100% Xylose | 0% Sugar | 10% Sugar | 25% Sugar | 50% Sugar |
|---|---|---|---|---|---|---|---|---|---|
| A132-10 | 0.37 | 0.63 | 3.72 | 4.92 | 4.05 | 0.26 | 0.22 | 0.26 | 1.54 |
| A132-100 | 0.99 | 1.07 | 0.99 | 0.78 | 1.97 | 0.03* | 0.33 | 0.44 | 1.81 |

TABLE 66-continued

Cell Counts at Incubation Time of 72 hours

Cell Concentration (×10$^8$/mL)

| Sample | 0% Xylose | 10% Xylose | 25% Xylose | 50% Xylose | 100% Xylose | 0% Sugar | 10% Sugar | 25% Sugar | 50% Sugar |
|---|---|---|---|---|---|---|---|---|---|
| G132-10 | 0.95 | 4.50 | 2.67 | 2.67 | 3.82 | 0.01* | 0.17 | 0.49 | 1.92 |
| G132-100 | 6.53 | 4.02 | 4.84 | 4.47 | 5.29 | 0.01* | 0.33 | 0.89 | 2.22 |

*Samples were heavily contaminated after 72 hours of growth. This is expected because the *Pichia* did not grow well without sugar added, and contaminants (from the non-sterile samples) were able to out-grow the *Pichia*.

TABLE 67

Cell Counts at Incubation Time of 48 hours
Post-Addition (100% Xylose and Glucose)

| Sample | Cell Concentration (×10$^8$/mL) |
|---|---|
| A132-10 | 10.17 |
| A132-100 | 3.38 |
| G132-10 | 3.94 |
| G132-100 | 6.53 |

Example 20

Toxicity Testing of Lignocellulosic Samples Against
*P. stipitis* and *S. cerevisiae*

Summary

Thirty-seven samples were analyzed for toxicity against two ethanol-producing cultures, *Saccharomyces cerevesiae* and *Pichia stipitis*. In this study, glucose was added to the samples in order to distinguish between starvation of the cultures and toxicity of the samples.

TABLE 68

Conditions for Toxicity Testing

| Variable | Organism | |
|---|---|---|
| | *Saccharomyces cerevisiae* ATCC 24858 | *Pichia stipitis* NRRL Y-7124 |
| Inoculation Volume (mL) | 0.5-1 (target 6-7 × 10$^5$ cells/mL) | 1 (target 3-4 × 10$^6$ cells/mL) |
| Test Repetition | Single Flasks | |
| Incubation Temperature (±1° C.) | 25° C. | 25° C. |
| Shaker Speed (rpm) | 200 | 125 |
| Type of Container | 500 mL Erlenmeyer Flask | 250 mL Erlenmeyer Flask |
| Media volume | 100 mL | 100 mL |
| Total Incubation time (hours) | 72 | 72 |
| Ethanol Analysis (hours) | 0, 6, 12, 24, 36, 48, 72 | 0, 6, 12, 24, 36, 48, 72 |
| Cell Counts (hours) | 24, 72 | 24, 72 |
| pH | 0 hours | 0 hours |

Protocol

A summary of the protocol used is listed in Table 68. A description of the chemicals used in toxicity testing is listed in Table 69. Two control flasks (no sample added) were performed for each microorganism for each week of testing. A total of 82 flasks were analyzed.

During the experiments, no ethanol or cells appeared in the *P. stipitis* flasks containing samples C, C-1e, C-5e, and C-10e in the first 24 hours of incubation. In order to confirm the results, the test was repeated. The second test confirmed some inhibition of *P. stipitis* growth when samples C, C1E, C5E, and C10E were added to the flasks.

TABLE 69

Chemicals and Materials Used for Toxicity Testing

| Media Component | Manufacturer | Reference # | Lot # |
|---|---|---|---|
| Urea | ScholAR Chemistry | 9472706 | AD-7284-43 |
| Yeast Nitrogen Base | Becton Dickinson | 291940 | 7128171 |
| Peptone | Becton Dickinson | 211677 | 4303198 |
| Xylose | Alfa Aesar | A10643 | 10130919 |
| Glucose | Sigma | G-5400 | 107H0245 |
| Yeast Extract | Becton Dickinson | 288620 | 4026828 |
| YM Broth | Becton Dickinson | 271120 | 6278265 |

TABLE 70

YSI Components Used in Toxicity Study

| Component | Catalogue # |
|---|---|
| YSI Ethanol Membrane | 2786 |
| YSI Ethanol Standard (3.2 g/L) | 2790 |
| YSI Ethanol Buffer | 2787 |

Test Samples

Seven test samples (all with the C designation) were ground using a coffee grinder suitable for small samples. The samples were ground to a consistent particle size (between samples) with the naked eye. Sample number C-100e ground easily to a small particle size.

All samples were added to the flasks at a concentration of 50 grams per liter with the exception of the six P samples (25 grams per liter). These samples were white to off-white in color and visually fluffy and the flasks would not mix properly (not enough free liquid) at the 50 grams per liter concentration. Samples S dissolved easily and could in the future be added to the flasks at a higher concentration. Samples A and G could be added at 100 grams per liter in the future.

Testing was performed using the two microorganisms as described below.

*Saccharomyces cerevisiae* ATCC 24858 (American Type Culture Collection)

A working cell bank of *S. cerevisiae* ATCC 24858 was prepared from a rehydrated lyophilized culture obtained from American Type Culture Collection. Cryovials containing *S. cerevisiae* culture in 15% v/v glycerol are stored at −75° C. A portion of the thawed working cell bank material will be streaked onto a Yeast Mold (YM) Broth+20 g/L agar (pH 5.0) and incubated at 30° C. for 2 days. A 250 mL Erlenmeyer flask containing 50 mL of medium (20 g/L glucose, 3 g/L yeast extract, and 5.0 g/L peptone, pH 5.0) was inoculated with one colony from the YM plate and incubated for 24 hours at 25° C. and 200 rpm. After 23 hours of growth, a sample was taken and analyzed for optical density (600 nm in a UV spectrophotometer) and purity (Gram stain). Based on these results, one flask (called the Seed Flask) with an OD of 9-15 and pure Gram stain was to be used for inoculating the growth flasks. After 23 hours of growth, the seed flask had a low OD (5.14) and cell count ($1.35 \times 10^8$ cells/mL). Of note, the colony taken from the seed plate was smaller than usual. Therefore, 0.5 mL of seed material (as opposed to the planned 0.1 mL) was added to each test vessel.

The test vessels were 500 mL Erlenmeyer flasks containing 100 mL of the sterile medium described above. All flasks were autoclaved at 121° C. and 15 psi prior to the addition of the test materials. The test materials were not sterilized, as autoclaving would change the content of the samples. The test samples were added at the time of inoculation (rather than prior to) to reduce the possibility of contamination. In addition to the test samples, 0.5-1.0 mL (0.5-1.0% v/v) of seed flask material was added to each flask. The flasks were incubated as described above for 72 hours.

*Pichia stipitis* (ARS Culture Collection)

A working cell bank of *P. stipitis* NRRL Y-7124 was prepared from a rehydrated lyophilized culture obtained from ARS Culture Collection. Cryovials containing *P. stipitis* culture in 15% v/v glycerol are stored at −75° C. A portion of the thawed working cell bank material was streaked onto a Yeast Mold (YM) Broth+20 g/L agar (pH 5.0) and incubated at 30° C. for 2 days. The plates were held for up to 5 days at 4° C. before use. A 250 mL Erlenmeyer flask containing 100 mL of medium (40 g/L glucose, 1.7 g/L yeast nitrogen base, 2.27 g/L urea, 6.56 g/L peptone, 40 g/L xylose, pH 5.0) was inoculated with one colony and incubated for 24 hours at 25° C. and 125 rpm. After 23 hours of growth, a sample was taken and analyzed for optical density (600 nm in a UV spectrophotometer) and purity (Gram stain). Based on these results, one flask (called the Seed Flask) at an optical density of 5-9 and with a pure Gram Stain was used to inoculate all of the test flasks.

The test vessels were 250 mL Erlenmeyer flasks containing 100 mL of the sterile medium described above. All flasks were autoclaved empty at 121° C. and 15 psi and filter sterilized (0.22 μm filter) medium added to the flasks prior to the addition of the test materials. The test materials were not sterilized, as autoclaving would change the content of the samples and filter sterilization not appropriate for sterilization of solids. The test samples were added at the time of inoculation (rather than prior to) to reduce the possibility of contamination. In addition to the test samples, 1 mL (1% v/v) of seed flask material was added to each flask. The flasks were incubated as described above for 72 hours.

Analysis

Samples were taken from seed flasks just prior to inoculation and each test flask at 24 and 72 hours and analyzed for cell concentration using direct counts. Appropriately diluted samples of *S. cerevisiae* and *P. stipitis* were mixed with 0.05% Trypan blue, loaded into a Neubauer haemocytometer. The cells were counted under 40× magnification.

Samples were taken from each flask at 0, 6, 12, 24, 36, 48 and 72 hours and analyzed for ethanol concentration using the YSI Biochem Analyzer based on the alcohol dehydrogenase assay (YSI, Interscience). Samples were centrifuged at 14,000 rpm for 20 minutes and the supernatant stored at −20° C. The samples will be diluted to 0-3.2 g/L ethanol prior to analysis. A standard of 2.0 g/L ethanol was analyzed approximately every 30 samples to ensure the integrity of the membrane was maintained during analysis.

Calculations

The following calculations were used to compare the cell counts and ethanol concentration to the control flasks.

% performance=(concentration of ethanol in test flask/ethanol in control)*100% cells=(number of cells in test flask/number of cells in control flask)*100

Results

The *S. cerevisiae* seed flask had an optical density (600 nm) of 5.14 and a cell concentration of $1.35 \times 10^8$ cells/mL. One half mL of seed flask material was added to each of the test flasks. Therefore, the starting cell concentration in each flask was $6.75 \times 10^5$/mL. During the second week of testing, the *S. cerevisiae* seed flask had an optical density (600 nm) of 4.87 and a cell concentration of $3.15 \times 10^7$ cells/mL. One mL of seed flask material was added to each of the test flasks. Therefore, the starting cell concentration in each flask was $6.30 \times 10^5$/mL. The pH of the *S. cerevisiae* flasks at a sample time of 0 hours is presented in Table 71. The pH of the flask contents was within the optimal pH for *S. cerevisiae* growth (pH 4-6). No pH adjustment was required.

TABLE 71 pH of *S. cerevisiae* flasks at sample time 0 hours

| Sample Number | pH |
| --- | --- |
| P | 5.04 |
| P1E | 4.99 |
| P5E | 5.04 |
| P10E | 4.98 |
| P50E | 4.67 |
| P100E | 4.43 |
| G | 5.45 |
| G1E | 5.47 |
| G5E | 5.46 |
| G10E | 5.39 |
| G50E | 5.07 |
| A | 5.72 |
| A1E | 5.69 |
| A5E | 5.62 |
| A10E | 5.61 |
| A50E | 5.74 |
| S* | 5.10 |
| S1E | 5.08 |
| S5E | 5.07 |
| S10E | 5.04 |
| S30E | 4.84 |
| S50E | 4.57 |
| S100E | 4.33 |
| C | 5.46 |
| C1E | 5.54 |
| C5E | 5.50 |
| C10E | 5.33 |
| C30E | 5.12 |
| C50E | 4.90 |
| C100E | 4.66 |
| ST | 5.11 |
| ST1E | 5.06 |
| ST5E | 4.96 |
| ST10E | 4.94 |
| ST30E | 5.68 |
| ST50E | 4.48 |
| ST100E | 4.23 |
| control A | 5.02 |
| control B | 5.04 |

*"S" refers to sucrose
*"C" refers to corn
*"ST" refers to starch

The ethanol concentration and performance in the *S. cerevisiae* flasks are presented in Table 72 and 73. The highest ethanol concentrations were produced by the S series.

TABLE 72

Ethanol Concentration in *S. cerevisiae* flasks

| Sample Number | Ethanol Concentration (g/L) at the following times (hours) | | | | | | |
|---|---|---|---|---|---|---|---|
| | 0 | 6 | 12 | 24 | 36 | 48 | 72 |
| P | 0.02 | 0.04 | 0.38 | 5.87 | 7.86 | 5.41 | 1.04 |
| P1E | 0.03 | 0.03 | 0.28 | 5.10 | 8.03 | 5.46 | 0.58 |
| P5E | 0.03 | 0.04 | 0.57 | 8.84 | 6.38 | 3.40 | 0.04 |
| P10E | 0.06 | 0.05 | 0.65 | 6.63 | 7.66 | 5.57 | 1.40 |
| P50E | 0.04 | 0.03 | 0.26 | 2.80 | 5.85 | 8.59 | 5.68 |
| P100E | 0.04 | 0.02 | 0.12 | 3.64 | 8.26 | 7.51 | 3.03 |
| G | 0.04 | 0.04 | 0.57 | 10.20 | 8.24 | 6.66 | 2.84 |
| G1E | 0.04 | 0.05 | 0.46 | 10.20 | 9.24 | 6.94 | 2.84 |
| G5E | 0.11 | 0.11 | 0.44 | 10.00 | 8.7 | 6.36 | 0.88 |
| G10E | 0.05 | 0.04 | 0.40 | 9.97 | 8.41 | 5.79 | 0.11 |
| G50E | 0.05 | 0.05 | 0.48 | 9.72 | 8.33 | 6.13 | 2.38 |
| A | 0.29 | 0.38 | 0.48 | 8.43 | 8.76 | 7.09 | 4.66 |
| A1E | 0.34 | 0.44 | 0.79 | 9.66 | 8.9 | 7.18 | 2.64 |
| A5E | 0.55 | 0.45 | 0.99 | 9.44 | 8.96 | 7.56 | 3.80 |
| A10E | 0.55 | 0.55 | 0.93 | 9.58 | 8.33 | 6.28 | 1.40 |
| A50E | 0.22 | 0.08 | 0.38 | 9.38 | 8.01 | 5.99 | 0.98 |
| S | 0.03 | 0.03 | 0.39 | 5.73 | 7.06 | 10.10 | 15.90 |
| S1E | 0.05 | 0.06 | 0.31 | 7.24 | 9.52 | 12.10 | 14.90 |
| S5E | 0.02 | 0.05 | 0.34 | 5.87 | 7.68 | 11.90 | 19.00 |
| S10E | 0.03 | 0.04 | 0.35 | 5.88 | 7.72 | 11.50 | 19.30 |
| S30E | 0.03 | 0.05 | 0.09 | 5.94 | 7.97 | 11.20 | 20.40 |
| S50E* | 0.13 | 0.19 | 0.47 | 5.46 | 7.96 | 13.00 | 18.30 |
| S100E | 0.11 | 0.10 | 0.21 | 7.00 | 10.6 | 13.80 | 12.70 |
| C | 0.01 | 0.04 | 0.32 | 8.47 | 7.57 | 5.48 | 6.40 |
| C1E | 0.00 | 0.06 | 0.37 | 8.93 | 7.86 | 5.99 | 1.37 |
| C5E | 0.03 | 0.05 | 0.48 | 9.32 | 7.92 | 5.69 | 1.41 |
| C10E | 0.02 | 0.04 | 0.52 | 9.14 | 7.67 | 5.34 | 0.35 |
| C30E | 0.02 | 0.05 | 0.28 | 9.15 | 8.15 | 5.84 | 2.47 |
| C50E | 0.03 | 0.06 | 0.44 | 9.31 | 7.79 | 5.78 | 1.79 |
| C100E | 0.03 | 0.06 | 0.58 | 9.06 | 6.85 | 5.95 | 1.09 |
| ST | 0.02 | 0.05 | 0.99 | 8.54 | 6.69 | 5.09 | 0.42 |
| ST1E | 0.03 | 0.04 | 0.70 | 8.87 | 7.29 | 4.81 | 1.04 |
| ST5E | 0.02 | 0.04 | 0.52 | 8.61 | 7.16 | 4.97 | 0.85 |
| ST10E | 0.02 | 0.05 | 0.33 | 8.97 | 7.05 | 5.26 | 0.68 |
| ST30E | 0.03 | 0.04 | 0.71 | 8.47 | 6.96 | 4.89 | 0.21 |
| ST50E | 0.04 | 0.07 | 0.34 | 8.46 | 8.19 | 7.04 | 3.20 |
| ST100E | 0.03 | 0.10 | 0.30 | 9.30 | 8.62 | 7.29 | 4.23 |
| control A | 0.01 | 0.07 | 0.85 | 5.92 | 8.18 | 7.81 | 6.26 |
| control B | 0.01 | 0.04 | 0.27 | 4.86 | 6.43 | 8.01 | 6.75 |
| control A* | 0.04 | 0.21 | 1.36 | 5.19 | 7.31 | 7.55 | 5.16 |
| control B* | 0.03 | 0.20 | 1.18 | 5.16 | 5.96 | 7.62 | 5.32 |

*analyzed week 2

See Table 72 for Sample Number key

TABLE 73

Performance in *S. cerevisiae* flasks

| Sample Number | Performance (%) at the following times (hours) | | | |
|---|---|---|---|---|
| | 24 | 36 | 48 | 72 |
| P | 108.9 | 107.6 | 68.4 | 16.0 |
| P1E | 94.6 | 109.9 | 69.0 | 8.9 |
| P5E | 164.0 | 87.3 | 43.0 | 0.6 |
| P10E | 123.0 | 104.9 | 70.4 | 21.5 |
| P50E | 51.9 | 80.1 | 108.6 | 87.3 |
| P100E | 67.5 | 113.1 | 94.9 | 46.5 |
| G | 189.2 | 112.8 | 84.2 | 43.6 |
| G1E | 189.2 | 126.5 | 87.7 | 43.6 |
| G5E | 185.5 | 119.1 | 80.4 | 13.5 |
| G10E | 185.0 | 115.1 | 73.2 | 1.7 |
| G50E | 180.3 | 114.0 | 77.5 | 36.6 |
| A | 156.4 | 119.9 | 89.6 | 71.6 |
| A1E | 179.2 | 121.8 | 90.8 | 40.6 |
| A5E | 175.1 | 122.7 | 95.6 | 58.4 |
| A10E | 177.7 | 114.0 | 79.4 | 21.5 |
| A50E | 174.0 | 109.7 | 75.7 | 15.1 |
| S | 106.3 | 96.6 | 127.7 | 244.2 |
| S1E | 134.3 | 130.3 | 153.0 | 228.9 |
| S5E | 108.9 | 105.1 | 150.4 | 291.9 |
| S10E | 109.1 | 105.7 | 145.4 | 296.5 |
| S30E | 110.2 | 109.1 | 141.6 | 313.4 |
| S50E* | 105.5 | 119.9 | 171.3 | 349.2 |
| S100E | 129.9 | 145.1 | 174.5 | 195.1 |
| C | 157.1 | 103.6 | 69.3 | 98.3 |
| C1E | 165.7 | 107.6 | 75.7 | 21.0 |
| C5E | 172.9 | 108.4 | 71.9 | 21.7 |
| C10E | 169.6 | 105.0 | 67.5 | 5.4 |
| C30E | 169.8 | 111.6 | 73.8 | 37.9 |
| C50E | 172.7 | 106.6 | 73.1 | 27.5 |
| C100E | 168.1 | 93.8 | 75.2 | 16.7 |
| ST | 158.4 | 91.6 | 64.3 | 6.5 |
| ST1E | 164.6 | 99.8 | 60.8 | 16.0 |
| ST5E | 159.7 | 98.0 | 62.8 | 13.1 |
| ST10E | 166.4 | 96.5 | 66.5 | 10.4 |
| ST30E | 157.1 | 95.3 | 61.8 | 3.2 |
| ST50E | 157.0 | 112.1 | 89.0 | 49.2 |
| ST100E | 172.5 | 118.0 | 92.2 | 65.0 |
| control A | 109.8 | 112.0 | 98.7 | 96.2 |
| control B | 90.2 | 88.0 | 101.3 | 103.7 |
| control A* | 100.3 | 110.1 | 99.5 | 98.5 |
| control B* | 99.7 | 89.8 | 100.4 | 101.5 |

*analyzed week 2

The cell concentration and % cells in the *S. cerevisiae* flasks are presented in Table 74. High cell counts were observed in all flasks; however, not all of the cells appear to be making ethanol.

TABLE 74

*S. cerevisiae* Cell Counts and % Cells

| Sample Number | Cell Count (cells × $10^8$/mL) | | % Cells (count/count control) *100 | |
|---|---|---|---|---|
| | 24 hours | 72 hours | 24 hours | 72 hours |
| P | 0.62 | 0.96 | 97.7 | 139.0 |
| P1E | 0.35 | 1.18 | 54.1 | 170.9 |
| P5E | 1.13 | 1.93 | 177.3 | 279.5 |
| P10E | 0.59 | 1.42 | 91.8 | 205.6 |
| P50E | 0.32 | 1.40 | 49.4 | 202.8 |
| P100E | 0.45 | 1.94 | 70.6 | 281.0 |
| G | 0.74 | 3.48 | 116.5 | 504.0 |
| G1E | 0.68 | 3.65 | 107.1 | 528.6 |
| G5E | 0.62 | 3.87 | 96.5 | 560.5 |
| G10E | 0.70 | 2.73 | 109.5 | 395.4 |
| G50E | 0.46 | 2.10 | 71.8 | 304.1 |
| A | 0.55 | 3.53 | 86.0 | 511.2 |
| A1E | 0.83 | 3.45 | 130.7 | 499.6 |
| A5E | 0.67 | 3.53 | 104.8 | 511.2 |
| A10E | 0.53 | 1.95 | 83.6 | 282.4 |
| A50E | 0.66 | 1.62 | 103.5 | 234.6 |
| S | 0.44 | 1.11 | 69.5 | 160.8 |
| S1E | 0.44 | 1.10 | 68.2 | 159.3 |
| S5E | 0.23 | 0.99 | 36.5 | 143.4 |
| S10E | 0.39 | 0.73 | 61.2 | 105.4 |
| S30E | 0.31 | 0.71 | 48.3 | 102.1 |
| S50E* | 0.44 | 0.90 | 86.5 | 196.5 |
| S100E | 0.53 | 0.84 | 82.4 | 121.7 |
| C | 0.45 | 1.81 | 70.6 | 262.1 |
| C1E | 0.71 | 2.40 | 110.6 | 347.6 |
| C5E | 0.53 | 2.33 | 83.6 | 337.4 |
| C10E | 0.77 | 1.55 | 120.0 | 224.5 |
| C30E | 0.75 | 1.80 | 117.6 | 260.7 |
| C50E | 0.64 | 1.70 | 100.1 | 246.2 |
| C100E | 0.81 | 1.51 | 127.1 | 218.7 |
| ST | 0.75 | 1.75 | 117.6 | 253.4 |
| ST1E | 0.57 | 1.36 | 89.4 | 197.0 |
| ST5E | 0.58 | 1.49 | 90.7 | 215.8 |

TABLE 74-continued

S cerevisiae Cell Counts and % Cells

| Sample Number | Cell Count (cells × 10⁸/mL) 24 hours | Cell Count (cells × 10⁸/mL) 72 hours | % Cells (count/count control) *100 24 hours | % Cells (count/count control) *100 72 hours |
|---|---|---|---|---|
| ST10E | 0.61 | 1.32 | 95.4 | 191.2 |
| ST30E | 0.59 | 0.60 | 91.8 | 86.9 |
| ST50E | 0.59 | 1.30 | 91.8 | 188.3 |
| ST100E | 0.41 | 1.24 | 63.5 | 179.6 |
| control A | 0.81 | 0.79 | 127.1 | 114.1 |
| control B | 0.47 | 0.59 | 72.9 | 85.9 |
| control A* | 0.66 | 0.42 | 131.2 | 91.7 |
| control B* | 0.35 | 0.50 | 69.0 | 108.1 |

The *P. stipitis* seed flask had an optical density (600 nm) of 5.01 and a cell concentration of 3.30×10⁸ cells/mL. One mL of seed flask material was added to each of the test flasks. Therefore, the starting cell concentration in each flask was 3.30×10⁶/mL. During the second week of testing, the *P. stipitis* seed flask had an optical density (600 nm) of 5.45 and a cell concentration of 3.83×10⁸ cells/mL. One mL of seed flask material was added to each of the test flasks. Therefore, the starting cell concentration in each flask was 3.83×10⁶/mL. The pH of the *P. stipitis* flasks at a sample time of 0 hours is presented in Table 75. The pH of the flask contents was within the optimal pH for *P. stipitis* growth (pH 4-7). No pH adjustment was required.

TABLE 75 pH of *P. stipitis* Flasks at Sample Time 0 Hours

| Sample Number | pH |
|---|---|
| P | 4.91 |
| P1E | 4.87 |
| P5E | 4.90 |
| P10E | 4.78 |
| P50E | 4.46 |
| P100E | 4.24 |
| G | 5.45 |
| G1E | 5.43 |
| G5E | 5.48 |
| G10E | 5.32 |
| G50E | 4.99 |
| A | 5.69 |
| A1E | 5.66 |
| A5E | 5.60 |
| A10E | 5.58 |
| A50E | 5.69 |
| S | 5.00 |
| S1E | 4.94 |
| S5E | 4.86 |
| S10E | 4.78 |
| S30E | 4.51 |
| S50E | 4.27 |
| S100E | 4.08 |
| C | 5.36 |
| C1E | 5.30 |
| C5E | 5.29 |
| C10E | 5.06 |
| C30E | 4.89 |
| C50E | 4.70 |
| C100E | 4.59 |
| ST | 4.93 |
| ST1E | 4.90 |
| ST5E | 4.81 |
| ST10E | 4.83 |
| ST30E | 4.91 |
| ST50E | 4.24 |
| ST100E | 4.07 |
| control A | 4.93 |
| control B | 4.91 |

The ethanol concentration and performance in the *P. stipitis* flasks are presented in Table 76 and 77. The highest ethanol concentrations were the G and A series. Flasks C-30e, C-50e, and C-100e also contained high concentrations of ethanol. The cell concentration and % cells in the *P. stipitis* flasks are presented in Table 78. Low cell concentrations were observed in the flasks with the S designations. Low cell counts were also observed in flasks containing samples C, C1E, C5E, and C10E at the 24 hour sample time.

TABLE 76

Ethanol concentration in *P. stipitis* flasks

| Sample Number | Ethanol Concentration (g/L) at the following times (hours) 0 | 6 | 12 | 24 | 36 | 48 | 72 |
|---|---|---|---|---|---|---|---|
| P | 0.01 | 0.05 | 0.26 | 4.98 | 8.57 | 14.10 | 17.00 |
| P1E | 0.02 | 0.03 | 0.04 | 4.24 | 9.03 | 12.40 | 17.30 |
| P5E | 0.02 | 0.03 | 0.42 | 6.72 | 12.40 | 15.60 | 18.60 |
| P10E | 0.02 | 0.02 | 0.01 | 1.38 | 8.69 | 13.00 | 17.00 |
| P50E | 0.01 | 0.02 | 0.02 | 0.03 | 3.77 | 10.50 | 16.90 |
| P100E | 0.02 | 0.03 | 0.02 | 3.75 | 10.50 | 15.60 | 18.80 |
| G | 0.02 | 0.08 | 0.20 | 10.80 | 17.70 | 19.40 | 25.40 |
| G1E | 0.04 | 0.12 | 0.50 | 12.20 | 19.60 | 23.80 | 28.60 |
| G5E | 0.07 | 0.14 | 0.73 | 12.50 | 19.10 | 24.50 | 27.50 |
| G10E | 0.04 | 0.19 | 0.42 | 10.20 | 19.10 | 22.90 | 28.20 |
| G50E | 0.05 | 0.22 | 0.25 | 8.73 | 18.40 | 22.20 | 28.00 |
| A | 0.13 | 0.28 | 0.82 | 16.10 | 19.40 | 19.30 | 18.60 |
| A1E | 0.22 | 0.59 | 1.08 | 16.10 | 22.40 | 27.60 | 27.70 |
| A5E | 0.32 | 0.43 | 0.43 | 10.60 | 22.10 | 27.10 | 28.10 |
| A10E | 0.33 | 0.61 | 1.15 | 14.90 | 22.00 | 27.10 | 27.90 |
| A50E | 0.30 | 0.10 | 0.47 | 13.40 | 20.20 | 24.80 | 27.10 |
| S | 0.01 | 0.01 | 0.26 | 3.68 | 7.50 | 10.20 | 13.30 |
| S1E | 0.02 | 0.02 | 0.22 | 4.98 | 9.22 | 11.60 | 14.20 |
| S5E | 0.02 | 0.02 | 0.19 | 4.25 | 8.50 | 11.70 | 14.70 |
| S10E | 0.03 | 0.02 | 0.17 | 2.98 | 8.87 | 11.90 | 14.70 |
| S30E | 0.08 | 0.05 | 0.03 | 2.96 | 8.73 | 12.60 | 16.50 |
| S50E | 0.08 | 0.05 | 0.04 | 2.24 | 6.13 | 7.95 | 12.50 |
| S100E | 0.11 | 0.10 | 0.08 | 3.36 | 7.82 | 10.50 | 13.90 |
| C* | 0.02 | 0.03 | 0.05 | 0.23 | 1.66 | 2.68 | 6.57 |
| C1E* | 0.03 | 0.03 | 0.03 | 0.07 | 0.95 | 1.85 | 10.20 |
| C5E* | 0.03 | 0.02 | 0.04 | 0.05 | 0.37 | 1.59 | 4.80 |
| C10E* | 0.03 | 0.04 | 0.04 | 0.05 | 3.91 | 15.20 | 28.30 |
| C30E | 0.01 | 0.03 | 0.60 | 12.30 | 21.20 | 26.00 | 27.20 |
| C50E | 0.02 | 0.02 | 0.45 | 12.30 | 19.50 | 23.80 | 29.20 |
| C100E | 0.05 | 0.04 | 0.38 | 11.40 | 18.70 | 22.90 | 27.70 |
| ST | 0.03 | 0.03 | 0.37 | 6.69 | 10.70 | 13.50 | 10.90 |
| ST1E | 0.01 | 0.00 | 0.48 | 5.24 | 9.37 | 12.50 | 15.70 |
| ST5E | 0.02 | 0.03 | 0.29 | 5.45 | 10.10 | 11.90 | 14.70 |
| ST10E | 0.02 | 0.02 | 0.42 | 5.60 | 9.44 | 12.20 | 14.90 |
| ST30E | 0.05 | 0.04 | 0.73 | 5.70 | 9.50 | 12.10 | 15.20 |
| ST50E | 0.02 | 0.05 | 0.19 | 5.16 | 9.47 | 12.70 | 15.20 |
| ST100E* | 0.07 | 0.15 | 0.11 | 4.98 | 10.70 | 15.40 | 18.80 |

TABLE 76-continued

Ethanol concentration in *P. stipitis* flasks

| Sample Number | Ethanol Concentration (g/L) at the following times (hours) | | | | | | |
|---|---|---|---|---|---|---|---|
| | 0 | 6 | 12 | 24 | 36 | 48 | 72 |
| control A | 0.02 | 0.03 | 0.37 | 4.05 | 7.50 | 9.24 | 11.50 |
| control B | 0.02 | 0.02 | 0.30 | 4.22 | 7.44 | 9.44 | 11.50 |
| control A* | 0.02 | 0.05 | 0.69 | 4.86 | 8.69 | 11.10 | 16.40 |
| control B* | 0.02 | 0.05 | 0.74 | 5.96 | 10.80 | 13.00 | 14.00 |

*analyzed week 2

TABLE 77

Performance in *P. stipitis* flasks

| Sample Number | Performance (%) at the following times (hours) | | | |
|---|---|---|---|---|
| | 24 | 36 | 48 | 72 |
| P | 120.3 | 114.7 | 151.0 | 147.8 |
| P1E | 102.4 | 120.9 | 132.8 | 150.4 |
| P5E | 162.3 | 166.0 | 167.0 | 161.7 |
| P10E | 33.3 | 116.3 | 139.2 | 147.8 |
| P50E | 0.7 | 50.5 | 112.4 | 147.0 |
| P100E | 90.6 | 140.6 | 167.0 | 163.5 |
| G | 260.9 | 236.9 | 207.7 | 220.9 |
| G1E | 294.7 | 262.4 | 254.8 | 248.7 |
| G5E | 301.9 | 255.7 | 262.3 | 239.1 |
| G10E | 246.4 | 255.7 | 245.2 | 245.2 |
| G50E | 210.9 | 246.3 | 237.7 | 243.5 |
| A | 388.9 | 259.7 | 206.6 | 161.7 |
| A1E | 388.9 | 299.9 | 295.5 | 240.9 |
| A5E | 256.0 | 295.9 | 290.1 | 244.3 |
| A10E | 359.9 | 294.5 | 290.1 | 242.6 |
| A50E | 323.7 | 270.4 | 265.5 | 235.7 |
| S | 88.9 | 100.4 | 109.2 | 115.7 |
| S1E | 120.3 | 123.4 | 124.2 | 123.5 |
| S5E | 102.7 | 113.8 | 125.3 | 127.8 |
| S10E | 72.0 | 118.7 | 127.4 | 127.8 |
| S30E | 71.5 | 116.9 | 134.9 | 143.5 |
| S50E | 54.1 | 82.1 | 85.1 | 108.7 |
| S100E | 81.2 | 104.7 | 112.4 | 120.9 |
| C* | 4.2 | 17.0 | 22.2 | 43.2 |
| C1E* | 1.4 | 9.7 | 15.4 | 67.1 |
| C5E* | 0.9 | 3.8 | 13.2 | 31.6 |
| C10E* | 0.9 | 40.1 | 126.1 | 246.1 |
| C30E | 297.1 | 283.8 | 278.4 | 236.5 |
| C50E | 297.1 | 261.0 | 254.8 | 253.9 |
| C100E | 275.4 | 250.3 | 245.2 | 240.9 |
| ST | 161.6 | 143.2 | 144.5 | 94.8 |
| ST1E | 126.6 | 125.4 | 133.8 | 136.5 |
| ST5E | 131.6 | 135.2 | 127.4 | 127.8 |
| ST10E | 135.3 | 126.4 | 130.6 | 129.6 |
| ST30E | 137.7 | 127.2 | 129.6 | 132.2 |
| ST50E | 124.6 | 126.8 | 136.0 | 132.2 |
| ST100E* | 120.3 | 109.7 | 127.8 | 123.7 |
| control A | 97.8 | 100.4 | 98.9 | 100.0 |
| control B | 101.9 | 99.6 | 101.1 | 100.0 |
| control A* | 89.8 | 89.1 | 92.1 | 107.9 |
| control B* | 110.2 | 110.8 | 107.9 | 92.1 |

*analyzed in week 2

TABLE 78

*P. stipitis* Cell Counts and % Cells

| Sample Number | Cell Count (cells × 10⁸/mL) | | % Cells (count/count control) *100 | |
|---|---|---|---|---|
| | 24 hours | 72 hours | 24 hours | 72 hours |
| P | 2.78 | 11.00 | 80.6 | 148.0 |
| P1E | 2.10 | 7.20 | 60.9 | 96.9 |
| P5E | 2.93 | 9.68 | 84.9 | 130.3 |
| P10E | 1.42 | 7.73 | 41.2 | 104.0 |
| P50E | 0.33 | 8.63 | 9.6 | 116.2 |
| P100E | 1.58 | 8.25 | 45.8 | 111.0 |
| G | 1.50 | 14.20 | 43.5 | 191.1 |
| G1E | 3.90 | 8.10 | 113.0 | 109.0 |
| G5E | 2.93 | 6.45 | 84.9 | 86.8 |
| G10E | 4.35 | 13.30 | 126.1 | 179.0 |
| G50E | 3.75 | 11.60 | 108.7 | 156.1 |
| A | 7.43 | 8.55 | 215.4 | 115.1 |
| A1E | 4.13 | 9.53 | 119.7 | 128.3 |
| A5E | 3.68 | 9.75 | 106.7 | 131.2 |
| A10E | 4.50 | 7.50 | 130.4 | 100.9 |
| A50E | 6.23 | 5.33 | 180.6 | 71.7 |
| S | 3.53 | 5.55 | 102.3 | 74.7 |
| S1E | 3.00 | 3.30 | 87.0 | 44.4 |
| S5E | 3.68 | 3.00 | 106.7 | 40.4 |
| S10E | 1.73 | 5.78 | 50.1 | 77.8 |
| S30E | 2.55 | 5.48 | 73.9 | 73.8 |
| S50E | 2.63 | 6.15 | 76.2 | 82.8 |
| S100E | 2.25 | 4.43 | 65.2 | 59.6 |
| C* | 0.00 | 0.26 | 0.00 | 7.2 |
| C1E* | 0.00 | 0.36 | 0.00 | 9.9 |
| C5E* | 0.00 | 0.08 | 0.00 | 2.1 |
| C10E* | 0.00 | 5.85 | 0.00 | 160.7 |
| C30E | 5.78 | 4.20 | 167.5 | 56.5 |
| C50E | 3.40 | 7.35 | 98.6 | 98.9 |
| C100E | 1.98 | 6.60 | 57.4 | 88.8 |
| ST | 2.55 | 7.65 | 73.9 | 103.0 |
| ST1E | 2.00 | 8.70 | 58.0 | 117.1 |
| ST5E | 1.85 | 6.75 | 53.6 | 90.8 |
| ST10E | 1.83 | 5.40 | 53.0 | 72.7 |
| ST30E | 2.78 | 6.15 | 80.6 | 82.8 |
| ST50E | 1.33 | 3.45 | 38.6 | 46.4 |
| ST100E* | 4.35 | 3.83 | 59.8 | 105.2 |
| control A | 3.60 | 7.13 | 104.3 | 96.0 |
| control B | 3.30 | 7.73 | 95.7 | 104.0 |
| control A* | 7.50 | 3.23 | 103.0 | 88.7 |
| control B* | 7.05 | 4.05 | 96.8 | 111.3 |

*analyzed week 2

Cell Toxicity Results Summary

*Zymomonas mobilis*

Figure 7:
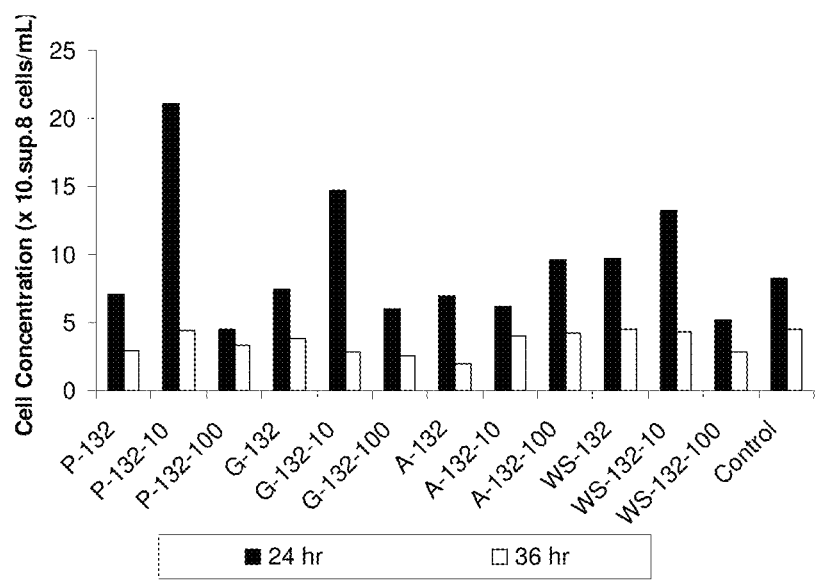
FIG. 7 is a graph showing cell concentrations for Z. mobilis.

As shown in FIG. 7, elevated cell numbers (e.g., greater than the control) were observed in samples containing P-132-10, G-132-10, and WS-132-10 at the 24 hour time point. Cell numbers in the presence of all other samples were comparable to the control. This observation indicates that the substrates were not toxic towards *Z. mobilis* for up to 24 hours after seeding.

At the 36 hour time point, a decrease in cell numbers (e.g., due to a loss of cells or cell death) was observed for all samples, including the control. The greatest decrease in cell numbers was observed for those samples containing P-132-10, G-132-10. The likely cause of this effect is common to all samples, including the control. Thus, the cause of this effect is not the test substrates, as these vary in each sample, and are not present in the control. Possible explanations for this observation include inappropriate culture conditions (e.g., temperature, media compositions), or ethanol concentrations in the sample.

As shown in FIG. 7, all cells produced comparable amounts of ethanol (e.g., 5-10 g/L) at each time point, irrespective of the substrate. Consistent with the cell number data presented in FIG. 8, ethanol concentration in each sample peaked at the 24 hour time point. In contrast to the cell number data, ethanol concentration did not decrease at subsequent time points. This was expected as ethanol was not removed from the system. In addition, this data suggests that ethanol production in these samples may have resulted from fermentation of glucose in the culture media. None of the substrates tested appeared to increase ethanol production.

Figure 8:
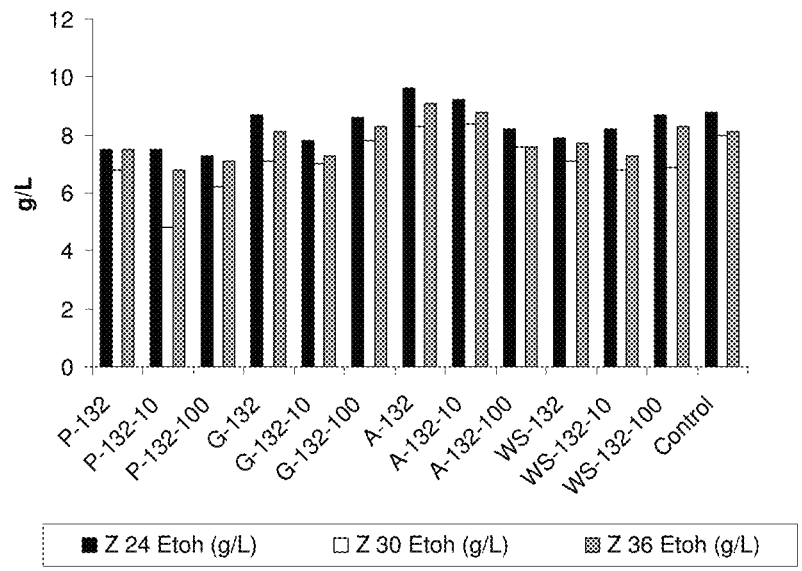
FIG. 8 is a graph showing ethanaol concentrations obtained utilizing Z. mobilis.
Figure 9:
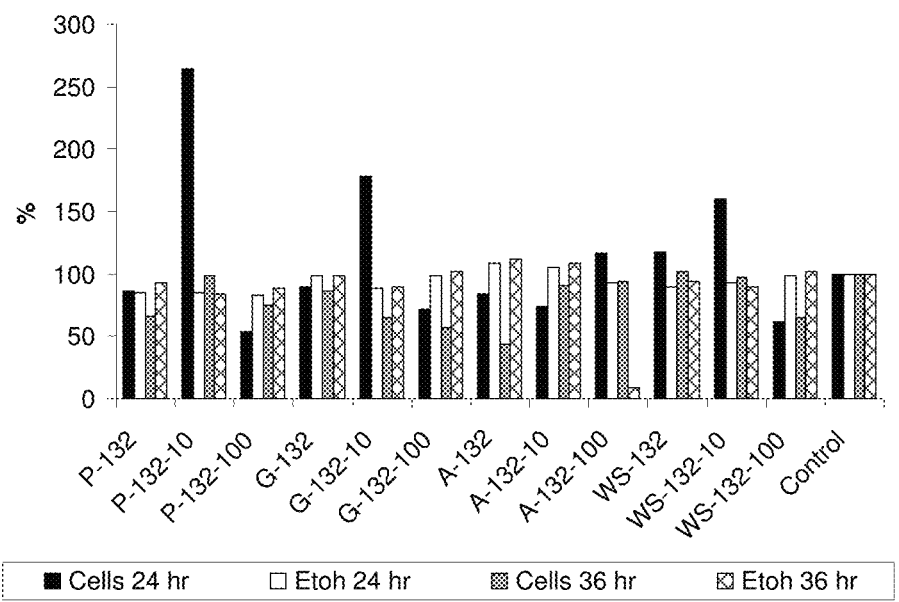
FIG. 9 is a graph showing the percentage of growth and ethanol production obtained utilizing Z. mobilis.

Together, FIGS. 7 and 8 suggest that ethanol concentrations above about 6 g/L may be toxic to Z. mobilis. This data is also presented as a percentage normalized against the control, as shown in FIG. 9.

*Pichia stipitis*

Figure 10:
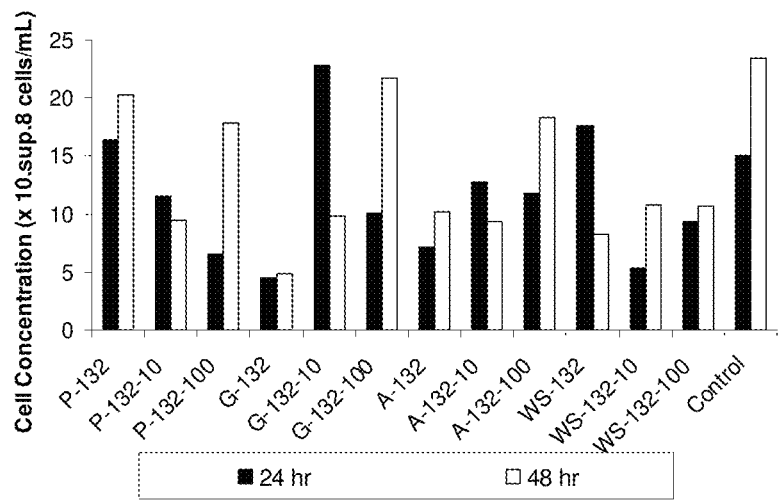
FIG. 10 is a graph showing cell concentrations for P. stipitis.

As shown in FIG. 10, cell numbers were comparable to the control. Furthermore, although slightly reduced cell numbers were present in samples containing G-132 and WS-132, reduced cell numbers were not observed for G-132-10, G-132-100, A-132-10, or A-132-100. Thus, it is unlikely that substrates G or A are toxic. Rather, the reduced cell numbers observed for G-132 and WS-132 are likely to have been caused by an experimental anomaly or by the presence of unprocessed substrate somehow impeding cell growth. Overall, this data suggests that glucose present in the control and experimental samples is likely to be sufficient to promote optimal *P. stipitis* growth, and that the presence of an additional substrate in the sample does not increase this growth rate. These results also suggest that none of the samples are toxic in *P. stipitis*.

Figure 11:
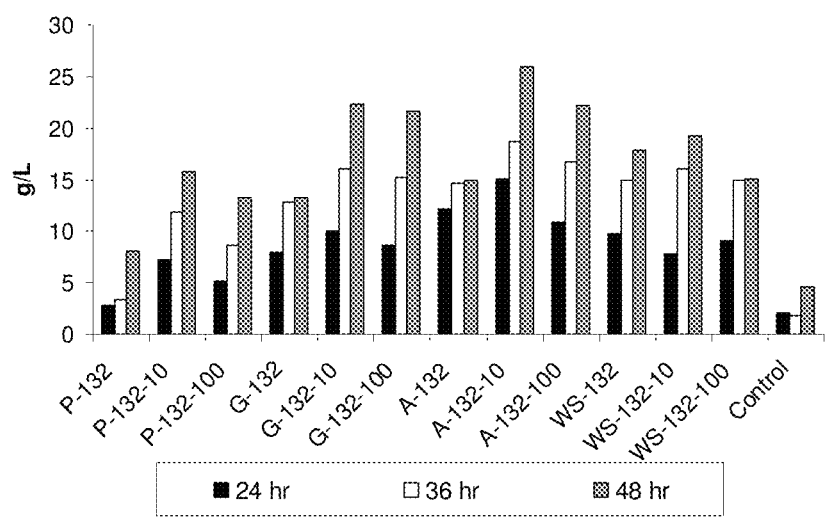
FIG. 11 is a graph showing ethanaol concentrations obtained utilizing P. stipitis.

As shown in FIG. 11, despite the similar cell numbers reported in FIG. 11, greatly increased ethanol production was observed in all samples containing an experimental substrate. Ethanol concentrations increased over time for each of the three time points tested. The highest concentration of ethanol was observed for A-132-10 at the 48 hour time point (e.g., approximately 26.0 g/L). By comparing the substrate concentrations with the highest levels of ethanol production with the cell number data presented in FIG. 11, it can be seen that *P. stipitis* do not appear to be sensitive to increasing ethanol concentrations. Furthermore, ethanol production does not appear to be related to cell number, but rather appears to be related to the type of substrate present in the sample.

Figure 12:
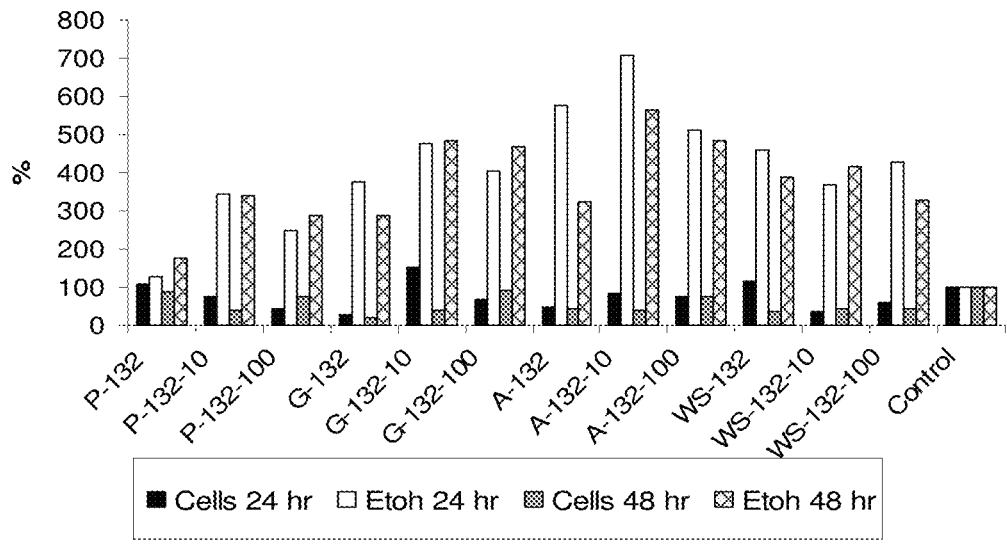
FIG. 12 is a graph showing the percentage of growth and ethanol production obtained utilizing P. stipitis.

Together, the results presented in FIG. 10 and FIG. 11 suggest that the experimental substrates do not promote increased *P. stipitis* growth, however, they greatly increase the amount of ethanol produced by this cell type. This data is also presented as a percentage normalized against the control, as shown in FIG. 12.

*Saccharomyces cerevisiae*

Figure 13:
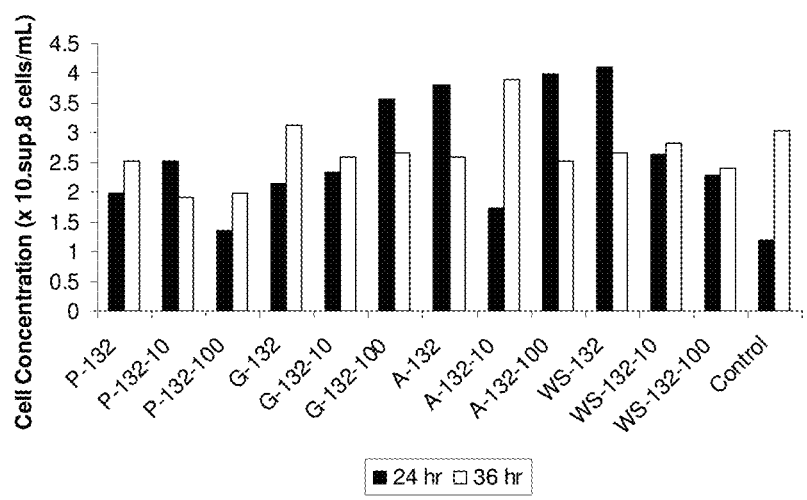
FIG. 13 is a graph showing cell concentrations for S. cerevisiae.

As shown in FIG. 13, G-132-100, A-132, A-132-10, A-132-100, and WS-132 promoted slightly elevated cell numbers compared to the control. No significant reductions in cell number were observed for any sample. These results suggest that none of the samples are toxic in *S. cerevisiae*.

Figure 14:
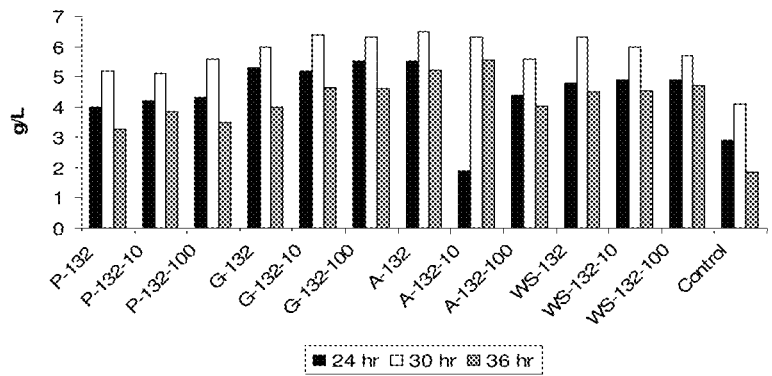
FIG. 14 is a graph showing ethanol concentrations obtained utilizing S. cerevisiae.

As shown in FIG. 14, increased ethanol production was observed in cells treated with each cell type compared to the control. Comparison of those samples containing the highest amount of ethanol with the cell number data presented in FIG. 13 suggests that ethanol concentrations in excess of 5 g/L may have had an adverse effect on cell numbers. However, this observation is not the case for all samples.

Figure 15:
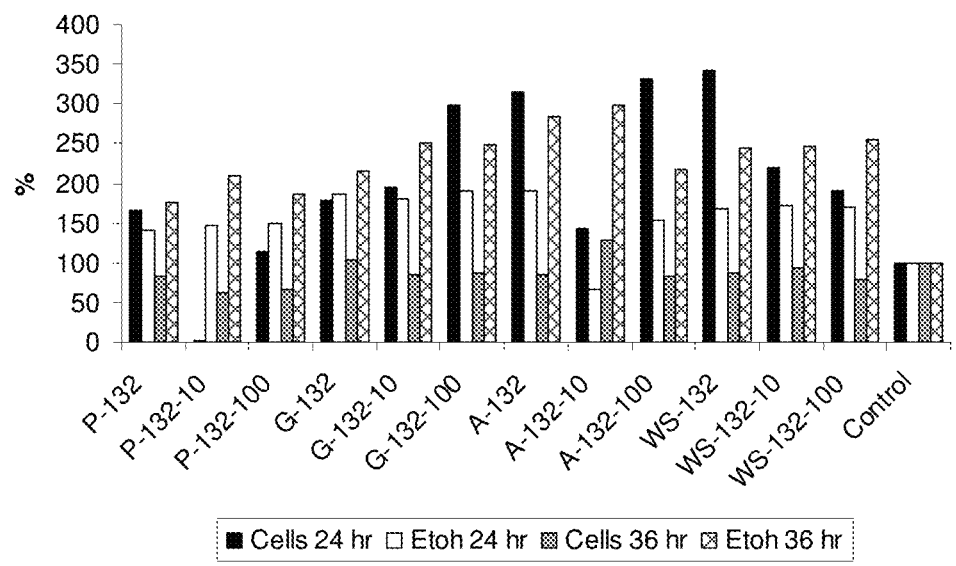
FIG. 15 is a graph showing the percentage of growth and ethanol production obtained utilizing S. cerevisiae.

This data is also presented as a percentage normalized against the control, as shown in FIG. 15.

In conclusion, none of the samples tested appeared to be toxic in *Z. mobilis*, *P. stipitis*, or *S. cerevisiae*. Furthermore, *P. stipitis* appeared to be the most efficient of the three cell types for producing ethanol from the experimental substrates tested.

Other Embodiments

A number of embodiments of the invention have been described. Nevertheless, it will be understood that various modifications may be made without departing from the spirit and scope of the invention.

For example, the fibers can be in any desired form, and can have a variety of different morphologies. Generally, it is desirable that the cellulosic material have a high surface area. In some cases, the fibers may be incorporated into single or multi-layer sheets, e.g., the fibers may be part of a HEPA filter or the like. The sheet material can have a surface area of, for example, from about 1 to 500 $m^2/g$. The fibrous material can be overlaid, e.g., meltblown, folded, in the form of a screen or mesh, or provided in other geometries. The fibers may be extruded or coextruded.

The fibers may have any desired particle size, from nanoscale, e.g., less than about 1000 nm, e.g., less than 500 nm, 250 nm, 100 nm, 50 nm, 25 nm, or even less than 1 nm, to large particle sizes, e.g., greater than 100 microns, 200 microns, 500 microns or even 1000 microns, or agglomerates of particles.

While biomass substrates have been discussed herein, such substrates can be used in combination with other substrates, for example the inorganic and synthetic substrates disclosed in U.S. Provisional Application No. 61/252,300, filed Oct. 16, 2009, the full disclosure of which is incorporated herein by reference.

The fibers or a fibrous material containing the fibers may be pretreated with a microorganism and/or enzyme, and/or the fibers or fibrous material can be contacted with a microoganism and/or enzyme during a bioprocess such as saccharification or fermentation.

As discussed above, enzymes can be immobilized on the fibers, instead of or in addition to microorganisms.

Enzymes and biomass-destroying organisms that break down biomass, such as the cellulose and/or the lignin portions of the biomass, contain or manufacture various cellulolytic enzymes (cellulases), ligninases or various small molecule biomass-destroying metabolites. These enzymes may be a complex of enzymes that act synergistically to degrade crystalline cellulose or the lignin portions of biomass. Examples of cellulolytic enzymes include: endoglucanases, cellobiohydrolases, and cellobiases (β-glucosidases). During saccharification, a cellulosic substrate is initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble 1,4-linked dimer of glucose. Finally cellobiase cleaves cellobiose to yield glucose.

A cellulase is capable of degrading biomass and may be of fungal or bacterial origin. Suitable enzymes include cellulases from the genera *Bacillus, Pseudomonas, Humicola, Fusarium, Thielavia, Acremonium, Chrysosporium* and *Trichoderma*, and include species of *Humicola, Coprinus, Thielavia, Fusarium, Myceliophthora, Acremonium, Cephalosporium, Scytalidium, Penicillium* or *Aspergillus* (see, e.g., EP 458162), especially those produced by a strain selected from the species *Humicola insolens* (reclassified as *Scytalidium thermophilum*, see, e.g., U.S. Pat. No. 4,435,307), *Coprinus cinereus, Fusarium oxysporum, Myceliophthora thermophila, Meripilus giganteus, Thielavia terrestris, Acremonium* sp., *Acremonium persicinum, Acremonium acremonium, Acremonium brachypenium, Acremonium dichromosporum, Acremonium obclavatum, Acremonium pinkertoniae, Acremonium roseogriseum, Acremonium incol-*

*oratum*, and *Acremonium furatum*; preferably from the species *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes may also be obtained from *Chrysosporium*, preferably a strain of *Chrysosporium lucknowense*. Additionally, *Trichoderma* (particularly *Trichoderma viride, Trichoderma reesei*, and *Trichoderma koningii*), alkalophilic *Bacillus* (see, for example, U.S. Pat. No. 3,844,890 and EP 458162), and *Streptomyces* (see, e.g., EP 458162) may be used.

Suitable cellobiases include a cellobiase from *Aspergillus niger* sold under the tradename NOVOZYME 188™.

Enzyme complexes may be utilized, such as those available from Genencor under the tradename ACCELLERASE®, for example, Accellerase® 1500 enzyme complex. Accellerase® 1500 enzyme complex contains multiple enzyme activities, mainly exoglucanase, endoglucanase (2200-2800 CMC U/g), hemi-cellulase, and beta-glucosidase (525-775 pNPG U/g), and has a pH of 4.6 to 5.0. The endoglucanase activity of the enzyme complex is expressed in carboxymethylcellulose activity units (CMC U), while the beta-glucosidase activity is reported in pNP-glucoside activity units (pNPG U). In one embodiment, a blend of Accellerase® 1500 enzyme complex and NOVOZYME™ 188 cellobiase is used.

Accordingly, other embodiments are within the scope of the following claims.

The invention claimed is:

1. A fermentation system comprising:
   a functionalizing module configured to produce a functionalized biomass,
   a substrate-forming module configured to immobilize a microorganism on the functionalized biomass, producing a substrate in the form of a fibrous sheet having the microorganism immobilized thereon by ionic bonding of complementary charged groups on the functionalized biomass and the microorganism,
   a fermentation tank,
   a substrate delivery system configured to deliver the substrate to the fermentation tank, and
   a recovery module configured to recover the substrate after a fermentation process,
   wherein the functionalizing module includes a particle beam accelerator for irradiating a biomass feedstock and forming functional groups thereupon, and
   the substrate delivery system is configured to also deliver a low molecular weight sugar dissolved in a solution to the fermentation tank.

2. The fermentation system of claim 1 wherein the sheet is a multilayer sheet.

3. The fermentation system of claim 1 wherein the sheet is overlaid, folded, or in the form of a screen or mesh.

4. The fermentation system of claim 1 wherein the biomass feedstock comprises internal fibers that has been sheared to an extent that its internal fibers are substantially exposed.

5. The fermentation system of claim 4 wherein the biomass fibers have a porosity greater than 70%.

6. The fermentation system of claim 4 wherein the biomass fibers are extruded or coextruded.

7. The fermentation system of claim 1 further comprising a module for mechanically treating the biomass feedstock.

8. The fermentation system of claim 7 wherein the module for mechanically treating is designed to change the morphology of the biomass feedstock, wherein the morphology that is changed is selected from the group consisting of surface area, porosity, bulk density and mechanically treated fiber length to width ratio.

9. The fermentation system of claim 8 wherein the mechanically treated fibers have an average length of 0.5 mm to 2.5 mm and the length-to-diameter ratio is greater than 8/1.

10. The fermentation system of claim 1 wherein the functionalization module can deliver a radiation dose of between 1 and 100 Mrad.

11. The fermentation system of claim 1 wherein the system includes one or more holding tanks, stripping columns, distillation units, mixers and drying units.

12. The fermentation system of claim 1 wherein the functionalization module is located at a different site from the substrate delivery system and fermentation tank, and the system includes a method of transportation between the different sites selected from a truck, a boat, a plane or a train.

13. The fermentation system of claim 1 wherein the recovery module is configured to recover the substrate with the microorganism in a condition that will allow the substrate to be reused for more than one fermentation.

14. The fermentation system of claim 1, wherein the particle beam accelerator delivers particles heavier than electrons.

15. The fermentation system of claim 14, wherein the particles heavier than electrons are nitrogen atoms or oxygen atoms.

16. The fermentation system of claim 14, wherein the particles heavier than electrons are phosphorous atoms.

17. The fermentation system of claim 14, wherein the particles heavier than electrons are sulfur atoms.

18. The fermentation system of claim 14, wherein the particles heavier than electrons are selected from the group consisting of protons, helium nuclei, argon ions, silicon ions, neon ions, carbon ions, phosphorus ions, oxygen ions and nitrogen ions.

* * * * *